United States Patent
Lee et al.

(10) Patent No.: US 11,421,194 B2
(45) Date of Patent: Aug. 23, 2022

(54) PUMPLESS PLATFORM FOR HIGH-THROUGHPUT DYNAMIC MULTICELLULAR CULTURE AND CHEMOSENSITIVITY EVALUATION

(71) Applicants: Hackensack Meridian Health Center For Discovery and Innovation, Nutley, NJ (US); The Trustees of the Stevens Institute of Technology, Hoboken, NJ (US)

(72) Inventors: Woo Lee, Lyndhurst, NJ (US); Zhehuan Chen, Jersey City, NJ (US); Jenny Zilberberg, Yardley, PA (US)

(73) Assignees: THE TRUSTEES OF THE STEVENS INSTITUTE OF TECHNOLOGY, Hoboken, NJ (US); HACKENSACK MERIDIAN HEALTH CENTER FOR DISCOVERY AND INNOVATION, Nutley, NJ (US)

( * ) Notice: Subject to any disclaimer, the term of this patent is extended or adjusted under 35 U.S.C. 154(b) by 365 days.

(21) Appl. No.: 16/703,218

(22) Filed: Dec. 4, 2019

(65) Prior Publication Data
US 2020/0181551 A1    Jun. 11, 2020

Related U.S. Application Data

(60) Provisional application No. 62/883,509, filed on Aug. 6, 2019, provisional application No. 62/776,070, filed on Dec. 6, 2018.

(51) Int. Cl.
*C12M 3/00*    (2006.01)
*B01L 3/00*    (2006.01)
(Continued)

(52) U.S. Cl.
CPC ....... *C12M 21/08* (2013.01); *B01L 3/502746* (2013.01); *C12N 5/0062* (2013.01);
(Continued)

(58) Field of Classification Search
CPC .............................. C12M 21/08; C12M 23/16
See application file for complete search history.

(56) References Cited

U.S. PATENT DOCUMENTS 7,981,362 B2   7/2011  Glezer et al.
8,748,180 B2   6/2014  Shuler et al.
(Continued)

OTHER PUBLICATIONS

Yaccoby, S. Advances in the understanding of myeloma bone disease and tumour growth. Br J Haematol. (2010) 149 (3): 311-321.
(Continued)

*Primary Examiner* — Nathan A Bowers
(74) *Attorney, Agent, or Firm* — McCarter & English, LLP

(57) ABSTRACT

The described invention provides an ex vivo dynamic multiple myeloma cancer niche contained in a pumpless perfusion culture device. The dynamic multiple myeloma cancer niche includes (a) a three-dimensional tissue construct containing a dynamic ex vivo bone marrow niche, which contains a mineralized bone-like tissue containing viable osteoblasts self-organized into cohesive multiple cell layers and an extracellular matrix secreted by the viable adherent osteoblasts; and a microenvironment dynamically perfused by nutrients and dissolved gas molecules; and (b) human myeloma cells seeded from a biospecimen composition comprising mononuclear cells and the multiple myeloma cells. The human myeloma cells are in contact with osteoblasts of the bone marrow niche, and the viability of the human myeloma cells is maintained by the multiple myeloma cancer niche.

25 Claims, 12 Drawing Sheets
(11 of 12 Drawing Sheet(s) Filed in Color)

(51) Int. Cl.
  *C12N 5/00* (2006.01)
  *C12N 5/078* (2010.01)
  *C12N 5/09* (2010.01)
  *G01N 33/50* (2006.01)
  *C12N 5/077* (2010.01)

(52) U.S. Cl.
  CPC ......... *C12N 5/0068* (2013.01); *C12N 5/0634* (2013.01); *C12N 5/0694* (2013.01); *G01N 33/5044* (2013.01); *G01N 33/5094* (2013.01); *B01L 2300/0829* (2013.01); *B01L 2300/0851* (2013.01); *C12N 5/0654* (2013.01); *C12N 2502/1142* (2013.01); *C12N 2535/10* (2013.01)

(56) References Cited

U.S. PATENT DOCUMENTS

| | | | |
|---|---|---|---|
| 2014/0106452 A1 | 4/2014 | Vukasinovic | |
| 2014/0308688 A1* | 10/2014 | Grego | B01L 3/502715 435/7.92 |
| 2017/0267961 A1* | 9/2017 | Hung | C12N 23/16 |
| 2018/0345280 A1* | 12/2018 | Vulto | B01L 9/527 |
| 2019/0002809 A1* | 1/2019 | Oakley | C12M 35/08 |
| 2019/0055510 A1 | 2/2019 | Lee et al. | |

OTHER PUBLICATIONS

Yamada, H., et al. Fabrication of gravity-driven microfluidic device. Rev. Sci. Instrum., 2008, 79, 124301.

Yata K. and Yaccoby S. The SCID-rab model: a novel in vivo system for primary human myeloma demonstrating growth of CD138-expressing malignant cells. Leukemia 2004; 18: 1891-7.

Ye BH, et al., Alterations of a zinc finger-encoding gene, BCL-6, in diffuse large-cell lymphoma. Science. 1993; 262: 747-750.

Ye, N., et al. Cell-based high content screening using an integrated microfluidic device, Lab Chip, 2007, 7, 1696-1704.

Young, E.W.K., et al. Rapid prototyping of arrayed microfluidic systems in polystyrene for cell-based assays. Anal. Chem., 2011, 83, 1408-1417.

Yuen, P.K. and Goral, V.N. Low-cost rapid prototyping of flexible microfluidic devices using a desktop digital craft cutter. Lab Chip, 2010, 10, 384-387.

Zhang, W. et al., Ex Vivo Maintenance of Primary Human Multiple Myeloma Cells through the Optimization of the Osteoblastic Niche. PLoS One, 2015, 10, 1-19.

Zhang, W. et al. Patient-Specific 3D Microfluidic Tissue Model for Multiple Myeloma. Tissue Eng. Part C Methods, 2014, 20, 663-670.

Zhang, W., et al. Well Plate-Based Perfusion Culture Device for Tissue and Tumor Microenvironment Replication. Lab Chip, 2015, 15, 2854-63.

Zhu, X., et al. , Arrays of horizontally-oriented mini-reservoirs generate steady microfluidic flows for continuous perfusion cell culture and gradient generation. Analyst, 2004, 129, 1026-1031.

Zlei, M, et al. Characterization of in vitro growth of multiple myeloma cells. Exp Hematol 2007; 35: 1550-61.

Zver, S. et al., Cardiac Toxicity of High-Dose Cyclophosphamide in Patients with Multiple Myeloma Undergoing Autologous Hematopoietic Stem Cell Transplantation. Intl J. Hematol. 85(5): 408-14 (2007).

Chen, et al., Pumpless platform for high-throughput dynamic multicellular culture and chemosensitivity evaluation. Lab on a Chip, vol. 19, 254-261, Dec. 11, 2018.

Grove, E.A., Wnt signaling meets internal dissent. Genes and Development. 2011 25: 1759-1762.

Hardy, RR, and Hayakawa, K. B Cell Development Pathways. Ann. Rev. Immunol. (2001) 19: 595-621.

Harkness, T., et al. High-content imaging with micropatterned multiwell plates reveals influence of cell geometry and cytoskeleton on chromatin dynamics Biotechnol. J., 2015, 10, 1555-1567.

Hayakawa K, et al. The"Ly-1 B" cell subpopulation in normal immunodefective, and autoimmune mice.. J Exp Med. 1983; 157: 202-218.

Hayflick, L. The limited in vitro lifetime of human diploid cell strains. Exptl Cell Res. (1965) 37: 614-636.

Hideshima T, et al., Advances in biology of multiple myeloma: clinical applications. Blood. 2004; 104(3): 607-618.

Hou, Z. et al., Osteoblast-specific gene expression after transplantation of marrow cells: Implications for skeletal gene therapy. Proc. Natl. Acad. Sci., 96: 7294-7299, Jun. 1999.

Jacob J, et al., Intraclonal generation of antibody mutants in germinal centres. Nature. 1991; 354: 389-392.

Jakubikova, J, et al. A novel 3D mesenchymal stem cell model of the multiple myeloma bone marrow niche: biologic and clinical applications . Oncotarget, 2016, 7: 77326-77341.

Janeway CA, et al., The B cell is the initiating antigen-presenting cell in peripheral lymph nodes. J Immunol. 1987; 138: 1051-1055.

Jiang, W.G. and S. Hiscox, S., Hepatocyte growth factorlscatter factor, a cytokine playing multiple and converse roles Histol. Histopathol. 2: 537-555 (1997).

Kapur, S., et al. Fluid flow shear stress stimulates human osteoblast proliferation and differentiation through multiple interacting and competing signal transduction pathways. Bone, 2003, 32, 241-251.

Karadag A, et al. Human myeloma cells promote the production of interleukin 6 by primary human osteoblasts. British Journal of Haematology. 2000; 108(2): 383-390.

Kelsoe G., Life and death in germinal centers (redux). Immunity. 1996; 4: 107-111.

Kerkelä, R., et al., Cardiotoxicity of the cancer therapeutic agent imatinib mesylate. Nat. Med. 12: 908-16 (2006).

Khin, ZP, et al. A Preclinical Assay for Chemosensitivity in Multiple Myeloma. Cancer Res., 2014, 74: 56-67.

Kim, T. and Cho, Y.-H. A pumpless cell culture chip with the constant medium perfusion-rate maintained by balanced droplet dispensing†. Lab Chip, 2011, 11, 1825.

Kini Bailur J, et al. Changes in bone marrow innate lymphoid cell subsets in monoclonal gammopathy: target for IMiD therapy. Blood Adv. Nov. 28, 2017; 1(25):2343-2347.

Kirshner J, et al., Aunique three-dimensional model for evaluating the impact of therapy on multiple myeloma. Blood 2008; 112: 2935-45.

Kolf, C.M., et al., Mesenchymal stromal cells Biology of adult mesenchymal stem cells: regulation of niche, self-renewal and differentiation. Arthritis Research & Therapy 2007, 9:204.

Komine, A., et al., Establishment of adipose-derived mesenchymal stem cell lines from a p53-knockout mouse. Biochem. Biophys. Res. Commun. Oct. 5, 2012; 426(4): 468-474.

Korsmeyer SJ, et al., Immunoglobulin Gene Rearrangement and Cell Surface Antigen Expression in Acute Lymphocytic Leukemias of T Cell and B Cell Precursor Origins. J Clin Invest. 1983; 71: 301-313.

Krishnan, V., et al., Regulation of bone mass by Wnt signaling. The Journal of Clinical Investigation, vol. 116, No. 5, May 2006, pp. 1202-1209.

Kuehl, WM. and Bergsagel, PL. Molecular pathogenesis of multiple myeloma and its premalignant precursor. J Clin Invest. (2012) 122 (10): 3456-63.

Kumar S, et al., Expression of VEGF and its receptors by myeloma cells. Leukemia. 2003; 17(10): 2025-2031.

Kumar S, et al., Prognostic value of bone marrow angiogenesis in patients with multiple myeloma undergoing high-dose therapy. Bone Marrow Transplantation. 2004; 34(3): 235-239.

Kumar, S. K. et al. Improved survival in multiple myeloma and the impact of novel therapies. Blood, 2008, 111, 2516-2520.

Kuppers R, et al., Hodgkin disease: Hodgkin and Reed-Sternberg cells picked from histological sections show clonal immunoglobulin gene rearrangements and appear to be derived from B cells at various stages of development. Proc Natl Acad Sci U S A. 1994; 91: 10962-10966.

Kyle R A et al., Multiple myeloma. Blood. 2008; 111: 2962-2972.

Kyle RA., The American Society of Hematology: a success at age 50; blood banking and sodium citrate. Blood 2008; 111: 4417-8.

(56) References Cited

OTHER PUBLICATIONS

Lanzavecchia A., Antigen-specific interaction between T and B cells. Nature. 1985; 314: 537-539.
Lebien TW, and Tedder, TF. B lymphocytes: how they develop and function. Blood (2008) 112 (5): 1570-80.
Lee, H.J., et al., Changes in Surface Markers of Human Mesenchymal Stem Cells During the Chondrogenic Differentiation and Dedifferentiation Processes In Vitro. Arthritis & Rheumatism, vol. 60, No. 8, Aug. 2009, pp. 2325-2332.
Lentzsch S, et al. Pathophysiology of Multiple Myeloma Bone Disease. Hematol Oncol Clin North Am 2007; 21: 1035-49.
Liu, G., et al., Canonical Wnts function as potent regulators of osteogenesis by human mesenchymal stem cells. JCB, vol. 185, No. 1, 2009, pp. 67-75.
Loberg, RD, et al., Enhanced Glycogen Synthase Kinase-3 Activity Mediates Hypoxia-induced Apoptosis of Vascular Smooth Muscle Cells and Is Prevented by Glucose Transport and Metabolism*. J. Biol. Chem. 277 (44):41667-673 (2002).
Majumdar, M.K. et al., Human Marrow-Derived Mesenchymal Stem Cells (MSCs) Express Hematopoietic Cytokines and Support Long-Term Hematopoiesis When Differentiated Toward Stromal and Osteogenic Lineages. J. Hematother. Stem Cell Res. Dec. 2000; 9(6): 841-848.
Marom, R. et al., Characterization of Adhesion and Differentiation Markers of Osteogenic Marrow Stromal Cells. Journal of Cellular Physiology 202: 4148 (2005).
Matsumoto, K. et al, Growth factor regulation of integrin-mediated cell motility. Cancer Metastasis Rev. 14: 205-217 (1995).
McHeyzer-Williams LJ, and McHeyzer-Williams MG., Antigen-Specific Memory B Cell Development. Annu Rev Immunol. 2005; 23: 487-513.
Merchionne F et al., New Therapies in Multiple Myeloma. Clin Exp Med. 2007; 7: 83-97.
Minguell, J.J., et al., Mesenchymal Stem Cells. Experimental Biology and Medicine 2001, 226: 507-520.
Mohty B, et al., Treatment strategies in relapsed and refractory multiple myeloma: a focus on drug sequencing and retreatment approaches in the era of novel agents. Leukemia 2012; 26: 73-85.
Montecino-Rodriguez E, et al. Identification of a B-1 B cell-specified progenitor. Nat Immunol. 2006; 7: 293-301.
Nefedova Y, et al., Involvement of Notch-1 signaling in bone marrow stroma-mediated de novo drug resistance of myeloma and other malignant lymphoid cell lines. Blood. 2004; 103(9): 3503-3510.
Niziolek, P.J., et al., High-bone-mass-producing mutations in the Wnt signaling pathway result in distinct skeletal phenotypes. Bone Nov. 2011; 49(5): 1010-1019.
Novak, A. and Dedhar, S., Signaling through ß-catenin and Lef/Tcf. Cell. Mol. Life Sci. Oct. 30, 1999; 56(5-6); 523-537.
Nutt SL, et al., Commitment to the B-lymphoid lineage depends on the transcription factor Pax5. Nature. 1999; 401: 556-562.
Otjacques E, et al. Biological aspects of angiogenesis in multiple myeloma. Int J Hematol 2011; 94: 505-18.
Pak, C, et al. MicroC3: an ex vivo microfluidic cis-coculture assay to test chemosensitivity and resistance of patient multiple myeloma cells†. Integr. Biol., 2015, 7: 643-654.
Paul, W. E., "Chapter 1: The immune system: an introduction," Fundamental Immunology, 4th Edition, Ed. Paul, W. E., Lippicott-Raven Publishers, Philadelphia (1999).
Pillai S, et al., Marginal Zone B Cells. Annu Rev Immunol. 2005; 23: 161-196.
Podar K. and Anderson KC. The pathophysiologic role of VEGF in hematologic malignancies: therapeutic implications. Blood. 2005; 105(4): 1383-1395.
Pratt G. Molecular aspects of multiple myeloma. J Clin Pathol: Molec Pathol. (2002) 55: 273-83.
Quarto, N., et al., Opposite Spectrum of Activity of Canonical Wnt Signaling in the Osteogenic Context of Undifferentiated and Differentiated Mesenchymal Cells: Implications for Tissue Engineering. Tissue Engineering: Part A, 16(10), 2010, pp. 3185-3197.
Raab MS, et al., Multiple myeloma. Lancet 2009; 374: 324-39.
Radbruch A, et al., Competence and competition: the challenge of becoming a long-lived plasma cell. Nat Rev Immunol. 2006; 6: 741-750.
Radtke F, Raj K. The Role of Notch in Tumorigenesis: Oncogene or Tumour Suppressor?. Nature Reviews Cancer. 2003; 3(10): 756-767.
Raje N, Roodman GD. Advances in the Biology and Treatment of Bone Disease in Multiple Myeloma. Clin Cancer Res 2011 17: 1278-86.
Rajkumar SV. and Witzig TE. A review of angiogenesis and antiangiogenic therapy with thalidomide in multiple myeloma. Cancer Treatment Reviews 2000; 26(5): 351-362.
Rajkumar, SV, Thalidomide: Tragic Past and Promising Future. Mayo Clin Proc. 2004; 79: 899-903.
Reagan, MR, et al. Investigating osteogenic differentiation in multiple myeloma using a novel 3D bone marrow niche model. Blood, 2014, 124: 3250-3259.
Reiser, J., et al., Potential of mesenchymal stem cells in gene therapy approaches for inherited and acquired diseases. Expert. Opin. Biol. Ther. Dec. 2005; 5(12): 1571-1584.
Ria R, et al., Gene Expression Profiling of Bone Marrow Endothelial Cells in Patients with Multiple Myeloma. Clinical Cancer Research 2009; 15(17): 5369-5378.
Roccaro AM, et al., Stroma-Derived Exosomes Mediate Oncogenesis in Multiple Myeloma. Abstract 625. Blood 2011; 118 ASH Annual Meeting Abstracts. .doi: https://doi.org/10.1182/blood.V118.21.625.625.
Ron Y, and Sprent J., T cell priming in vivo: a major role for B cells in presenting antigen to T cells in lymph nodes . . . J Immunol. 1987; 138: 2848-2856.
Ron Y, et al., Defective induction of antigen-reactive proliferating T cells in B cell-deprived mice. Eur J Immunol. 1981; 11: 964-968.
Roodman GD., Osteoblast function in myeloma. Bone 2011; 48: 135-40.
Roodman GD., Role of the Bone Marrow Microenvironment in Multiple Myeloma. J Bone Miner Res 2002; 17: 1921-5.
Ryoo, H.M., et al., Stage-Specific Expression of Dlx-5 during Osteoblast Differentiation: Involvement in Regulation of Osteocalcin Gene Expression. Mol. Endo. 1997, 11(11): 1681-1694.
Schwartz R N et al., Current and Emerging Treatments for Multiple Myeloma. JMCP, Sep. 2008, vol. 14, No. 7, pp. S12-S18.
Schwartz RN. and Vozniak M., Current and Emerging Treatments for Multiple Myeloma. J Manag Care Pharm 2008; 14: 12-9.
Sehgal K, et al. Clinical and pharmacodynamic analysis of pomalidomide dosing strategies in myeloma: impact of immune activation and cereblon targets. Blood (2015) 125:4042-51.
Shapiro-Shelef M. and Calame K., Regulation of Plasma-Cell Development. Nat Rev Immunol. 2005; 5: 230-242.
Shapiro-Shelef, M. et al. Blimp-1 Is Required for the Formation of Immunoglobulin Secreting Plasma Cells and Pre-Plasma Memory B Cells. Immunity (2003) 19: 607-20.
Shen, J., et al., Transplantation of mesenchymal stem cells from young donors delays aging in mice. (2011) Scientific Reports, 1:67, DOI: 10.1038/srep00067.
Shipman CM, Croucher PI. Osteoprotegerin Is a Soluble Decoy Receptor for Tumor Necrosis Factor-related Apoptosis-inducing Ligand/Apo2 Ligand and Can Function as a Paracrine Survival Factor for Human Myeloma Cells1. Cancer Research. 2003; 63(5): 912-916.
Silva, A, et al. An Ex Vivo Platform for the Prediction of Clinical Response in Multiple Myeloma. Cancer Res., 2017, 77: 3336-3351.
Stanley ER, et al., Biology and action of colony-stimulating factor-1. Mol. Reprod. Dev. 46 (1): 4-10 (1997).
Steiniger B, et al. The splenic marginal zone in humans and rodents: an enigmatic compartment and its inhabitants. Histochem Cell Biol. 2006; 126: 641-648.
Sugiura, S., et al. Pressure-driven perfusion culture microchamber array for a parallel drug cytotoxicity assay. Biotechnol. Bioeng., 2008, 100, 1156-1165.
Sung, J.H., et al., A microfluidic device for a pharmacokinetic-pharmacodynamic (PK-PD) model on a chip. Lab Chip, 2010, 10, 446-455.

(56) References Cited

OTHER PUBLICATIONS

Tanaka Y, et al. Myeloma Cell-Osteoclast Interaction Enhances Angiogenesis Together with Bone Resorption: A Role for Vascular Endothelial Cell Growth Factor and Osteopontin Clinical Cancer Research. 2007; 13(3): 816-823.
Temiz, Y., et al., Lab-on-a-chip devices: How to close and plug the lab?. Microelectron. Eng., 2015, 132, 156-175.
Thery, M, Micropatterning as a tool to decipher cell morphogenesis and functions. J. Cell Sci. (2010) 123 (24): 4201-13.
Tian E, et al., The Role of the Wnt-Signaling Antagonist DKK1 in the Development of Osteolytic Lesions in Multiple Myeloma. The New England Journal of Medicine. 2003; 349(26): 2483-2494.
Tsujimoto Y, et al., Cloning of the chromosome breakpoint of neoplastic B cells with the t(14;18) chromosome translocation. Science. 1984; 226: 1097-1099.
Tuan, R.S., et al., Adult mesenchymal stem cells and cell-based tissue engineering. Arthritis Res Ther 2003, 5:32-45.
Van Der Voort, R. et al., Paracrine Regulation of Germinal Center B Cell Adhesion through the c-Met-Hepatocyte Growth Factor/Scatter Factor Pathway. J. Exp. Med. 185: 2121-31 (1997).
Vanderkerken K, et al., Multiple myeloma biology: lessons from the 5TMM models. Immunol Rev 2003; 194: 196-206.
Vijayaragavan, K., et al., Noncanonical Wnt Signaling Orchestrates Early Developmental Events toward Hematopoietic Cell Fate from Human Embryonic Stem Cells. Cell Stem Cell 4,248-262, Mar. 6, 2009.
Naldschmidt, J, et al. A novel 3D high-throughput coculture platform for multiple myeloma ex-vivo sensitivity testing and drug screening. Clin. Lymphoma, Myeloma Leuk., 2015, 15: e224-e225.
Wang, Y.I., et al. Microfluidic Blood-Brain Barrier Model Provides In Vivo-Like Barrier Properties for Drug Permeability Screening. Biotechnol. Bioeng., 2017, 114, 184-194.
Weimar, I.S. et al., Hepatocyte growth factor/scatter factor promotes adhesion of lymphoma cells to extracellular matrix molecules via alpha 4 beta 1 and alpha 5 beta 1 integrins . . . Blood 89: 990-1000 (1997).
Wilkinson, GR. Chapter 1, Pharmacokinetics in Goodman and Gilman's the Pharmacological Basis of Therapeutics, 10th Edition, McGraw-Hill (New York) (2001).
Willert, J., et al., A transcriptional response to Wnt protein in human embryonic carcinoma cells. BMC Development Biology 2002, 2:8, pp. 1-7.
Xing, Y., et al. A pumpless microfluidic device driven by surface tension for pancreatic islet analysis. Biomed. Microdevices, 2016, 18, 80.
Yaccoby S, et al. Antibody-based inhibition of DKK1 suppresses tumor-induced bone resorption and multiple myeloma growth in vivo. Blood. 2007; 109(5): 2106-2111.
Yaccoby S, et al. Antimyeloma efficacy of thalidomide in the SCID-hu model. Blood 2002; 100: 4162-8.
Yaccoby S, et al. Myeloma interacts with the bone marrow microenvironment to induce osteoclastogenesis and is dependent on osteoclast activity. British Journal of Haematology. 2002; 116(2): 278-290.
Alberts, B., et al. Chapter 24: The adaptive immune system,, Molecular Biology of the Cell, Garland Science, NY, 2002.
Allen CD, et al. Germinal-Center Organization and Cellular Dynamics. Immunity. 2007; 27: 190-202.
Almeida, M., et al., Wnt Proteins Prevent Apoptosis of Both Uncommitted Osteoblast Progenitors and Differentiated Osteoblasts by beta-Catenin-dependent and -independent Signaling Cascades Involving Src/ERK and Phosphatidylinositol 3-Kinase/AKT. The Journal of Biological Chemistry, 280(50): 41342-41351, Dec. 16, 2005.
Arnsdorf, E.J., et al., Non-Canonical Wnt Signaling and N-Cadherin Related beta-Catenin Signaling Play a Role in Mechanically Induced Osteogenic Cell Fate. PLoS ONE, Apr. 2009, 4(4): e5388, pp. 1-10.
Baksh, D., et al. Cross-Talk Between Wnt Signaling Pathways in Human Mesenchymal Stem Cells Leads to Functional Antagonism During Osteogenic Differentiation. J. Cell Biochem., 2007, 101: 1109-1124.
Baksh, D., et al., Canonical and non-canonical wnts differentially affect the development potential of primary isolate of human bone marrow mesenchymal stem cells. J. Cell. Physiol., 2007, 212: 817-826.
Baraniak, P.R. and McDevitt, T.C., Stem cell paracrine actions and tissue regeneration. Regen. Med. Jan. 2010; 5(1): 121-143.
Bataille R, et al., Mechanisms of bone destruction in multiple myeloma: the importance of an unbalanced process in determining the severity of lytic bone disease. Journal of Clinical Oncology. 1989; 7(12): 1909-1914.
Bell E., Why 3D is better than 2D. Nature Reviews Immunology 2006; 6: 87.
Bennett, K.P., et al., Proteomics reveals multiple routes to the osteogenic phenotype in mesenchymal stem cells. BMC Genomics 2007, 8:380.
Braham, MVJ, et al. Endosteal and Perivascular Subniches in a 3D Bone Marrow Model for Multiple Myeloma. Tissue Eng. Part C Methods, 2018, 24: 300-312.
Burdon, T.J., et al., Bone Marrow Stem Cell Derived Paracrine Factors for Regenerative Medicine: Current Perspectives and Therapeutic Potential. Bone Marrow Research, vol. 2011, Article ID 207326.
Calimeri T, et al. A unique three-dimensional SCID-polymeric scaffold (SCID-synth-hu) model for in vivo expansion of human primary multiple myeloma cells. Leukemia 2011; 25: 707-11.
Chakraborty, S. Dynamics of capillary flow of blood into a microfluidic channel. Lab Chip, 2005, 5, 421.
Chen, S.Y.C., et al. Microfluidic array for three-dimensional perfusion culture of human mammary epithelial cells. Biomed. Microdevices, 2011, 13, 753-758.
Cheng, H. et al., Osteogenic Activity of the Fourteen Types of Human Bone Morphogenetic Proteins (BMPs). J. Bone & Joint Surgery 85: 1544-52 (2003).
Chotinantakul, K. and Leeanansaksiri, W., Hematopoietic Stem Cell Development, Niches, and Signaling Pathways. Bone Marrow Research, vol. 2012, Article ID 270425.
Chung JB, et al., Transitional B cells: step by step towards immune competence. Trends Immunol. 2003; 24: 342-349.
Cobaleda C, et al., Pax5: the guardian of B cell identity and function. Nat Immunol. 2007; 8: 463-470.
Cobaleda C, et al., Conversion of mature B cells into T cells by dedifferentiation to uncommitted progenitors. Nature. 2007; 449: 473-477.
Cook, D.N., The role of MIP-1alpha in Inflammation and hematopoiesis. J. Leukocyte Biol. 59(1): 61-66 (1996).
Coutinho A, and Moller G., Thymus-Independent B-Cell Induction and Paralysis. Adv Immunol. 1975; 21: 113.
D'Souza S, et al. Gfi1 expressed in bone marrow stromal cells is a novel osteoblast suppressor in patients with multiple myeloma bone disease. Blood 2011; 118: 6871-80.
De Groot, TE, et al. Surface-tension driven open microfluidic platform for hanging droplet culture. Lab Chip, 2016, 16: 334-44.
De La Puente, P, et al. 3D tissue-engineered bone marrow as a novel model to study pathophysiology and drug resistance in multiple myeloma. Biomaterials, 2015, 73: 70-84.
De Raeve HR. and Vanderkerken K., The role of the bone marrow microenvironment in multiple myeloma. Histol Histopathol 2005; 20: 1227-50.
Deleu S, et al. The effects of JNJ-26481585, a novel hydroxamate-based histone deacetylase inhibitor, on the development of multiple myeloma in the 5T2MM and 5T33MM murine models. Leukemia 2009; 23: 1894-1903.
Dilillo DJ, et al., Maintenance of Long-Lived Plasma Cells and Serological Memory Despite Mature and Memory B Cell Depletion during CD20 Immunotherapy in Mice. J Immunol. 2008; 180: 361-371.
Dimov, I.K., et al. Integrated microfluidic array plate (iMAP) for cellular and molecular analysis†. Lab Chip, 2011, 11, 2701.
Dorshkind K. and Montecino-Rodriguez, E., Fetal B-cell lymphopoiesis and the emergence of B-1-cell potential. Nat Rev Immunol. 2007; 7: 213-219.
Dvorak HF, et al., Tumor Microenvironment and Progression. J Surg Oncol 2011; 103: 468-74.

(56) References Cited

OTHER PUBLICATIONS

Edwards CM, et al. Increasing Wnt signaling in the bone marrow microenvironment inhibits the development of myeloma bone disease and reduces tumor burden in bone in vivo. Blood. 2008; 111(5): 2833-2842.

Ehrlich LA, Roodman GD.The role of immune cells and inflammatory cytokines in Paget's disease and multiple myeloma. Immunological Reviews. 2005; 208: 252-266.

Engler, A.J., et al., Matrix Elasticity Directs Stem Cell Lineage Specification. Cell 126, 677-689, Aug. 25, 2006.

Epstein, J. and Yaccoby, S., The SCID-hu Myeloma Model in Multiple Myeloma: Methods and Protocols, eds. R. D. Brown and P. J. Ho, Humana Press, Totowa, NJ, 2005, pp. 183-190.

Eslaminejad, M.B. and Yazdi, P.E., Mesenchymal Stem Cells: In Vitro Differentiation among Bone and Cartilage Cell Lineages. Yakhteh Medical Journal, 9(3), Autumn 2007, pp. 158-169.

Field-Smith A, et al., Bortezomib (Velcade™) in the treatment of multiple myeloma. Ther Clin Risk Manag 2006; 2: 271-9.

Fowler JA, et al., Tumor-host cell interactions in the bone disease of myeloma. Bone 2011; 48: 121-8.

Fowler, JA., et al. Bone Marrow Stromal Cells Create a Permissive Microenvironment for Myeloma Development: A New Stromal Role for Wnt Inhibitor Dkk1. Cancer Res. 72(9); 2183-9 (2012).

Fryer, RA et al. Characterization of a Novel Mouse Model of Multiple Myeloma and Its Use in Preclinical Therapeutic Assessment. PLoS One, 2013, 8, 1-9.

Fulciniti M, et al. Anti-DKK1 mAb (BHQ880) as a potential therapeutic agent for multiple myeloma. Blood. 2009; 114(2): 371-379.

Galimi, F. et al, The Hepatocyte Growth Factor and Its Receptor. Stem Cells 2: 22-30 (1993).

Gimbel, J.M., et al., In vitro Differentiation Potential of Mesenchymal Stem Cells. Transfus. Med. Hemother. 2008; 35: 228-238.

Gimble JM, The function of adipocytes in the bone marrow stroma. New Biol., Apr. 1990; 2(4): 304-312.

\* cited by examiner

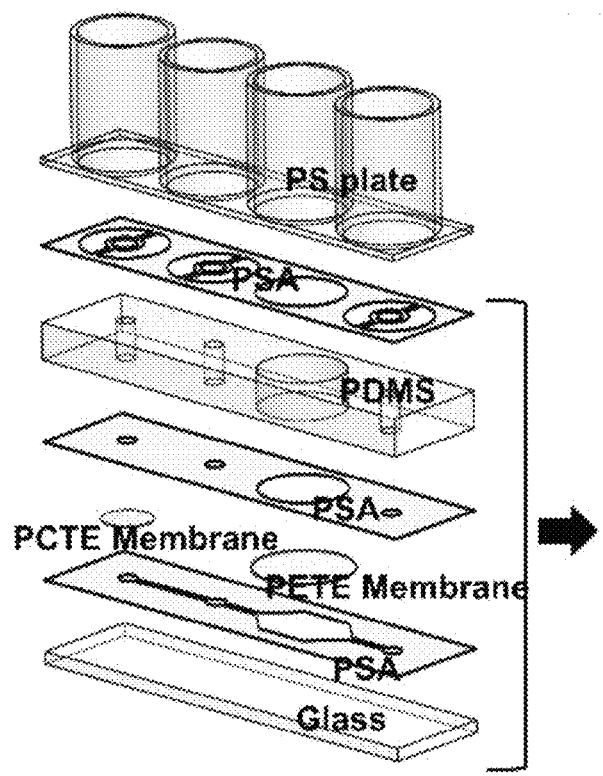
FIG. 5B
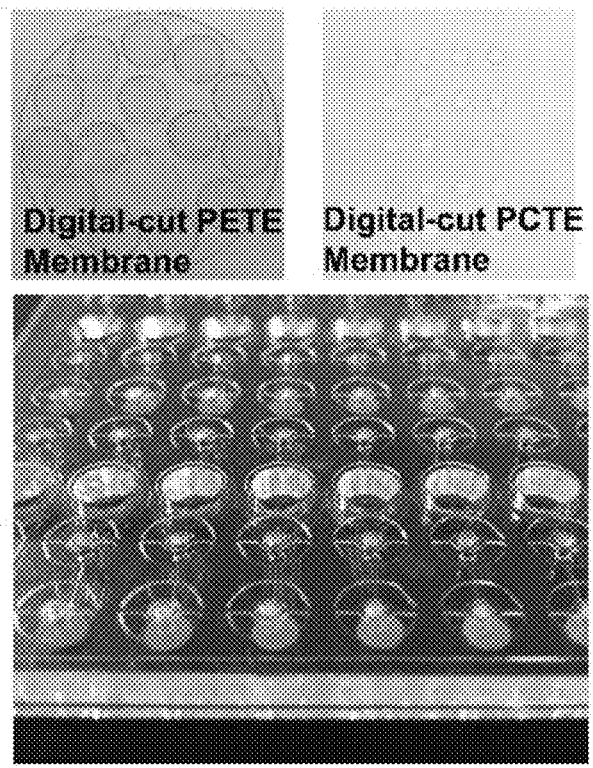
FIG. 5A
FIG. 5C

PUMPLESS PLATFORM FOR HIGH-THROUGHPUT DYNAMIC MULTICELLULAR CULTURE AND CHEMOSENSITIVITY EVALUATION

RELATED APPLICATIONS

This application claims the benefit of priority to U.S. Provisional Application 62/883,509 filed on Aug. 6, 2019 entitled "PUMPLESS PLATFORM FOR HIGH-THROUGHPUT DYNAMIC MULTICELLULAR CULTURE AND CHEMOSENSITIVITY EVALUATION," and to U.S. Provisional Application No. 62/776,070, filed on Dec. 6, 2018, entitled "PUMPLESS PLATFORM FOR HIGH-THROUGHPUT DYNAMIC MULTICELLULAR CULTURE AND CHEMOSENSITIVITY EVALUATION." The contents of each of these applications are incorporated by reference herein in their entirety.

STATEMENT REGARDING FEDERALLY SPONSORED RESEARCH

This invention was made with government support under Grant Number R33 CA212806 awarded by The National Institutes of Health. The government has certain rights in the invention.

FIELD OF INVENTION

The described invention relates to an ex-vivo well plate-based high-dynamic pumpless perfusion culture model of cell to cell interactions, and methods for testing personalized therapeutics using the model.

BACKGROUND

Tissue Compartments, Generally

In multicellular organisms, cells that are specialized to perform common functions are usually organized into cooperative assemblies embedded in a complex network of secreted extracellular macromolecules, the extracellular matrix (ECM), to form specialized tissue compartments. Individual cells in such tissue compartments are in contact with ECM macromolecules. The ECM helps hold the cells and compartments together and provides an organized lattice or construct within which cells can migrate and interact with one another. In many cases, cells in a compartment can be held in place by direct cell-cell adhesion. In vertebrates, such compartments may be of four major types, a connective tissue (CT) compartment, an epithelial tissue (ET) compartment, a muscle tissue (MT) compartment and a nervous tissue (NT) compartment, which are derived from three embryonic germ layers: ectoderm, mesoderm and endoderm. The NT and portions of the ET compartments are differentiated from the ectoderm; the CT, MT and certain portions of the ET compartments are derived from the mesoderm; and further portions of the ET compartment are derived from the endoderm.

The Bone Marrow Niche

The term "niche" as used herein refers to a specialized regulatory microenvironment, consisting of components which control the fate specification of stem and progenitor cells, as well as maintaining their development by supplying the requisite factors. The term "bone marrow (BM) niche" as used herein refers to a well-organized architecture composed of osteoblasts, osteoclasts, bone marrow endothelial cells, stromal cells, adipocytes and extracellular matrix proteins (ECM). These elements play an essential role in the survival, growth and differentiation of diverse lineages of blood cells.

Bone marrow consists of a variety of precursor and mature cell types, including hematopoietic cells (the precursors of mature blood cells) and stromal cells (the precursors of a broad spectrum of connective tissue cells), both of which appear to be capable of differentiating into other cell types. The mononuclear fraction of bone marrow contains stromal cells, hematopoietic precursors, and endothelial precursors.

Extracellular Matrix (ECM) Proteins

The ECM is a complex structural entity surrounding and supporting cells found within mammalian tissues. It comprises proteoglycans (e.g., heparan sulfate, chondroitin sulfate, keratin sulfate, hyaluronic acid), collagen, fibronectin, laminin and elastin. Most mammalian cells cannot survive unless they are anchored to the ECM. Cells attach to the ECM via transmembrane glycoproteins (e.g., integrins) which bind to various types of ECM proteins (e.g., collagens, laminins, fibronectin).

Adipocytes

Adipocytes of the bone marrow stroma provide the cytokines and extracellular matrix proteins required for the maturation and proliferation of the circulating blood cells. Due to the complexity of the bone marrow as an organ, the normal physiology of these stromal cells is not well understood. In particular, the role of adipocytes in the bone marrow remains controversial. Cloned bone marrow stromal cell lines provide an in vitro model for analysis of the lympho-hematopoietic microenvironment. These cells may be capable of multiple differentiation pathways, assuming the phenotype of adipocytes, chondrocytes, myocytes, and osteocytes in vitro. (Gimble J M, New Biol., 1990 April; 2(4): 304-312).

Hematopoietic Stem Cell Development and Maintenance

Hematopoietic stem cells (HSCs) (also known as the colony-forming unit of the myeloid and lymphoid cells (CFU-M,L, or CD34+ cells) are rare pluripotential cells within the blood-forming organs that are responsible for the continued production of blood cells during life. While there is no single cell surface marker exclusively expressed by hematopoietic stem cells, it generally has been accepted that human HSCs have the following antigenic profile: CD 34+, CD59+, Thy1+ (CD90), CD38low/−, C-kit−/low and, lin− (Chotinantakul, K. and Leeanansaksiri, W., Bone Marrow Research, Vol. 2012, Article ID 270425; The National Institutes of Health, Resource for Stem Cell Research, http://stemcells.nih.gov/info/scireport/pages/chapter5.aspx). CD45 is also a common marker of HSCs, except platelets and red blood cells (The National Institutes of Health, Resource for Stem Cell Research, http://stemcells.nih.gov/info/scireport/pages/chapter5.aspx). HSCs can generate a variety of cell types, including erythrocytes, neutrophils, basophils, eosinophils, platelets, mast cells, monocytes, tissue macrophages, osteoclasts, and T and B lymphocytes (Id.). The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the micro-environmental stroma and the actions of cytokines (Chotinantakul, K. and Leeanansaksiri, W., Bone Marrow Research, Vol. 2012, Article ID 270425; The National Institutes of Health, Resource for Stem Cell Research, http://stemcells.nih.gov/info/scireport/pages/chapter5.aspx).

Different paracrine factors are important in causing hematopoietic stem cells to differentiate along particular pathways. Paracrine factors involved in blood cell and lymphocyte formation (cytokines) can be made by several cell types, but they are collected and concentrated by the extracellular matrix of the stromal (mesenchymal) cells at the sites of hematopoiesis (Majumdar, M. K. et al., J. Hematother. Stem Cell Res. 2000 December; 9(6): 841-848). For example, granulocyte-macrophage colony-stimulating factor (GM-CSF) and the multilineage growth factor IL-3 both bind to the heparan sulfate glycosaminoglycan of the bone marrow stroma (Burdon, T. J., et al., Bone Marrow Research, Volume 2011, Article ID 207326; Baraniak, P. R. and McDevitt, T. C., Regen. Med. 2010 January; 5(1): 121-143). The extracellular matrix then presents these factors to the stem cells in concentrations high enough to bind to their receptors.

Mesenchymal Stem Cells (MSCs)

Mesenchymal stem cells (MSCs) (also known as bone marrow stromal stem cells or skeletal stem cells) are non-blood adult stem cells found in a variety of tissues. They are characterized by their spindle-shape morphologically; by the expression of specific markers on their cell surface; and by their ability, under appropriate conditions, to differentiate along a minimum of three lineages (osteogenic, chondrogenic, and adipogenic) (Minguell, J. J., et al., Experimental Biology and Medicine 2001, 226: 507-520; Tuan, R. S., et al., Arthritis Res. Ther. DOI: 10.1186/ar614).

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14 (Minguell, J. J., et al., Experimental Biology and Medicine 2001, 226: 507-520; Lee, H. J., et al., Arthritis & Rheumatism, Vol. 60, No. 8, August 2009, pp. 2325-2332; Kolf, C. M., et al., Arthritis Research & Therapy 2007, 9:204). As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma (Gimbel, J. M., et al., Transfus. Med. Hemother. 2008; 35: 228-238; Minguell, J. J., et al., Experimental Biology and Medicine 2001, 226: 507-520; Kolf, C. M., et al., Arthritis Research & Therapy 2007, 9:204). Studies using transgenic and knockout mice and human musculoskeletal disorders have reported that MSC differentiate into multiple lineages during embryonic development and adult homeostasis (Komine, A., et al., Biochem. Biophys. Res. Commun. 2012 Oct. 5; 426(4): 468-474; Shen, J., et al., Scientific Reports, 1:67; Reiser, J., et al., Expert. Opin. Biol. Ther. 2005 December; 5(12): 1571-1584).

Analyses of the in vitro differentiation of MSCs under appropriate conditions that recapitulate the in vivo process have led to the identification of various factors essential for stem cell commitment. Among them, secreted molecules and their receptors (e.g., transforming growth factor-β), extracellular matrix molecules (e.g., collagens and proteoglycans), the actin cytoskeleton, and intracellular transcription factors (e.g., Cbfa1/Runx2, PPAR, Sox9, and MEF2) have been shown to play important roles in driving the commitment of multipotent MSCs into specific lineages, and maintaining their differentiated phenotypes (Kolf, C. M., et al., Arthritis Research & Therapy 2007, 9:204).

For example, it has been shown that osteogenesis of MSCs, both in vitro and in vivo, involves multiple steps and the expression of various regulatory factors. During osteogenesis, multipotent MSCs undergo asymmetric division and generate osteoprecursors, which then progress to form osteoprogenitors, preosteoblasts, functional osteoblasts, and eventually osteocytes (Bennett, K. P., et al., BMC Genomics 2007, 8:380). This progression from one differentiation stage to the next is accompanied by the activation and subsequent inactivation of transcription factors, i.e., Cbfa1/Runx2, Msx2, Dlx5, Osx, and expression of bone-related marker genes, i.e., osteopontin, collagen type I, alkaline phosphatase, bone sialoprotein, and osteocalcin (Bennett, K. P., et al., BMC Genomics 2007, 8:380; Ryoo, H. M., et al., Mol. Endo. 1997, 11(11): 1681-1694; Hou, Z. et al., Proc. Natl. Acad. Sci., 96: 7294-7299, June 1999; Engler, A. J., et al., Cell 126, 677-689, Aug. 25, 2006; Marom, R. et al., Journal of Cellular Physiology 202: 41-48 (2005)).

Members of the Wnt family also have been shown to impact MSC osteogenesis. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus (Liu, G., et al., JCB, Vol. 185, No. 1, 2009, pp. 67-75). The active β-catenin/TCF/LEF complex then regulates the transcription of genes involved in cell proliferation (Novak, A. and Dedhar, S., Cell. Mol. Life Sci. 1999 Oct. 30; 56(5-6); 523-537; Grove, E. A., Genes and Development 2011 25: 1759-1762). In humans, mutations in the Wnt co-receptor, LRP5, lead to defective bone formation (Krishnan, V., et al., The Journal of Clinical Investigation, Vol. 116, No. 5, May 2006, pp. 1202-1209). "Gain of function" mutation results in high bone mass, whereas "loss of function" causes an overall loss of bone mass and strength, indicating that Wnt signaling is positively involved in embryonic osteogenesis (Krishnan, V., et al., The Journal of Clinical Investigation, 116(5), May 2006, pp. 1202-1209; Niziolek, P. J., et al., Bone 2011 November; 49(5): 1010-1019). The canonical Wnt signaling pathway also functions as a stem cell mitogen via stabilization of intracellular β-catenin and activation of the β-catenin/TCF/LEF transcription complex, resulting in activated expression of cell cycle regulatory genes, such as Myc, cyclin D1, and Msx1 (Willert, J., et al., BMC Development Biology 2002, 2:8, pp. 1-7). When MSCs are exposed to Wnt3a, a prototypic canonical Wnt signal, under standard growth medium conditions, they show markedly increased cell proliferation and a decrease in apoptosis, consistent with the mitogenic role of Wnts in hematopoietic stem cells (Almeida, M., et al., The Journal of Biological Chemistry, 280(50): 41342-41351, Dec. 16, 2005; Vijayaragavan, K., et al., Cell Stem Cell 4, 248-262, Mar. 6, 2009). However, exposure of MSCs to Wnt3a conditioned medium or overexpression of ectopic Wnt3a during osteogenic differentiation inhibits osteogenesis in vitro through β-catenin mediated down-regulation of TCF activity (Quarto, N., et al., Tissue Engineering: Part A, 16(10), 2010, pp. 3185-3197). The expression of several osteoblast specific genes, e.g., alkaline phosphatase, bone sialoprotein, and osteocalcin, is dramatically reduced, while the expression of Cbfa1/Runx2, an early osteo-inductive transcription factor is not altered, implying that Wnt3a-mediated canonical signaling pathway is necessary, but not sufficient, to completely block MSC osteogenesis (Quarto, N., et al., Tissue Engineering: Part A, 16(10), 2010, pp. 3185-3197; Eslaminejad, M. B. and Yazdi, P. E., Yakhteh Medical Journal, 9(3), Autumn 2007, pp. 158-169). On the other hand, Wnt5a, a typical non-canonical Wnt member, has been shown to promote osteogenesis in vitro (Arnsdorf, E. J., et al., PLoS ONE, April 2009, 4(4): e5388, pp. 1-10; Baksh, D., et al., J. Cell. Physiol., 2007, 212: 817-826; J. Cell. Biochem., 2007, 101: 1109-1124). Since Wnt3a promotes MSC proliferation during early osteogenesis, it is thought likely that canonical Wnt signaling functions in the initiation of early osteogenic commitment by increasing the number of osteoprecursors in the stem cell compartment, while non-canonical Wnt drives the progression of osteoprecursors to mature functional osteoblasts.

Soluble Factors

Hepatocyte Growth Factor/Scatter Factor (HGF/SF)

Hepatocyte growth factor/scatter factor (HGF/SF) is a multifunctional cytokine that promotes mitogenesis, migration, invasion and morphogenesis (Jian, W. G. and S. Hiscox, Histol. Histopathol. 2: 537-555 (1997)). HGF/SF signaling modulates integrin function by promoting aggregation and cell adhesion. Morphogenic responses to HGF/SF are dependent on adhesive events (Matsumoto, K. et al, Cancer Metastasis Rev. 14: 205-217(1995)). HGF/SF-induced effects occur via signaling of the MET tyrosine kinase receptor following ligand binding, which leads to enhanced integrin-mediated B cell and lymphoma cell adhesion (Galimi, F. et al, Stem Cells 2: 22-30 (1993); Van der Voort, R. et al., J. Exp. Med. 185: 2121-31 (1997); Weimar, I. S. et al., Blood 89: 990-1000 (1997)).

Tumor Growth Factor (Also Known as Transforming Growth Factor) (TGF)

The TGF-β1 superfamily of structurally related peptides includes the TGF-β isoforms, β1, β2, β3, and β5, the activins and the bone morphogenetic proteins (BMPs). TGF-β-like factors are a multifunctional set of conserved growth and differentiation factors that control biological processes such as embryogenesis, organogenesis, morphogenesis of tissues like bone and cartilage, vasculogenesis, wound repair and angiogenesis, hematopoiesis, and immune regulation. Signaling by ligands of the TGF-β superfamily is mediated by a high affinity, ligand-induced, heteromeric complex consisting of related Ser/Thr kinase receptors divided into two subfamilies, type I and type II. The type II receptor transphosphorylates and activates the type I receptor in a Gly/Ser-rich region. The type I receptor in turn phosphorylates and transduces signals to a novel family of recently identified downstream targets, termed Smads.

Osteoprotegerin and RANKL

The molecules osteoprotegerin (OPG) and Receptor activator of NF-κB (RANKL) play a role in the communication between osteoclasts and osteoblasts and are members of a ligand-receptor system that directly regulates osteoclast differentiation and bone resorption (Grimaud, E. et al, Am J. Pathol. 2021-2031 (2993)). RANKL has been shown to both activate mature osteoclasts and mediate osteoclastogenesis in the presence of M-CSF, i.e., RANKL is essential for osteoclast differentiation via its receptor RANK located on the osteoclast membrane. OPG is a soluble decoy receptor that prevents RANKL from binding to and activating RANK; decoy receptors recognize certain inflammatory cytokines with high affinity and specificity, but are structurally incapable of signaling or presenting the agonist to signaling receptor complexes. They therefore act as a molecular trap for the agonist and for signaling receptor components. OPG also inhibits the development of osteoclasts and down-regulates the RANKL signaling through RANK. RANKL and OPG have been detected in bone pathological situations where osteolysis occurred. The RANKL/OPG ratio is increased and correlated with markers of bone resorption, osteolytic lesions, and markers of disease activity in multiple myeloma (Id.).

Macrophage Colony-Stimulating Factor (M-CSF)

Macrophage colony-stimulating factor (M-CSF) is a hematopoietic growth factor that is involved in the proliferation, differentiation, and survival of monocytes, macrophages, and bone marrow progenitor cells (Stanley E R, et al., Mol. Reprod. Dev. 46 (1): 4-10 (1997)).

Macrophage inflammatory protein 1-alpha (MIP1α) is a member of the C—C subfamily of chemokines, a large superfamily of low-molecular weight, inducible proteins that exhibits a variety of proinflammatory activities in vitro. The C—C chemokines generally are chemotactic for cells of the monocyte lineage and lymphocytes. In addition to its proinflammatory activities, MIP1-alpha inhibits the proliferation of hematopoietic stem cells in vitro and in vivo (Cook, D. N., J. Leukocyte Biol. 59(1): 61-66 (1996)).

Sclerostin

Sclerostin, a protein expressed by osteocytes, downregulates osteoblastic bone formation by interfering with Wnt signaling.

Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. The process by which mesenchymal cells differentiate into cartilage, which is later replaced by bone cells, is called endochondral ossification.

Intramembranous Ossification

The flat bones of the scapula, the skull, and the turtle shell are formed by intramembranous ossification. In intramembranous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembranous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranous ossification involves bone morphogenetic proteins (BMPs) and the activation of a transcription factor called CBFA1. Bone morphogenetic proteins, for example, BMP2, BMP4, and BMP7, from the head epidermis, are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Paxl and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

Bone Remodeling

Bone is constantly broken down by osteoclasts and re-formed by osteoblasts in the adult. This process of renewal is known as bone remodeling. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

Lymphocytes and the Immune Response

Multicellular organisms have developed two defense mechanisms to fight infection by pathogens: innate and adaptive immune responses. Innate immune responses are triggered immediately after infection and are independent of the host's prior exposure to the pathogen. Adaptive immune responses operate later in an infection and are highly specific for the pathogen that triggered them. The function of adaptive immune responses is to destroy the invading pathogens and any toxic molecules they produce ("Chapter 24: The adaptive immune system," Molecular Biology of the Cell, Alberts, B. et al., Garland Science, NY, 2002).

The immune system consists of a wide range of distinct cell types, amongst which white blood cells called lymphocytes play a central role in determining immune specificity. Other cells, such as monocytes, macrophages, dendritic cells, Langerhans' cells, natural killer (NK) cells, mast cells, basophils, and other members of the myeloid lineage of cells, interact with the lymphocytes and play critical functions in antigen presentation and mediation of immunologic functions (Paul, W. E., "Chapter 1: The immune system: an introduction," Fundamental Immunology, 4th Edition, Ed. Paul, W. E., Lippicott-Raven Publishers, Philadelphia (1999)).

Lymphocytes are found in central lymphoid organs, the thymus, and bone marrow, where they undergo developmental steps that enable them to orchestrate immune responses. A large portion of lymphocytes and macrophages comprise a recirculating pool of cells found in the blood and lymph, providing the means to deliver immunocompetent cells to localized sites in need (Id.).

Lymphocytes are specialized cells, committed to respond to a limited set of structurally related antigens. This commitment, which exists before the first contact of the immune system with a given antigen, is expressed by the presence on the lymphocyte's surface of receptors that are specific for specific determinants or epitopes on the antigen. Each lymphocyte possesses a population of cell-surface receptors, all of which have identical combining regions. One set of lymphocyte, referenced to as a "clone", differs from another in the structure of the combining region of its receptors, and thus differs in the epitopes being recognized. The ability of an organism to respond to any non-self antigen is achieved by large numbers of different clones of lymphocytes, each bearing receptors specific for a distinct epitope (Paul, W. E., "Chapter 1: The immune system: an introduction," Fundamental Immunology, 4th Edition, Ed. Paul, W. E., Lippicott-Raven Publishers, Philadelphia (1999)).

The adaptive immune system is composed of millions of lymphocyte clones. The diversity of lymphocytes is such that even a single antigenic determinant is likely to activate many clones, each of which produces an antigen-binding site with its own characteristic affinity for the determinant ("Chapter 24: The adaptive immune system," Molecular Biology of the Cell, Alberts, B. et al., Garland Science, NY, 2002: p. 1369). When many clones are activated, such responses are said to be polyclonal; when only a few clones are activated, the response is said to be oligoclonal, and when the response involves only a single B or T cell clone, it is said to be monoclonal.

There are two broad classes of adaptive immune responses that are carried out by different classes of lymphocytes: antibody responses mediated by B-lymphocytes (or B-cells); and cell-mediated immune responses carried out by T-lymphocytes (or T-cells). B-cells are bone-marrow-derived and are precursors of immunoglobulin- (Ig-) or antibody-expressing cells, while T-cells are thymus-derived (Paul, W. E., "Chapter 1: The immune system: an introduction," Fundamental Immunology, 4th Edition, Ed. Paul, W. E., Lippicott-Raven Publishers, Philadelphia (1999)).

Primary immune responses are initiated by the encounter of an individual with a foreign antigenic substance, generally an infectious microorganism. The infected individual responds with the production of immunoglobulin (Ig) molecules specific for the antigenic determinants of the immunogen and with the expansion and differentiation of antigen-specific regulatory and effector T-lymphocytes. The latter include both T-cells that secrete cytokines as well as natural killer T-cells that are capable of lysing the cell (Id.).

As a consequence of the initial response, the immunized individual develops a state of immunologic memory. If the same (or closely related) microorganism or foreign object is encountered again, a secondary response is triggered. This generally consists of an antibody response that is more rapid and greater in magnitude than the primary (initial) response and is more effective in clearing the microbe from the body. A similar and more effective T-cell response then follows. The initial response often creates a state of immunity such that the individual is protected against a second infection, which forms the basis for immunizations (Id.).

The immune response is highly specific. Primary immunization with a given microorganism evokes antibodies and T-cells that are specific for the antigenic determinants or epitopes found on that microorganism but that usually fail to recognize (or recognize only poorly) antigenic determinants of unrelated microbes (Id.).

B-Lymphocytes

B lymphocytes are a population of cells that express clonally diverse cell surface immunoglobulin (Ig) receptors recognizing specific antigenic epitopes.

B-lymphocytes are derived from hematopoietic stem cells by a complex set of differentiation events. The molecular events through which committed early members of the B lineage develop into mature B lymphocytes occur in fetal liver, and in adult life occur principally in the bone marrow. Interaction with specialized stromal cells and their products, including cytokines, such as interleukin IL-7, are critical to the normal regulation of this process (LeBien T W, Tedder, T F. Blood (2008) 112 (5): 1570-80). The phenotype of B cells generated with fetal liver is distinct from that using comparable precursors isolated from adult bone marrow (Hardy, R R, Hayakawa, K. Ann. Rev. Immunol. (2001) 19: 595-621).

Early B-cell development is characterized by the ordered rearrangement of Ig H and L chain loci, and Ig proteins themselves play an active role in regulating B-cell development.

Pre-B cells arise from progenitor (pro-B) cells that express neither the pre-B cell receptor (pre-BCR) or surface immunoglobulin (Ig).

Plasma cells (PCs), the critical immune effector cells dedicated to secretion of antigen-specific immunoglobulin (Ig), develop at three distinct stages of antigen-driven B cell development. Short-lived plasma cells emerge in response to both T-independent (TI) and T-dependent (TD) antigens. TD antigens also induce a germinal center (GC) pathway involving somatic hypermutation, affinity maturation, and production of memory B cells and long-lived PCs. Post-GC PCs have extended half-lives, produce high affinity antibody, and reside preferentially in the bone marrow. Memory B cells rapidly expand and differentiate into PCs in response to antigen challenge (Shapiro-Shelef, et al. Immunity (2003) 19: 607-20).

Antigen-induced B-cell activation and differentiation in secondary lymphoid tissues are mediated by dynamic changes in gene expression that give rise to the germinal center (GC) reaction (see section on B-cell maturation) (LeBien T W, Tedder, T F. Blood (2008) 112 (5): 1570-80). The GC reaction is characterized by clonal expansion, class switch recombination (CSR) at the IgH locus, somatic hypermutation (SHM) of VH genes, and selection for increased affinity of a BCR for its unique antigenic epitope through affinity maturation.

Lymphocyte development requires the concerted action of a network of cytokines and transcription factors that positively and negatively regulate gene expression. Marrow stromal cell-derived interleukin-7 (IL-7) is a nonredundant cytokine for murine B-cell development that promotes V to DJ rearrangement and transmits survival/proliferation signals.

FMS-like receptor tyrosine kinase-3 (FLT-3)-ligand and thymic stromal lymphopoietin (TSLP) play important roles in fetal B-cell development.

The cytokine(s) that regulate human B-cell development are not as well understood, and the cytokine (or cytokines)

that promote marrow B-cell development at all stages of human life remains unknown.

At least 10 distinct transcription factors regulate the early stages of B-cell development, with E2A, EBF, and Pax5 being particularly important in promoting B-lineage commitment and differentiation.

Pax5, originally characterized by its capacity to bind to promoter sequences in Ig loci, may be the most multifunctional transcription factor for B cells. Pax5-deficient pro-B cells harbor the capacity to adapt non-B-lineage fates and develop into other hematopoietic lineages (Nutt S L, et al., Nature. 1999; 401: 556-562). Pax5 also regulates expression of at least 170 genes, a significant number of them important for B-cell signaling, adhesion, and migration of mature B cells (Cobaleda C, et al., Nat Immunol. 2007; 8: 463-470). Conditional Pax5 deletion in mature murine B cells can result in dedifferentiation to an uncommitted hematopoietic progenitor and subsequent differentiation into T-lineage cells under certain conditions (Cobaleda C, et al., Nature. 2007; 449: 473-477).

B lymphocyte induced maturation protein (Blimp-1), a transcriptional repressor, a 98 kDa protein containing five zinc finger motifs, has been implicated in plasma cell differentiation, and is required for the complete development of the pre-plasma memory B cell compartment (Shapiro-Shelef, et al. Immunity (2003) 19: 607-20).

B Cell Specific Cell Surface Molecules

Table 1 shows cell surface CD molecules that are preferentially expressed by B cells (LeBien T W, Tedder, T F. Blood (2008) 112 (5): 1570-80).

TABLE 1

| Name | Original name | Cellular Reactivity | Structure |
|---|---|---|---|
| CD19 | B4 | Pan-B cell, follicular dendritic cells | Ig superfamily |
| CD20 | B1 | Mature B cells | MS4A family |
| CD21 | B2, HB-5 | Mature B cells, FDCs | Complement receptor family |
| CD22 | BL-CAM, Lyb-8 | Mature B cells | Ig superfamily |
| CD23 | FcεRII | Activated B cells, FDCs, others | C-type lectin |
| CD24 | BA-1, HB-6 | Pen-B cell, granulocytes, epithelial cells | GPI anchored |
| CD40 | Bp50 | B cells, epithelial cells, FDCs, others | TNF receptor |
| CD72 | Lyb-2 | Pam-B cell | C-type lectin |
| CD79 a, b | Igε,β | Surface Ig+ B cells | Ig superfamily |

CD19 is expressed by essentially all B-lineage cells and regulates intracellular signal transduction by amplifying Src-family kinase activity.

CD20 is a mature B cell-specific molecule that functions as a membrane-embedded Ca2+ channel. Ritixumab, the first mAb approved by the Food and Drug Administration (FDA) for clinical use in cancer therapy (e.g., follicular lymphoma), is a chimeric CD20 mAb.

CD21 is a C3d and Epstein-Barr virus receptor that interacts with CD19 to generate transmembrane signals and inform the B cell of inflammatory responses within microenvironments.

CD22 functions as a mammalian lectin for α2,6-linked sialic acid that regulates follicular B-cell survival and negatively regulates signaling.

CD23 is a low-affinity receptor for IgE expressed on activated B cells that influences IgE production.

CD24 was among the first pan-B-cell molecules to be identified, but this GPI-anchored glycoprotein's function remains unknown.

CD40 serves as a critical survival factor for GC B cells and is the ligand for CD154 expressed by T cells.

CD72 functions as a negative regulator of signal transduction and as the B-cell ligand for Semaphorin 4D (CD100).

There may be other unidentified molecules preferentially expressed by B cells, but the cell surface landscape is likely dominated by molecules shared with multiple leukocyte lineages.

B-Cell Maturation and Subset Development

Outside the marrow, B cells are morphologically homogenous, but their cell surface phenotypes, anatomic localization, and functional properties reveal still-unfolding complexities. Immature B cells exiting the marrow acquire cell surface IgD as well as CD21 and CD22, with functionally important density changes in other receptors. Immature B cells are also referred to as "transitional" (T1 and T2) based on their phenotypes and ontogeny, and have been characterized primarily in the mouse (Chung J B, et al., Trends Immunol. 2003; 24: 343-349). Immature B cells respond to T cell-independent type 1 antigens such as lipopolysaccharides, which elicit rapid antibody responses in the absence of MHC class II-restricted T-cell help (Coutinho A, Moller G. Adv Immunol. 1975; 21: 113-236). The majority of mature B cells outside of gut associated lymphoid tissue (GALT) reside within lymphoid follicles of the spleen and lymph nodes, where they encounter and respond to T cell-dependent foreign antigens bound to follicular dendritic cells (DCs), proliferate, and either differentiate into plasma cells or enter GC reactions.

Germinal centers (GCs) (meaning sites within lymphoid tissue that are more active in lymphocyte proliferation than are other parts of the lymphoid tissue, containing rapidly proliferating cells (i.e., centroblasts)) are the main site for high-affinity antibody-secreting plasma cell and memory B-cell generation (Jacob J, et al., Nature. 1991; 354: 389-392). Within GCs, somatic hypermutation (SHM) and purifying selection produce the higher affinity B-cell clones that form the memory compartments of humoral immunity (Jacob J, et al. Nature. 1991; 354: 389-392; Kelsoe G., Immunity. 1996; 4: 107-111). Affinity maturation in GCs does not represent an intrinsic requirement for BCR signal strength but rather a local, Darwinian competition. The dynamics of lymphocyte entry into follicles and their selection for migration into and within GCs represents a complex ballet of molecular interactions orchestrated by chemotactic gradients and B-cell receptor (BCR) engagement that is only now being elucidated (Allen C D, et al. Immunity. 2007; 27: 190-202).

B-cell subsets with individualized functions such as B-1 and marginal zone (MZ, referring to the junction of the lymphoid tissue of a lymphatic nodule with the surrounding nonlymphoid red pulp of the spleen) B cells have also been identified. Murine B-1 cells are a unique CD5+ B-cell subpopulation (Hayakawa K, et al. J Exp Med. 1983; 157: 202-218) distinguished from conventional B (B-2) cells by their phenotype, anatomic localization, self-renewing capacity, and production of natural antibodies (Hardy R R, Hayakawa K., Annu Rev Immunol. 2001; 19: 595-621). Peritoneal B-1 cells are further subdivided into the B-1a (CD5+) and B-1b (CD5−) subsets. Their origins, and whether they derive from the same or distinct progenitors compared with B-2 cells, have been controversial (Dorshkind K, Montecino-Rodriguez E., Nat Rev Immunol. 2007; 7: 213-219). However, a B-1 progenitor that appears distinct from a B-lineage progenitor that develops primarily into the B-2 population has been identified in murine fetal marrow, and to a lesser degree in adult marrow (Montecino-Rodriguez E, Leathers H, Dorshkind K., Nat Immunol. 2006; 7: 293-301). B-1a cells and their natural antibody products provide innate protection against bacterial infections in naive hosts, while B-1b cells function independently as the primary source of long-term adaptive antibody responses to polysaccharides and other T cell-independent type 2 antigens during infection (Id.). The function and potential subpopulation status of human B-1 cells is less understood (Dorshkind K, Montecino-Rodriguez E., Nat Rev Immunol. 2007; 7: 213-219). MZ B cells are a unique population of murine splenic B cells with attributes of naive and memory B cells (Pillai S, Cariappa A, Moran S T., Annu Rev Immunol. 2005; 23: 161-196), and constitute a first line of defense against blood-borne encapsulated bacteria. Uncertainty regarding the identity of human MZ B cells partially reflects the fact that the microscopic anatomy of the human splenic MZ differs from rodents (Steiniger B, et al. Histochem Cell Biol. 2006; 126: 641-648). Likewise, the microscopic anatomy of human follicular mantle zones is not recapitulated in mouse spleen and lymph nodes.

The B1, MZ, and GC B-cell subsets all contribute to the circulating natural antibody pool, thymic-independent IgM antibody responses, and adaptive immunity by terminal differentiation into plasma cells, the effector cells of humoral immunity (Radbruch A, et al., Nat Rev Immunol. 2006; 6: 741-750). Antigen activation of mature B cells leads initially to GC development, the transient generation of plasmablasts that secrete antibody while still dividing, and short-lived extrafollicular plasma cells that secrete antigen-specific germ line-encoded antibodies. GC-derived memory B cells generated during the second week of primary antibody responses express mutated BCRs with enhanced affinities, the product of SHM. Memory B cells persist after antigen challenge, rapidly expand during secondary responses, and can terminally differentiate into antibody-secreting plasma cells. In a manner similar to the early stages of B-cell development in fetal liver and adult marrow, plasma cell development is tightly regulated by a panoply of transcription factors, most notably Bcl-6 and Blimp-1 (Shapiro-Shelef M, Calame K., Nat Rev Immunol. 2005; 5: 230-242).

Persistent antigen-specific antibody titers derive primarily from long-lived plasma cells (Radbruch A, et al., Nat Rev Immunol. 2006; 6: 741-750). Primary and secondary immune responses generate separate pools of long-lived plasma cells in the spleen, which migrate to the marrow where they occupy essential survival niches and can persist for the life of the animal without the need for self-replenishment or turnover (Radbruch A, et al., Nat Rev Immunol. 2006; 6: 741-750; McHeyzer-Williams L J, McHeyzer-Williams M G., Annu Rev Immunol. 2005; 23: 487-513). The marrow plasma cell pool does not require ongoing contributions from the memory B-cell pool for its maintenance, but when depleted, plasma cells are replenished from the pool of memory B cells (Dilillo D J, et al., J Immunol. 2008; 180: 361-371). Thereby, persisting antigen, cytokines, or Toll-like receptor signals may drive the memory B-cell pool to chronically differentiate into long-lived plasma cells for long-lived antibody production.

In addition to their essential role in humoral immunity, B cells also mediate/regulate many other functions essential for immune homeostasis. B cells are required for the initiation of T-cell immune responses, as first demonstrated in mice depleted of B cells at birth using anti-IgM antiserum (Ron Y, et al., Eur J Immunol. 1981; 11: 964-968). However, this has not been without controversy, as an absence of B cells impairs CD4 T-cell priming in some studies, but not others. Nonetheless, antigen-specific interactions between B and T cells may require the antigen to be first internalized by the BCR, processed, and then presented in an MHC-restricted manner to T cells (Ron Y, Sprent J., J Immunol. 1987; 138: 2848-2856; Janeway C A, et al., J Immunol. 1987; 138: 1051-1055; Lanzavecchia A., Nature. 1985; 314: 537-539).

B-Cell Abnormalities

The normal B-cell developmental stages have malignant counterparts that reflect the expansion of a dominant subclone leading to development of leukemia and lymphoma.

For example, non-T, non-B ALL is a malignancy of B-cell precursors (Korsmeyer S J, et al., J Clin Invest. 1983; 71: 301-313). The antiapoptotic Bcl-2 gene was discovered as the translocation partner with the IgH locus in the t(14;18) (q32;q21); frequently occurring in follicular lymphoma (Tsujimoto Y, et al., Science. 1984; 226: 1097-1099). A substantial number of cases of diffuse large B-cell lymphoma exhibit dysregulated expression of the transcriptional repressor Bcl-6 (Ye B H, et al., Science. 1993; 262: 747-750). The Hodgkin/Reed-Sternberg cell in Hodgkin lymphoma is of B-lymphocyte origin based on the demonstration of clonal Ig gene rearrangements (Kuppers R, et al., Proc Natl Acad Sci USA. 1994; 91: 10962-10966).

The monoclonal gammopathies (paraproteinemias or dysproteinemias) are a group of disorders characterized by the proliferation of a single clone of plasma cells which produces an immunologically homogeneous protein commonly referred to as a paraprotein or monoclonal protein (M-protein, where the "M" stands for monoclonal). Each serum M-protein consists of two heavy polypeptide chains of the same class designated by a capital letter and a corresponding Greek letters: Gamma ($\gamma$) in IgG, Alpha ($\alpha$) in IgA, Mu ($\mu$) in IgM, Delta ($\delta$) in IgD, Epsilon ($\epsilon$) in IgE. For example, basophils in IgE myeloma are characterized by a higher expression of high affinity IgE receptor relative to normal controls.

Multiple Myeloma

Multiple myeloma (MM), a B cell malignancy characterized by the accumulation of plasma cells in the BM and the secretion of large amounts of monoclonal antibodies that ultimately causes bone lesions, hypercalcemia, renal disease, anemia, and immunodeficiency (Raab M S, et al., Lancet 2009; 374: 324-39), is the second most frequent blood disease in the United States, affecting 7.1 per 100,000 men and 4.6 per 100,000 women.

MM is characterized by monoclonal proliferation of malignant plasma cells (PCs) in the bone marrow (BM), the presence of high levels of monoclonal serum antibody, the development of osteolytic bone lesions, and the induction of angiogenesis, neutropenia, amyloidosis, and hypercalcemia (Vanderkerken K, et al., Immunol Rev 2003; 194: 196-206; Raab M S, et al., Lancet 2009; 374: 324-39). MM is seen as a multistep transformation process (Pratt G. J Clin Pathol: Molec Pathol. (2002) 55: 273-83). Although little is known about the immortalizing and initial transforming events, the initial event is thought to be the immortalization of a plasma cell to form a clone, which may be quiescent, non-accumulating and not cause end organ damage due to accumulation of plasma cells within the bone marrow (monoclonal gammopathy of undetermined significance, or MGUS). Smouldering MM (SMM) also has no detectable end-organ damage, but differs from MGUS by having a serum mIg level higher than 3 g/dl or a BM PC content of more than 10% and an average rate of progression to symptomatic MM of 10% per year. Currently there are no tests that measure phenotypic or genotypic markers on tumor cells that predict progression (Kuehl, W M, Bergsagel, P L. J Clin Invest. (2012) 122 (10): 3456-63). An abnormal immunophenotype distinguishes healthy plasma cells (PCs) from tumor cells. Healthy BM PCs are CD38+CD138+CD19+CD45+CD56− (Id.). Although MM tumor cells also are CD38+CD138+, 90% are CD19−, 99% are CD45− or CD45 lo, and 70% are CD56+ (Id.).

The prognosis and treatment of this disease has greatly evolved over the past decade due to the incorporation of new agents that act as immunomodulators and proteasome inhibitors. Despite recent progress with a number of novel treatments (Raab M S, et al., Lancet 2009; 374: 324-39; Schwartz R N, Vozniak M., J Manag Care Pharm 2008; 14: 12-9), patients only experience somewhat longer periods of remission. Because of the development of drug resistance or relapse, MM is an incurable disease (Schwartz R N, Vozniak M., J Manag Care Pharm 2008; 14: 12-9; Kyle R A., Blood 2008; 111: 4417-8), with a median survival time of 3-4 years.

Disease management is currently tailored based on the patient's co-morbidity factors and stage of disease (for a complete list of treatments and their implementation, see Raab M S, et al., Lancet 2009; 374: 324-39 and Schwartz R N, Vozniak M., J Manag Care Pharm 2008; 14: 12-9).

Allogeneic blood and marrow transplantation (allo-BMT) is an effective immunotherapeutic treatment that can provide partial or complete remission for patients with drug-resistant hematological malignancies, including multiple myeloma.

Staging of Myeloma

While multiple myeloma may be staged using the Durie-Salmon system, its value is becoming limited because of newer diagnostic methods. The International Staging System for Multiple Myeloma relies mainly on levels of albumin and beta-2-microglobulin in the blood. Other factors that may be important are kidney function, platelet count and the patient's age (www.cancer.org/cancer/multiplemyelomaldetailedguide/multiple-myeloma-staging, last revised Feb. 12, 2013).

The Durie-Salmon staging system is based on 4 factors:
1. The amount of abnormal monoclonal immunoglobulin in the blood or urine: Large amounts of monoclonal immunoglobulin indicate that many malignant plasma cells are present and are producing that abnormal protein.
2. The amount of calcium in the blood: High blood calcium levels can be related to advanced bone damage. Because bone normally contains lots of calcium, bone destruction releases calcium into the blood.
3. The severity of bone damage based on x-rays: Multiple areas of bone damage seen on x-rays indicate an advanced stage of multiple myeloma.
4. The amount of hemoglobin in the blood: Hemoglobin carries oxygen in red blood cells. Low hemoglobin levels mean that the patient is anemic; it can indicate that the myeloma cells occupy much of the bone marrow and that not enough space is left for the normal marrow cells to make enough red blood cells.

This system uses these factors to divide myeloma into 3 stages. Stage I indicates the smallest amount of tumor, and stage III indicates the largest amount of tumor:

In Stage I, a relatively small number of myeloma cells are found. All of the following features must be present:
i. Hemoglobin level is only slightly below normal (still above 10 g/dL)
ii. Bone x-rays appear normal or show only 1 area of bone damage
iii. Calcium levels in the blood are normal (less than 12 mg/dL)
iv. Only a relatively small amount of monoclonal immunoglobulin is in blood or urine In Stage II, a moderate number of myeloma cells are present. Features are between stage I and stage III.

In Stage III, a large number of myeloma cells are found. One or more of the following features must be present:
i. Low hemoglobin level (below 8.5 g/dL)
ii. High blood calcium level (above 12 mg/dL)
iii. 3 or more areas of bone destroyed by the cancer
iv. Large amount of monoclonal immunoglobulin in blood or urine The International Staging System divides myeloma into 3 stages based only on the serum beta-2 microglobulin and serum albumin levels.

In Stage I, serum beta-2 microglobulin is less than 3.5 (mg/L) and the albumin level is above 3.5 (g/L). Stage II is neither stage I nor III, meaning that either: the beta-2 microglobulin level is between 3.5 and 5.5 (with any albumin level), OR the albumin is below 3.5 while the beta-2 microglobulin is less than 3.5. In Stage III, Serum beta-2 microglobulin is greater than 5.5.

Factors other than stage that affect survival include kidney function (when the kidneys are damaged by the monoclonal immunoglobulin, blood creatinine levels rise, predicting a worse outlook); age (in the studies of the international staging system, older people with myeloma do not live as long); the myeloma labeling index (sometimes called the plasma cell labeling index), which indicates how fast the cancer cells are growing—a high labeling index can predict a more rapid accumulation of cancer cells and a worse outlook; and chromosome studies, i.e., certain chromosome changes in the malignant cells can indicate a poorer outlook. For example, changes in chromosome 13 will lower a person's chances for survival. Another genetic abnormality that predicts a poor outcome is a translocation (meaning an exchange of material) from chromosomes 4 and 14.

Biological pharmacotherapy for the treatment of MM currently includes immunomodulatory agents, such as thalidomide or its analogue, lenalidomide, and bortezomib, a first-in-class proteosome inhibitor. Unfortunately, some side effects associated with these therapies such as peripheral neuropathy and thrombocytopenia (in the case of bortezomib) restrict dosing and duration of treatment (Raab M S, et al., Lancet 2009; 374: 324-39; Schwartz R N, Vozniak M., J Manag Care Pharm 2008; 14: 12-9; Field-Smith A, et al., Ther Clin Risk Manag 2006; 2: 271-9).

Despite significant advances in the implementation of these drugs, MM still remains a lethal disease for the vast majority of patients. Since MM is a disease characterized by multiple relapses, the order/sequencing of the different effective treatment options is crucial to the outcome of MM patients. In the frontline setting, the first remission is likely to be the period during which patients will enjoy the best quality of life. Thus, one goal is to achieve a first remission that is the longest possible by using the most effective treatment upfront. At relapse, the challenge is to select the optimal treatment for each patient while balancing efficacy and toxicity. The decision will depend on both disease- and patient-related factors (Mohty B, et al., Leukemia 2012; 26: 73-85). Thus, having the capability of testing the efficacy of a potential therapy, prior to patient treatment, can have a major impact in the management of this disease.

As opposed to other hematological malignancies, MM as well as other cancers that metastasize to the BM strongly interact with the BM microenvironment, which is composed of endothelial cells, stromal cells, osteoclasts (OCL), osteoblasts (OSB), immune cells, fat cells and the extracellular matrix (ECM). These interactions are responsible for the specific homing in the BM, the proliferation and survival of the MM cells, the resistance of MM cells to drug treatment, and the development of osteolysis, immunodeficiency, and anemia (Dvorak H F, et al., J Surg Oncol 2011; 103: 468-74; De Raeve H R, Vanderkerken K., Histol Histopathol 2005; 20: 1227-50; Fowler J A, et al., Bone 2011; 48: 121-8; Fowler J A, et al., Cancer Res 2012; Roodman G D., J Bone Miner Res 2002; 17: 1921-5).

The Bone Marrow Niche and MM Progression

The BM niche plays a key role in MM-related bone disease. A complex interaction with the BM microenvironment in areas adjacent to tumor foci, characterized by activation of osteoclasts and suppression of osteoblasts, leads to lytic bone disease (Kuehl, W M, Bergsagel, P L. J Clin Invest. (2012) 122 (10): 3456-63; Yaccoby, S. Br J Haematol. (2010) 149 (3): 311-321). Thus, although the MM microenvironment is highly complex, it is understood that suppression of OSB activity plays a key role in the bone destructive process as well as progression of the tumor burden (Roodman G D., Bone 2011; 48: 135-40). Treatments that target both the bone microenvironment as well as the tumor, such as bortezomib and immunomodulatory drugs, have been more effective than prior therapies for MM and have dramatically increased both progression-free survival and overall survival of patients.

MM cells closely interact with the BM microenvironment, also termed the cancer niche. The elements of the bone marrow niche can provide an optimal growth environment for multiple hematological malignancies including multiple myeloma (MM). MM cells convert the bone marrow into a specialized neoplastic niche, which aids the growth and spreading of tumor cells by a complex interplay of cytokines, chemokines, proteolytic enzymes and adhesion molecules. Moreover, the MM BM microenvironment confers survival and chemoresistance of MM cells to current therapies.

Bone Marrow Stromal Cells (BMSCs)

Multiple myeloma (MM) cells adhere to BMSCs and ECM. Tumor cells, such as MM cells, bind to ECM proteins, such as type I collagen and fibronectin via syndecan 1 and very late antigen 4 (VLA-4) on MM cells and to BMSC VCAM-1 via VLA-4 on MM cells. Adhesion of MM cells to BMSC activates many pathways resulting in upregulation of cell cycle regulating proteins and antiapoptotic proteins (Hideshima T, et al., Blood. 2004; 104(3): 607-618). The interaction between MM cells and BMSCs triggers NF-κB signaling pathway and interleukin-6 (IL-6) secretion in BMSCs. In turn, IL-6 enhances the production and secretion of VEGF by MM cells. The existence of this paracrine loop optimizes the BM milieu for MM tumor cell growth (Kumar S, et al., Leukemia. 2003; 17(10): 2025-2031). BMSC-MM cell interaction is also mediated through Notch. The Notch-signaling pathways, both in MM cells as well as in BMSC, promote the induction of IL-6, vascular endothelial growth factor (VEGF), and insulin-like growth factor (IGF-1) secretion and is associated with MM cell proliferation and survival (Radtke F, Raj K. Nature Reviews Cancer. 2003; 3(10): 756-767; Nefedova Y, et al., Blood. 2004; 103(9): 3503-3510). It has been shown that BMSC from MM patients express several proangiogenic molecules, such as VEGF, basic-fibroblast growth factor (bFGF), angiopoietin 1 (Ang-1), transforming growth factor (TGF)-β, platelet-derived growth factor (PDGF), hepatocyte growth factor (HGF) and interleukin-1 (IL-1) (Giuliani N, et al., Cancer Microenvironment. 2011; 4(3): 325-337). BMSCs from MM patients also have been shown to release exosomes, which are transferred to MM cells, thereby resulting in modulation of tumor growth in vivo, mediated by specific miRNA (Roccaro A M, et al., Blood. 2011; 118, abstract 625 ASH Annual Meeting Abstracts).

Endothelial Cells (ECs) and Angiogenesis

BM angiogenesis represents a constant hallmark of MM progression, partly driven by release of pro-angiogenic cytokines from the tumor plasma cells, BMSC, and osteoclasts, such as VEGF, bFGF, and metalloproteinases (MMPs). The adhesion between MM cells and BMSCs upregulates many cytokines with angiogenic activity, most notably VEGF and bFGF (Podar K, Anderson K C. Blood. 2005; 105(4): 1383-1395). In MM cells, these pro-angiogenic factors may also be produced constitutively as a result of oncogene activation and/or genetic mutations (Rajkumar S V, Witzig T E. Cancer Treatment Reviews 2000; 26(5): 351-362). Evidence for the importance of angiogenesis in the pathogenesis of MM was obtained from BM samples from MM patients (Kumar S, et al., Bone Marrow Transplantation. 2004; 34(3): 235-239). The level of BM angiogenesis, as assessed by grading and/or microvessel density (MVD), is increased in patients with active MM as compared to those with inactive disease or monoclonal gammopathy of undetermined significance (MGUS), a less advanced plasma cell disorder. Comparative gene expression profiling of multiple myeloma endothelial cells and MGUS endothelial cells has been performed in order to determine a genetic signature and to identify vascular mechanisms governing the malignant progression (Ria R, et al., Clinical Cancer Research. 2009; 15(17): 5369-5378). Twenty-two genes were found differentially expressed at relatively high stringency in MM endothelial cells compared with MGUS endothelial cells. Functional annotation revealed a role of these genes in the regulation of ECM formation and bone remodeling, cell adhesion, chemotaxis, angiogenesis, resistance to apoptosis, and cell-cycle regulation. The distinct endothelial cell gene expression profiles and vascular phenotypes detected may influence remodeling of the bone marrow microenvironment in patients with active multiple myeloma. Overall, this evidence suggests that ECs present with functional, genetic, and morphologic features indicating their ability to induce BM neovascularization, resulting in MM cell growth, and disease progression.

Osteoclasts

The usual balance between bone resorption and new bone formation is lost in many cases of MM, resulting in bone destruction and the development of osteolytic lesions (Bataille R, et al., Journal of Clinical Oncology. 1989; 7(12): 1909-1914). Bone destruction develops adjacent to MM cells, yet not in areas of normal bone marrow. There are several factors implicated in osteoclast activation, including receptor activator of NF-κB ligand (RANKL), macrophage inflammatory protein-1a (MIP-1a), interleukin-3 (IL-3), and IL-6 (Roodman G D., Leukemia. 2009; 23(3): 435-441). RANK ligand (RANKL) is a member of the tumor necrosis factor (TNF) family and plays a major role in the increased osteoclastogenesis implicated in MM bone disease. RANK is a transmembrane signaling receptor expressed by osteoclast cells. MM cell binding to neighboring BMSC within the bone marrow results in increased RANKL expression. This leads to an increase in osteoclast activity through the binding of RANKL to its receptor on osteoclast precursor cells, which further promotes their differentiation through NF-κB and JunN-terminal kinase pathway (Ehrlich L A, Roodman G D. Immunological Reviews. 2005; 208: 252-266). RANKL is also involved in inhibition of osteoclast apoptosis. Blocking RANKL with a soluble form of RANK has been shown to modulate not only bone loss but also tumor burden in MM in vivo models (Yaccoby S, et al. British Journal of Haematology. 2002; 116(2): 278-290). Moreover, osteoclasts constitutively secrete proangiogenic factors (e.g. osteopontin) that enhance vascular tubule formation (Tanaka Y, et al. Clinical Cancer Research. 2007; 13(3): 816-823).

Osteoblasts in MM Progression

Osteoblasts are thought to contribute to MM pathogenesis by supporting MM cell growth and survival (Karadag A, et al. British Journal of Haematology. 2000; 108(2): 383-390). This could potentially result from the ability of osteoblasts to secrete IL-6 in a co-culture system with MM cells, thus increasing IL-6 levels within the BM milieu and inducing MM plasma cell growth. Other mechanisms include the possible role of osteoblasts in stimulating MM cell survival by blocking TRAIL-mediated programmed MM cell death, by secreting osteoprotegerin (OPG), a receptor for both RANKL and TRAIL (Shipman C M, Croucher P I. Cancer Research. 2003; 63(5): 912-916). In addition, suppression of osteoblast activity is responsible for both the bone destructive process and progression of myeloma tumor burden. Several factors have been implicated in the suppression of osteoblast activity in MM, including DKK1 (Tian E, et al., The New England Journal of Medicine. 2003; 349(26): 2483-2494). DKK1 is a Wnt-signaling antagonist secreted by MM cells that inhibits osteoblast differentiation. DKK1 is significantly overexpressed in patients with MM who present with lytic bone lesions. Myeloma-derived DKK1 also disrupts Wnt-regulated OPG and RANKL production by osteoblasts. Studies have shown that blocking DKK1 and activating Wnt signaling prevents bone disease in MM and is associated with a reduction in tumor burden (Yaccoby S, et al. Blood. 2007; 109(5): 2106-2111; Edwards C M, et al. Blood. 2008; 111(5): 2833-2842; Fulciniti M, et al. Blood. 2009; 114(2): 371-379).

Many components of the microenvironment support the propagation of MM cells through cell-cell adhesion and the release of growth factors such as interleukin-6 (IL-6) and insulin-like growth factor-1 (IGF-1) (Deleu S, et al. Leukemia 2009; 23: 1894-903; Field-Smith A, et al. Ther Clin Risk Manag 2006; 2: 271-9; D'Souza S, et al. Blood 2011; 118: 6871-80). Survival and drug resistance of malignant cells is associated with their ability to shape the local microenvironment, in part by disrupting the balance of pro- and anti-angiogenic factors through neovascularization (Otjacques E, et al. Int J Hematol 2011; 94: 505-18) and bone remodeling which leads to osteolysis (Raje N, Roodman G D. Clin Cancer Res 2011; 17: 1278-86; Giuliani N, et al. Blood 2006; 108: 3992-6; Lentzsch S, et al. Hematol Oncol Clin North Am 2007; 21: 1035-49, viii).

Unfortunately, primary MM tumor cells have been difficult to propagate ex vivo because they require a microenvironment hard to reproduce in vitro. MM cells grown in vitro therefore are very short lived and grow poorly outside their BM milieu, and attempts to optimize their maintenance have been hampered by a lack of known conditions that allow for their ex vivo survival (Zlei M, et al. Exp Hematol 2007; 35: 1550-61). Aside from various xenograft models (Calimeri T, et al. Leukemia 2011; 25: 707-11; Yata K, Yaccoby S. Leukemia 2004; 18: 1891-7; Yaccoby S, et al. Blood 2002; 100: 4162-8; Bell E., Nature Reviews Immunology 2006; 6: 87), only one group to date has reported on creating an in vitro model capable of supporting the proliferation and survival of MM cells (Kirshner J, et al., Blood 2008; 112: 2935-45). However, the macroscale static methodology that was employed has limited value as, inter alia, it fails to recapitulate the spatial and temporal characteristics of the complex tumor niche.

Although microphysiologically relevant human three dimensional (3D) tissue and tumor models cannot replicate the biological and physiological complexity associated with homeostatic and disease progressions that occur over a long period of time, such models may provide "snapshot" ex vivo reproductions of authentic phenotypic cell functions and interactions relating to specific persons and disease states.

It is well recognized that serially cultured human diploid cells have a finite lifetime in vitro (Hayflick, L. Exptl Cell Res. (1965) 37: 614-636). After a period of active multiplication, generally less than one year, these cells demonstrate an increased generation time, gradual cessation of mitotic activity, accumulation of cellular debris, and, ultimately, total degeneration of the culture (Id.). However, conventional practices of immortalizing human cells into cell lines by gene transfection perturbs the cells' gene expression profiles, cellular physiology and physical integrity of their genome. Even if primary cells can be grown and maintained, gene expression and cellular physiology of such cells can be fundamentally different in 2D versus 3D culture environments.

Recently, major efforts have been made to develop in vitro MM models for drug evaluation (Jakubikova, J, et al. Oncotarget, 2016, 7: 77326-77341; Braham, M V J, et al. Tissue Eng. Part C Methods, 2018, 24: 300-312; Kirshner, J, et al. Blood, 2008, 112: 2935-2945; Silva, A, et al. Cancer Res., 2017, 77: 3336-3351; Reagan, M R, et al. Blood, 2014, 124: 3250-3259; De La Puente, P, et al. Biomaterials, 2015, 73: 70-84; de Groot, T E, et al. Lab Chip, 2016, 16: 334-44; Pak, C, et al. Integr. Biol., 2015, 7: 643-654; Khin, Z P, et al. Cancer Res., 2014, 74: 56-67; Waldschmidt, J, et al. Clin. Lymphoma, Myeloma Leuk., 2015, 15: e224-e225). Of note, 3D engineered hydrogel with stromal cells was commonly used as biomimetic scaffolds for patient-derived MM cells (PMMC), e.g., fibrin gel with endothelial cells and bone marrow stromal cells (De La Puente, P, et al. Biomaterials, 2015, 73: 70-84), hydrogel modified by mesenchymal stem cells (Jakubikova, J, et al. Oncotarget, 2016, 7: 77326-77341), and collagen type I with bone marrow stromal cells (Silva, A, et al. Cancer Res., 2017, 77: 3336-3351). Also, microfluidic culture devices were used to apply shear flow and enable the viability of PMMC (de Groot, T E, et al. Lab Chip, 2016, 16: 334-44; Pak, C, et al. Integr. Biol., 2015, 7: 643-654). These studies suggested that replicating physiologic relevant bone marrow micro-environments is critical for in vitro PMMC maintenance.

The described invention provides a 96-well plate based pumpless culture platform for high-throughput drug evaluation of multicellular cultures. The culture platform was designed, fabricated, and evaluated to: (1) control and maintain flow rate within 10% under the gravity-based pumpless configuration, necessary for osteoblastic stimulation while eliminating potential sources for leaking and bubble formation, and (2) demonstrate high-throughput in situ cell staining and imaging using high content screening (HCS) for drug response evaluation of multicellular cultures.

SUMMARY OF THE INVENTION

According to one aspect, the described invention provides an in vitro multiwell plate-based pumpless perfusion culture device comprising, from top to bottom: (i) a bottomless multi-well plate comprising a plurality of bottomless wells, wherein four adjacent sequential wells comprise a culture chamber; (ii) a first micropatterned pressure-sensitive adhesive (PSA) layer attached to a bottom surface of the culture chamber; (iii) a polymer layer comprising four holes vertically aligned with the four adjacent sequential wells of the culture chamber, the polymer layer being attached to a bottom surface of the first micropatterned PSA layer; (iv) a second micropatterned PSA layer attached to a bottom surface of the polymer layer; (v) a third micropatterned PSA layer that connects the four adjacent sequential wells, wherein the third micropatterned PSA layer is attached to a bottom surface of the second micropatterned PSA layer; (vi) a transparent, optical grade glass layer attached to the bottom surface of the third micropatterned PSA layer that forms a bottom surface for the plurality of wells and that seals the multi-well plate-based pumpless perfusion culture device; (vii) a rocking platform for holding the multi-well plate, characterized by rocking speed and an adjustable rocking/tilt angle; wherein the four adjacent sequential wells that comprise the culture chamber comprise an inlet well, a cell seeding port well, a cell chamber well, and an outlet well; wherein the first micropatterned PSA layer is effective to maintain stable liquid droplets and to prevent medium evaporation by covering the inlet well, cell seeding port well, and outlet well of the first polymer layer; wherein the inlet and outlet wells are configured as reservoirs for culture medium and to generate hydrostatic pressure differential between the wells; wherein the cell seeding port well is adapted to receive a biological sample of cells; wherein a first polymer membrane between the second micropatterned PSA layer and third micropatterned PSA layer is effective to cover the inlet well and to control the flow rate of medium in the culture chamber; wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber. According to one embodiment, the polymer layer comprises polydimethylsiloxane (PDMS). According to another embodiment, the first polymer membrane comprises polycarbonate (PCTE). According to another embodiment, the first polymer membrane is characterized by a diameter of about 0.4 µm, a porosity of about 10%, and a thickness of about 10 µm. According to another embodiment, the second polymer membrane comprises polyester. According to another embodiment, the second polymer membrane is characterized by a diameter of about 0.4 µm and a thickness of about 12 µm. According to another embodiment, the cell chamber well is connected to the cell seeding port well by a microchannel. According to another embodiment, the rocking platform is configured to maintain a medium flow rate of about 0.46 to about 5 µL/min. According to another embodiment, the device is configured to maintain a flow-induced shear stress of about 0.4 mPa.

According to another aspect, the described invention provides an ex vivo multiple myeloma (MM) cancer niche contained in a device in which flow of minute amounts of liquids or dissolved gas molecules, is controlled by microfluidics (microfluidic device) comprising: (a) an ex vivo bone marrow microenvironment perfused by nutrients and dissolved gas molecules (bone marrow niche) comprising viable osteoblasts seeded on a surface of the microfluidic device and cultured to form 3D nodular structures that comprise a 3D bone-like tissue, the 3D bone-like tissue being characterized by an extracellular matrix secreted by the viable osteoblasts; and (b) a multiple myeloma tumor biospecimen comprising viable human multiple myeloma cells; the microfluidic device comprising, from top to bottom: (i) a bottomless multi-well plate comprising a plurality of bottomless wells, wherein four adjacent sequential wells comprise a culture chamber; (ii) a first micropatterned pressure-sensitive adhesive (PSA) layer attached to a bottom surface of the culture chamber; (iii) a polymer layer comprising four holes vertically aligned with the four adjacent sequential wells of the culture chamber, the polymer layer being attached to a bottom surface of the first micropatterned PSA layer; (iv) a second micropatterned PSA layer attached to a bottom surface of the polymer layer; (v) a third micropatterned PSA layer that connects the four adjacent sequential wells, wherein the third micropatterned PSA layer is attached to a bottom surface of the second micropatterned PSA layer; (vi) a transparent, optical grade glass layer attached to the bottom surface of the third micropatterned PSA layer that forms a bottom surface for the plurality of wells and that seals the multi-well plate-based pumpless perfusion culture device; (vii) a rocking platform for holding the multi-well plate, characterized by rocking speed and an adjustable rocking/tilt angle; wherein the four adjacent sequential wells that comprise the culture chamber comprise an inlet well, a cell seeding port well, a cell chamber well, and an outlet well; wherein the first micropatterned PSA layer is effective to maintain stable liquid droplets and to prevent medium evaporation by covering the inlet well, cell seeding port well, and outlet well of the first polymer layer; wherein the inlet and outlet wells are configured as reservoirs for culture medium and to generate hydrostatic pressure differential between the wells; wherein the cell seeding port well is adapted to receive a biological sample of cells; wherein a first polymer membrane between the second micropatterned PSA layer and third micropatterned PSA layer is effective to cover the inlet well and to control the flow rate of medium in the culture chamber; wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber; wherein the microfluidic device is effective to control flow of minute amounts of the liquids, nutrients and dissolved gas molecules in the MM cancer niche; wherein the ex vivo MM cancer niche is responsive to changing conditions of perfusion of the ex vivo MM cancer niche by the minute amounts of liquids, nutrients and dissolved gas molecules in the microfluidic device; and wherein formation of an ex vivo MM microenvironment in the microfluidic device is effective to recapitulate spatial and temporal characteristics of a multiple myeloma cancer niche in vivo and to maintain viability of the MM cells in the MM cancer niche in the microfluidic device ex vivo. According to one embodiment, the bio specimen comprising human myeloma cells further comprises human plasma autologous to the human myeloma cells. According to another embodiment, the microenvironment perfused by nutrients and dissolved gas molecules of the ex vivo bone marrow (BM) niche is effective for propagation of the human myeloma cells. According to another embodiment, the MM niche further comprises osteoblast-secreted and MM cell-secreted soluble cytokines and growth factors. According to another embodiment, the MM cells are adherent to osteoblasts of the BM niche. According to another embodiment, the MM cells adhere to the osteoblasts of the BM niche by cell-cell interaction. According to another embodiment, the human myeloma cells are cellular components of a bone marrow aspirate. According to another embodiment, the human myeloma cells are cellular components of peripheral blood. According to another embodiment, the human myeloma cells are cellular components of a core biopsy. According to another embodiment, the ex vivo multiple myeloma (MM) cancer niche is effective for propagation of the human myeloma cells for at least 4 days. According to another embodiment, the ex vivo multiple myeloma (MM) cancer niche is effective to maintain the viability and proliferative capacity of patient-derived MM cells for at least 3 weeks. According to another embodiment, the sample of human myeloma cells added to the BM niche constitutes $1\times10^4$ to $1\times10^5$ mononuclear cells. According to another embodiment, propagation of the MM cells is capable of producing deterioration of the 3D ossified tissue of the BM niche.

According to another aspect, the described invention provides a method for preparing an ex vivo multiple myeloma (MM) cancer niche contained in a device in which flow of minute amounts of liquids or dissolved gas molecules is controlled by microfluidics (microfluidic device), the microfluidic device comprising, from top to bottom: (i) a bottomless multi-well plate comprising a plurality of bottomless wells, wherein four adjacent sequential wells comprise a culture chamber; (ii) a first micropatterned pressure-sensitive adhesive (PSA) layer attached to a bottom surface of the culture chamber; (iii) a polymer layer comprising four holes vertically aligned with the four adjacent sequential wells of the culture chamber, the polymer layer being attached to a bottom surface of the first micropatterned PSA layer; (iv) a second micropatterned PSA layer attached to a bottom surface of the polymer layer; (v) a third micropatterned PSA layer that connects the four adjacent sequential wells, wherein the third micropatterned PSA layer is attached to a bottom surface of the second micropatterned PSA layer; (vi) a transparent, optical grade glass layer attached to the bottom surface of the third micropatterned PSA layer that forms a bottom surface for the plurality of wells and that seals the multi-well plate-based pumpless perfusion culture device; (vii) a rocking platform for holding the multi-well plate, characterized by rocking speed and an adjustable rocking/tilt angle; wherein the four adjacent sequential wells that comprise the culture chamber comprise an inlet well, a cell seeding port well, a cell chamber well, and an outlet well; wherein the first micropatterned PSA layer is effective to maintain stable liquid droplets and to prevent medium evaporation by covering the inlet well, cell seeding port well, and outlet well of the first polymer layer; wherein the inlet and outlet wells are configured as reservoirs for culture medium and to generate hydrostatic pressure differential between the wells; wherein the cell seeding port well is adapted to receive a biological sample of cells; wherein a first polymer membrane between the second micropatterned PSA layer and third micropatterned PSA layer is effective to cover the inlet well and to control the flow rate of medium in the culture chamber; wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber; the method comprising: (a) constructing an ex vivo bone marrow microenvironment perfused by nutrients and dissolved gas molecules (bone marrow niche) in the microfluidic device by: (i) seeding a surface of the microfluidic device with viable osteoblasts; and (ii) culturing the cells to form 3D nodular structures that comprise a 3D bone-like tissue; the 3D bone-like tissue being characterized by an extracellular matrix secreted by the viable adherent osteoblasts; (b) preparing a multiple myeloma tumor biospecimen composition comprising viable human multiple myeloma cells from a subject and plasma autologous to the subject; and (c) seeding the ex vivo bone marrow microenvironment perfused by nutrients and dissolved gas molecules with the MM tumor biospecimen, and forming an ex vivo microenvironment in the microfluidics device effective to recapitulate spatial and temporal characteristics of a multiple myeloma cancer niche in vivo and to maintain viability of the MM cells in the MM cancer niche in the microfluidics device ex vivo; wherein the microfluidic device is effective to control flow of minute amounts of the liquids, nutrients and dissolved gas molecules in the MM cancer niche; wherein the ex vivo MM cancer niche in the microfluidic device is responsive to changing conditions of perfusion of the ex vivo MM cancer niche by the minute amounts of liquids, nutrients and dissolved gas molecules in the microfluidics device. According to one embodiment, the MM niche further comprises osteoblast-secreted and MM cell-secreted soluble cytokines and growth factors. According to another embodiment, the MM cells are adherent to osteoblasts of the BM niche. According to another embodiment, the MM cells adhere to the osteoblasts of the BM niche by cell-cell interaction. According to another embodiment, the human myeloma cells are cellular components of a bone marrow aspirate. According to another embodiment, the human myeloma cells are cellular components of peripheral blood. According to another embodiment, the human myeloma cells are cellular components of a core biopsy. According to another embodiment, the ex vivo multiple myeloma (MM) cancer niche is suitable for propagation of the human myeloma cells for at least 4 days. According to another embodiment, the ex vivo multiple myeloma (MM) cancer niche is effective to maintain the viability and proliferative capacity of patient-derived MM cells for at least 3 weeks. According to another embodiment, the sample of human myeloma cells added to the BM niche constitutes $1\times10^4$ to $1\times10^5$ mononuclear cells. According to another embodiment, propagation of the MM cells is capable of producing deterioration of the 3D ossified tissue of the BM niche.

According to another aspect, the described invention provides a method for assessing chemotherapeutic efficacy of a test chemotherapeutic agent on viable human multiple myeloma cells seeded in an ex vivo microenvironment effective to recapitulate spatial and temporal characteristics of a multiple myeloma cancer niche and to maintain viability of the myeloma cells (MM cancer niche) obtained from a subject comprising: (a) preparing an in vitro microfluidic device comprising, from top to bottom: (i) a bottomless multi-well plate comprising a plurality of bottomless wells, wherein four adjacent sequential wells comprise a culture chamber; (ii) a first micropatterned pressure-sensitive adhesive (PSA) layer attached to a bottom surface of the culture chamber; (iii) a polymer layer comprising four holes vertically aligned with the four adjacent sequential wells of the culture chamber, the polymer layer being attached to a bottom surface of the first micropatterned PSA layer; (iv) a second micropatterned PSA layer attached to a bottom surface of the polymer layer; (v) a third micropatterned PSA layer that connects the four adjacent sequential wells, wherein the third micropatterned PSA layer is attached to a bottom surface of the second micropatterned PSA layer; (vi) a transparent, optical grade glass layer attached to the bottom surface of the third micropatterned PSA layer that forms a bottom surface for the plurality of wells and that seals the multi-well plate-based pumpless perfusion culture device; (vii) a rocking platform for holding the multi-well plate, characterized by a rocking speed and an adjustable rocking/tilt angle; wherein the four adjacent sequential wells that comprise the culture chamber comprise an inlet well, a cell seeding port well, a cell chamber well, and an outlet well; wherein the first micropatterned PSA layer is effective to maintain stable liquid droplets and to prevent medium evaporation by covering the inlet well, cell seeding port well, and outlet well of the first polymer layer; wherein the inlet and outlet wells are configured as reservoirs for culture medium and to generate hydrostatic pressure differential between the wells; wherein the cell seeding port well is adapted to receive a biological sample of cells; wherein a first polymer membrane between the second micropatterned PSA layer and third micropatterned PSA layer is effective to cover the inlet well and to control the flow rate of medium in the culture chamber; wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber; (b) constructing an ex vivo bone marrow microenvironment perfused by nutrients and dissolved gas molecules (bone marrow niche) by: (1) seeding a surface of the culture chamber of the in vitro microfluidic device of (a) with a population of cells comprising osteoblasts; (2) culturing the cells with a culture medium through the channel region for a time effective for the cells to form a confluent layer on the bottom surface of the channel, to then form multiple cell layers and to then form 3D nodular structures that comprise a 3D bone-like tissue; the 3D bone like tissue being characterized by a mineralized bone-like tissue comprising (a) viable osteoblasts self-organized into cohesive multiple cell layers and (b) an extracellular matrix secreted by the viable adherent osteoblasts; (c) preparing a multiple myeloma tumor biospecimen composition by: (1) acquiring a multiple myeloma tumor biospecimen from the subject, wherein the biospecimen comprises viable multiple myeloma cells; and (2) adding plasma autologous to the subject to the viable multiple myeloma cells; (3) bringing the biospecimen composition of (c)(2) comprising viable MM cells in contact with the osteoblasts of the ex vivo bone marrow microenvironment perfused by nutrients and dissolved gas molecules to seed the ex vivo bone marrow microenvironment with the viable MM cells, the ex vivo bone marrow microenvironment perfused by nutrients and dissolved gas molecules and the seeded MM cells in contact with the osteoblasts of the ex vivo bone marrow microenvironment forming an ex vivo microenvironment effective to recapitulate spatial and temporal characteristics of a multiple myeloma cancer niche and to maintain viability of the human MM cells (MM cancer niche); and (d) testing chemotherapeutic efficacy of a chemotherapeutic agent on the viable human MM cells maintained in the ex vivo MM cancer niche of (c)(3) in the test chamber of (a) by: (1) contacting the ex vivo MM cancer niche comprising viable human myeloma cells with a test chemotherapeutic agent; and (2) comparing at least one of viability and level of apoptosis of the MM cells in the MM cancer niche in the presence of the test chemotherapeutic agent to an untreated control; and (e) initiating therapy to treat the MM in the patient with the test chemotherapeutic agent if the test chemotherapeutic agent is effective to significantly ($P<0.05$) reduce viability of the MM cells or to increase apoptosis of the MM cells, compared to the untreated control. According to one embodiment, the chemotherapeutic agent is selected from the group consisting of an alkylating agent, an antimetabolite, a natural product, a hormone, a biologic, a kinase inhibitor, a platinum coordination complex, an EDTA derivative, a platelet-reducing agent, a retinoid and a histone deacetylase inhibitor. According to another embodiment, the chemotherapeutic agent is selected from the group consisting of an immunomodulatory drug, a proteasome inhibitor, a bisphosphonate, an immunomodulator or checkpoint inhibitor, a cancer vaccine, an adoptive cell therapy, an oncolytic virus therapy, and a targeted antibody. According to another embodiment, the immunomodulatory drug is Thalidomide, Lenalidomide, or Pomalidomide. According to another embodiment, the proteasome inhibitor is Bortezomib. According to another embodiment, the bisphosphonate is Pamidronate or zoledronic acid. According to another embodiment, the immunomodulator or checkpoint inhibitor is a CTLA-4 inhibitor, a IL-2/IL-2R activator, a PD-1/PD-L1 inhibitor, or a TLR activator. According to another embodiment, the cancer vaccine is effective to elicit an immune response to a target selected from a melanoma-associated antigen (MAGE), survivin, telomerase, a tumor-associated antigen (TAA), and WT1. According to another embodiment, the adoptive cell therapy is a CAR T cell therapy, a natural killer cell (NK) therapy, or a tumor infiltrating lymphocytes (TIL) therapy. According to another embodiment, the adoptive cell therapy is effective to target BCMA, CD19, CD20, NY-ESO-1, or WT1. According to another embodiment, the oncolytic virus therapy uses a measles virus, a reovirus, or a vesicular stomatitis virus. According to another embodiment, the targeted antibody is daratumumab or elotuzumab. According to another embodiment, the targeted antibody is an antibody to BCMA, CD19, CD20, CD38, CD52, EGFR, HER2, or SLAMF7. According to another embodiment, the MM niche further comprises osteoblast-secreted and MM cell-secreted soluble cytokines and growth factors. According to another embodiment, the MM cells are adherent to osteoblasts of the BM niche. According to another embodiment, the MM cells adhere to the osteoblasts of the BM niche by cell-cell interactions. According to another embodiment, the human myeloma cells are cellular components of a bone marrow aspirate. According to another embodiment, the human myeloma cells are cellular components of peripheral blood. According to another embodiment, the human myeloma cells are cellular components of a core biopsy. According to another embodiment, the period of time for dynamic propagation of the human myeloma cells in the ex vivo dynamic MM cancer niche is at least 4 days. According to another embodiment, the sample of human myeloma cells added to the BM niche constitutes $1 \times 10^4$ to $1 \times 10^5$ mononuclear cells. According to another embodiment, propagation of the MM cells in the ex vivo MM cancer niche under conditions that mimic interstitial flow; shear stresses exerted by the interstitial flow on the cells; increased blood flow associated with tumor cell expansion, or a combination thereof is effective to produce deterioration of the 3D ossified tissue of the BM niche. According to another embodiment, the method further comprises optionally cultivating the human myeloma cells in the MM cancer niche to propagate the MM cells for a period of time. According to another embodiment, the MM cancer niche is effective to maintain viability and proliferative capacity of the MM cells for at least 3 weeks. According to another embodiment, the method further comprises testing chemotherapeutic efficacy of a chemotherapeutic agent on the viable human MM cells maintained in the ex vivo MM cancer niche of (c)(3) in the test chamber of (a) by contacting the ex vivo MM cancer niche comprising viable human myeloma cells with a test chemotherapeutic agent under conditions that mimic interstitial flow; shear stresses exerted by the interstitial flow on the cells; increased blood flow associated with tumor cell expansion, or a combination thereof.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A is a picture of the 96-well plate-based microfluidic culture device, being rotated by a commercial rocking device, in a conventional incubator. FIG. 1B shows a schematic illustration of medium flow through the culture chamber induced by the hydrostatic pressure difference between the medium reservoirs. FIG. 1C shows a schematic view of the 4 wells used to support 1 culture chamber. FIG. 1D is a high content screening (HCS) image showing MM (black arrows) and OSB cells (white arrows).

FIG. 4A shows tilting angle changes and FIG. 4B shows the corresponding medium flow rate changes.

FIG. 5A-FIG. 5C show the device fabrication. FIG. 5A shows 4-well section illustrations of materials patterned and assembled to a bottomless 96-well based well plate. FIG. 5B shows pictures of digitally cut membranes assembled into the device. FIG. 5C shows the bottom of the fabricated device. The patterned PSA and PDMS layers were used to define microfluidic passages and imbed membranes between the bottomless 96-well plate and the glass plate.

FIG. 6A is an illustration of the experimental configuration. FIG. 6B is a picture of polystyrene microbeads floating on the medium surface captured by a microscope. FIG. 6C is a series of images showing the 20 µm accuracy of determining the vertical position of microbeads by microscopy as a means of measuring Δh. FIG. 6D shows a graph comparing experimentally measured and analytically calculated values of Δh. Error bars represent the standard deviation of the mean. Experiments were repeated three times.

FIG. 7A is fluorescence images of cells on day 4 in dynamic culture (left) and static culture (right). FIG. 7B is a graph showing cell viability after 4-day culture. FIG. 7C is a graph showing relative alkaline phosphatase (ALP) activity on day 4. Green=calcein AM (live cells), red=EthD-1 (dead cells), blue=nuclear stain (Hoechst 33324). Bars represent the mean and standard deviation of 4-5 separate wells. Statistical comparisons between perfusion and static cultures were performed using Student's t-test. *$P<0.05$, **$P<0.01$. Scale bar=100 µm.

FIG. 8A is a series of HCS images showing the response of MM.1S to bortezomib (therapeutic proteasome inhibitor marketed as Velcade® by Millennium Pharmaceuticals) when cultured alone (top) or in the presence of hFOB 1.19 cells (bottom). FIG. 8B is a graph showing the percentage of calcein AM$^+$ MM.1S (live MM.1S cells). FIG. 8C is a graph showing the percentage of EthD-1$^+$ MM.1S (dead MM.1S cells). Representative fields are shown. Data points represent the mean and standard deviation of 4-5 different wells. *$P<0.05$, $P<0.01$, *$P<0.001$ compared to MM.1S alone at the respective concentrations. Scale bar=100 µm.

DETAILED DESCRIPTION OF EMBODIMENTS

Definitions

Figures 1A, 1B:
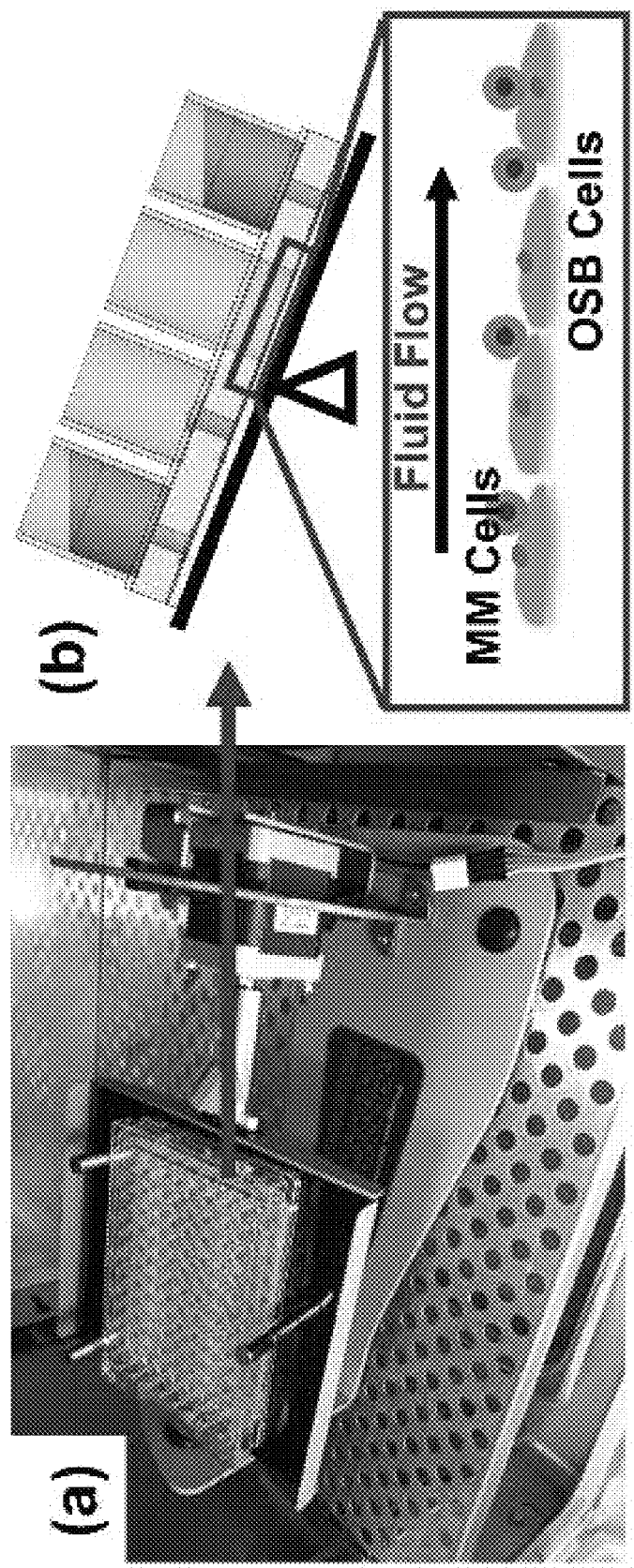
FIG. 1A-FIG. 1D show the design strategy for the pumpless culture platform.

Various terms used throughout this specification shall have the definitions set out herein.

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin (Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immmunoglobulins (antibodies). The soluble product of an activated T lymphocyte is lymphokines.

The term "administering" as used herein means to give or apply. It includes in vivo administration, as well as administration directly to tissue ex vivo. Generally, compositions can be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or can be locally administered by means such as, but not limited to, injection, implantation, grafting, or topical application.

The term "allogeneic" as used herein refers to being genetically different although belonging to or obtained from the same species.

The term "antigen" and its various grammatical forms refers to any substance that can stimulate the production of antibodies and can combine specifically with them. The term "antigenic determinant" or "epitope" as used herein refers to an antigenic site on a molecule.

An "antiserum" is the liquid phase of blood recovered after clotting has taken place obtained from an immunized mammal, including humans.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome c is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway (Loberg, R D, et al., J. Biol. Chem. 277 (44): 41667-673 (2002)). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

The term "arrange" as used herein refers to being disposed or placed in a particular kind of order.

The term "associate" and its various grammatical forms as used herein refers to joining, connecting, or combining to, either directly, indirectly, actively, inactively, inertly, non-inertly, completely or incompletely. The term "in association with" refers to a relationship between two substances that connects, joins or links one substance with another.

The term "autologous" as used herein means derived from the same organism.

The term "Bence Jones protein(s)" as used herein refers to Ig light chain of one type (either κ or λ) that appears in the urine of patients with multiple myeloma.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "bone" as used herein refers to a hard connective tissue consisting of cells embedded in a matrix of mineralized ground substance and collagen fibers. The fibers are impregnated with a form of calcium phosphate similar to hydroxyapatite as well as with substantial quantities of carbonate, citrate sodium and magnesium. Bone consists of a dense outer layer of compact substance or cortical substance covered by the periosteum and an inner loose, spongy substance; the central portion of a long bone is filled with marrow.

The term "bound" or any of its grammatical forms as used herein refers to the capacity to hold onto, attract, interact with or combine with. In the chemical arts, the term "binding" and its other grammatical forms means a lasting attraction between chemical substances.

The term "bone morphogenic protein (BMP)" as used herein refers to a group of cytokines that are part of the transforming growth factor-ß (TGF-ß) superfamily. BMP ligands bind to a complex of the BMP receptor type II and a BMP receptor type I (Ia or Ib). This leads to the phosphorylation of the type I receptor that subsequently phosphorylates the BMP-specific Smads (Smad1, Smad5, and Smad8), allowing these receptor-associated Smads to form a complex with Smad4 and move into the nucleus where the Smad complex binds a DNA binding protein and acts as a transcriptional enhancer. BMPs have a significant role in bone and cartilage formation in vivo. It has been reported that most BMPs are able to stimulate osteogenesis in mature osteoblasts, while BMP-2, 6, and 9 may play an important role in inducing osteoblast differentiation of mesenchymal stem cells (Cheng, H. et al., J. Bone & Joint Surgery 85: 1544-52 (2003)).

The term "buoyancy force" as used herein refers to the upward force exerted by any fluid upon a body placed in it. The symbol for the magnitude of buoyancy is B or $F_B$. Under Archimedes' principle, the magnitude of the buoyant force on an object is equal to the weight of the fluid it displaces, $B = \rho g V_{displaced}$, where $\rho$=density of the fluid; V=the volume of the fluid displaced; and g=the local acceleration due to gravity.

The term "capillary force" as used herein refers to the movement of liquid along the surface of a solid when adhesion to the walls of the surface is stronger than the cohesive forces between the liquid molecules.

The term "cell" is used herein to refer to the structural and functional unit of living organisms and is the smallest unit of an organism classified as living.

The term "cell adhesion" refers to adherence of cells to surfaces or other cells, or to the close adherence (bonding) to adjoining cell surfaces.

The term "cell adhesion molecule" refers to surface ligands, usually glycoproteins, that mediate cell-to-cell adhesion. Their functions include the assembly and interconnection of various vertebrate systems, as well as maintenance of tissue integration, wound healing, morphogenic movements, cellular migrations, and metastasis.

The term "cell-cell interaction" refers to the ways in which living cells communicate, whether by direct contact or by means of chemical signals.

The term "primary culture" as used herein refers to cells resulting from the seeding of dissociated tissues, e.g., patient-derived multiple myeloma cells (PMMC). Primary cultures often lose their phenotype and genotypes within several passages.

The term "cell line" as used herein refers to a permanently established cell culture developed from a single cell and therefore consisting of cells with a uniform genetic and functional makeup that will proliferate indefinitely in culture.

The term "cell strain" as used herein refers to cells which can be passed repeatedly but only for a limited number of passages.

The term "cell clones" as used herein refers to individual cells separated from the population and allowed to grow.

The term "cell passage" as used herein refers to the splitting (dilution) and subsequent redistribution of a monolayer or cell suspension into culture vessels containing fresh media.

The term "chemokine" as used herein refers to a class of chemotactic cytokines that signal leukocytes to move in a specific direction. The terms "chemotaxis" or "chemotactic" refer to the directed motion of a motile cell or part along a chemical concentration gradient towards environmental conditions it deems attractive and/or away from surroundings it finds repellent.

Cluster of Differentiation

The cluster of differentiation (CD) system is a protocol used for the identification of cell surface molecules present on white blood cells. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain immune functions. While using one CD molecule to define populations is uncommon, combining markers has allowed for cell types with very specific definitions within the immune system. There are more than 350 CD molecules identified for humans.

CD molecules are utilized in cell sorting using various methods, including flow cytometry. Cell populations usually are defined using a "+" or a "−" symbol to indicate whether a certain cell fraction expresses or lacks a CD molecule. For example, a "CD34+, CD31−" cell is one that expresses CD34, but not CD31. Table 2 shows commonly used markers employed by skilled artisans to identify and characterize differentiated white blood cell types.

TABLE 2

| Type of Cell | CD Markers |
| --- | --- |
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| Type of Cell | CD Markers |
| T helper cell | CD45+, CD3+, CD4+ |
| Cytotoxic T cell | CD45+, CD3+, CD8+ |
| B lymphocyte | CD45+, CD19+ or |
|  | CD45+, CD20+ |
| Thrombocyte | CD45+, CD61+ |
| Natural killer cell | CD16+, CD56+, CD3 |

CD molecules used in defining leukocytes are not exclusively markers on the cell surface. Most CD molecules have an important function, although only a small portion of known CD molecules have been characterized. For example, there are over 350 CDs for humans identified thus far.

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigen receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDA (glycosylphopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronection type III (FNIII) domains being involved in signaling leading to neurite outgrowth.

CD66b ((CGM1); CD67, CGM6, NCA-95) is a glycosylphosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

Human leukocyte antigen (HLA)-DR is a major histocompatibility complex (MHC) class II cell surface receptor. HLA-DR commonly is found on antigen-presenting cells such as macrophages, B-cells, and dendritic cells. This cell surface molecule is a αβ heterodimer with each subunit containing 2 extracellular domains: a membrane spanning domain and a cytoplasmic tail. Both the α and β chains are anchored in the membrane. The complex of HLA-DR and its ligand (a peptide of at least 9 amino acids) constitutes a ligand for the TCR.

Integrins are receptors that mediate attachment between a cell and the tissues surrounding it and are involved in cell-cell and cell-matrix interactions. In mammals, 18 α and 8 β subunits have been characterized. Both α and β subunits contain two separate tails, both of which penetrate the plasma membrane and possess small cytoplasmic domains.

Integrin αM (ITGAM; CD11b; macrophage-1 antigen (Mac-1); complement receptor 3 (CR3)) is a protein subunit of the heterodimeric integrin αMβ2 molecule. The second chain of αMβ2 is the common integrin β2 subunit (CD18). αMβ2 is expressed on the surface of many leukocytes including monocytes, granulocytes, macrophages and natural killer cells. It generally is believed that of αMβ2 mediates inflammation by regulating leukocyte adhesion and migration. Further, of αMβ2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin of αMβ2 is involved directly in causing the adhesion and spreading of cells, but cannot mediate cellular migration without the presence of the β2 (CD18) subunit.

CD61 (integrin β3; platelet glycoprotein IIIa; ITGB3) is a cell surface protein composed of an α-chain and a β-chain. A given chain may combine with multiple partners resulting in different integrins. CD61 is found along with the α IIb chain in platelets and is known to participate in cell adhesion and cell-surface mediated signaling.

CD63 (LAMP-3; ME491; MLA1; OMA81H) is a cell surface glycoprotein of the transmembrane 4 superfamily (tetraspanin family). Many of these cell surface receptors have four hydrophobic domains and mediate signal transduction events that play a role in the regulation of cell development, activation, growth and motility. CD63 forms complexes with integrins and may function as a blood platelet activation marker. It generally is believed that the sensitivity and specificity of measuring the upregulation of CD63 alone, or as part of a combination, is not specific enough to serve as a diagnostic marker for the diagnosis of IgE mediated allergy.

CD123 is the 70 kD transmembrane a chain of the cytokine interleukin-3 (IL-3) receptor. Alone, CD123 binds IL-3 with low affinity; when CD123 associates with CDw131 (common β chain), it binds IL-3 with high affinity. CD123 does not transduce intracellular signals upon binding IL-3 and requires the β chain for this function. CD123 is expressed by myeloid precursors, macrophages, dendritic cells, mast cells, basophils, megakaryocytes, and some B cells. CD123 induces tyrosine phosphorylation within the cell and promotes proliferation and differentiation within the hematopoietic cell lines.

CD203c (ectonucleotide pyrophosphatase/phosphodiesterase 3; ENPP3) is an ectoenzyme constitutively and specifically expressed on the cell surface and within intracellular compartments of basophils, mast cells, and precursors of these cells. CD203c detection by flow cytometry has been used to specifically identify basophils within a mixed leukocyte suspension, since its expression is unique to basophils among the cells circulating in blood. The expression of CD203c is both rapidly and markedly upregulated following IgE-dependent activation. However, as with CD63, it is generally believed that the sensitivity and specificity of measuring the upregulation of CD203c alone, or as part of a combination, is not specific enough to serve as a diagnostic marker for the diagnosis of IgE mediated allergy. Further, the exact role of CD203c in basophil biology is unknown.

CD294 (G protein-coupled receptor 44; GPR44; CRTh2; DP2) is an integral membrane protein. This chemoattractant receptor homologous molecule is expressed on T helper type-2 cells. The transmembrane domains of these proteins mediate signals to the interior of the cell by activation of heterotrimeric G proteins that in turn activate various effector proteins that ultimately result a physiologic response.

The term "clone" as used herein refers to a population of cells formed by repeated division from a common cell.

The term "compatible" as used herein means that the components of a composition are capable of being combined with each other in a manner such that there is no interaction that would substantially reduce the efficacy of the composition under ordinary use conditions.

The term "complement" as used herein refers to a system of plasma proteins that interact with pathogens to mark them for destruction by phagocytes. Complement proteins can be activated directly by pathogens or indirectly by pathogen-bound antibody, leading to a cascade of reactions that occurs on the surface of pathogens and generates active components with various effector functions.

The term "component" as used herein refers to a constituent part, element or ingredient.

The term "composition" as used herein refers to an aggregate material formed of two or more substances.

The transitional term "comprising", which is synonymous with "including," "containing," or "characterized by," is inclusive or open-ended and does not exclude additional, unrecited elements or method steps.

The term "concentration" as used herein refers to the amount of a substance in a given volume.

The term "concurrent" as used herein refers to occurring, or to operating, before, during or after an event, episode or time period.

The term "condition", as used herein, refers to a variety of health states and is meant to include disorders or diseases caused by any underlying mechanism or injury.

The term "connected" as used herein refers to being joined, linked, or fastened together in close association.

The term "contact" as used herein refers to the state or condition of touching or being in immediate proximity.

The terms "culture" and "cell culture" as used herein refers to the cultivation of cells in or on a controlled or defined medium. The terms "culture-expanded" or "expanded" are used interchangeably to refer to an increase in the number or amount of viable cells by cultivation of the cells in or on a controlled or defined medium. The term "culture medium" (or plural, media), as used herein refers to a substance containing nutrients in which cells or tissues are cultivated for controlled growth.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins including interleukin 2 (IL-2), as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "cytometry" as used herein, refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and to collect cells.

The term "dendritic cells" (DCs) as used herein, refers to professional antigen presenting cells (APCs) capable of presenting both MHC-I and MHC-II antigens.

The phrase "density-dependent inhibition of growth" as used herein refers to reduced response of cells upon reaching a threshold density. These cells recognize the boundaries of neighbor cells upon confluence and respond, depending on growth patterns, by forming a monolayer. Usually these cells transit through the cell cycle at reduce rate (grow slower).

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative."

The term "derived from" as used herein is used to refer to originating, sourced, or coming from.

The term "differential label" as used herein, generally refers to a stain, dye, marker, antibody or antibody-dye combination, or intrinsically fluorescent cell-associated molecule, used to characterize or contrast components, small molecules, macromolecules, e.g., proteins, and other structures of a single cell or organism. The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-whodamine, Lissamine Rhodamine B, Texas Red, TruRed, and derivatives thereof.

The term "differentiation" as used herein refers to a property of cells to exhibit tissue-specific differentiated properties in culture.

The term "dissolved gas molecules" as used herein refers to molecules (e.g., $O_2$, $CO_2$, etc.) dissolved in cell culture medium.

The term "disease" or "disorder," as used herein, refers to an impairment of health or a condition of abnormal functioning.

The term "drug" as used herein refers to a therapeutic agent or any substance used in the prevention, diagnosis, alleviation, treatment, or cure of disease.

The term "dynamic" as used herein refers to changing conditions to which an agent must adapt.

The terms "dynamic viscosity" or "absolute viscosity" as used herein refers to the internal resistance to movement of one layer of a fluid over another. Dynamic viscosity ($\mu$) is measured in Pascal-second units (Pa·s).

The term "endosteal" as used herein refers to a connective tissue that lines the surface of bony tissue that forms the medullary cavity of long bones.

The term "extracellular matrix" as used herein refers to a construct in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fibronectin, and laminin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans.

Flow Cytometry

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

FACS

The term "fluorescence-activated cell sorting" (also referred to as "FACS"), as used herein, refers to a method for sorting a heterogeneous mixture of biological cells into one or more containers, one cell at a time, based upon the specific light scattering and fluorescent characteristics of each cell.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then returned to neutral after the droplet breaks off.

The term "growth" as used herein refers to a process of becoming larger, longer or more numerous, or an increase in size, number, or volume.

The term "growth factor" as used herein refers to signal molecules involved in the control of cell growth and differentiation and cell survival.

The terms "high-content screening (HCS)" or "high-content analysis" as used herein refers to a set of analytical methods using automated microscopy, multi-parameter image processing, and visualization tools to extract quantitative data from cell populations. HCS typically employs fluorescence imaging of samples in a high-throughput format and reports quantitatively on parameters such as spatial distribution of targets and individual cell and organelle morphology.

The term "hybridoma cell" as used herein refers to an immortalized hybrid cell resulting from the in vitro fusion of an antibody-secreting B cell with a myeloma cell. For example, monoclonal antibodies (mAbs) can be generated by fusing mouse spleen cells from an immunized donor with a mouse myeloma cell line to yield established mouse hybridoma clones that grow in selective media.

The term "hydrostatic pressure" as used herein refers to the pressure exerted by a fluid at equilibrium at a given point within the fluid, due to the force of gravity. Hydrostatic pressure increases in proportion to depth measured from the surface because of the increasing weight of fluid exerting downward force from above.

The term "immunoglobulin (Ig)" as used herein refers to one of a class of structurally related proteins, each consisting of two pairs of polypeptide chains, one pair of identical light (L) (low molecular weight) chains ($\kappa$ or $\lambda$), and one pair of identical heavy (H) chains ($\gamma$, $\alpha$, $\mu$, $\delta$ and $\varepsilon$), usually all four linked together by disulfide bonds. On the basis of the structural and antigenic properties of the H chains, Igs are classified (in order of relative amounts present in normal human serum) as IgG, IgA, IgM, IgD, and IgE. Each class of H chain can associate with either $\kappa$ or $\lambda$ L chains. There are four subclasses of IgG immunoglobulins (IgG1, IgG2, IgG3, IgG4) having $\gamma 1$, $\gamma 2$, $\gamma 3$, and $\gamma 4$ heavy chains respectively. In its secreted form, IgM is a pentamer composed of five four-chain units, giving it a total of 10 antigen binding sites. Each pentamer contains one copy of a J chain, which is covalently inserted between two adjacent tail regions.

The term Ig refers not only to antibodies, but also to pathological proteins classified as myeloma proteins, which appear in multiple myeloma along with Bence Jones proteins, myeloma globulins, and Ig fragments.

Antibodies are serum proteins, the molecules of which possess small areas of their surface that are complementary to small chemical groupings on their targets. Both light and heavy chains usually cooperate to form the antigen binding surface. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions.

All five immunoglobulin classes differ from other serum proteins in that they normally show a broad range of electrophoretic mobility and are not homogeneous. This heterogeneity—that individual IgG molecules, for example, differ from one another in net charge—is an intrinsic property of the immunoglobulins, and accounts for the libraries of antibodies each individual possesses.

The term "immunoglobulin fragment" ("Ig fragment") refers to a partial immunoglobulin molecule.

The term "in vitro immunization" is used herein to refer to primary activation of antigen-specific B cells in culture.

The term "inhibit" and its various grammatical forms, including, but not limited to, "inhibiting" or "inhibition", are used herein to refer to reducing the amount or rate of a process, to stopping the process entirely, or to decreasing, limiting, or blocking the action or function thereof. Inhibition can include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor can stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury," as used herein, refers to damage or harm to a structure or function of the body caused by an outside agent or force, which can be physical or chemical.

The term "immunomodulatory cell(s)" as used herein refer(s) to cell(s) that are capable of augmenting or diminishing immune responses by expressing chemokines, cytokines and other mediators of immune responses.

The term "inflammatory cytokines" or "inflammatory mediators" as used herein refers to the molecular mediators of the inflammatory process, which may modulate being either pro- or anti-inflammatory in their effect. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, pro-inflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), and interleukin-12 (IL-12).

The term "interacted with" as used herein refers to a kind of action that occurs as two or more objects have an effect upon one another.

The term "interleukin (IL)" as used herein refers to a cytokine secreted by, and acting on, leukocytes. Interleukins regulate cell growth, differentiation, and motility, and stimulates immune responses, such as inflammation. Examples of interleukins include interleukin-1 (IL-1), interleukin 2 (IL-2), interleukin-1β (IL-1β), interleukin-6 (IL-6), interleukin-8 (IL-8), and interleukin-12 (IL-12).

The term "isolated" is used herein to refer to material, such as, but not limited to, a cell, nucleic acid, peptide, polypeptide, or protein, which is substantially or essentially free from components that normally accompany or interact with it as found in its naturally occurring environment.

The term "Kaplan Meier plot" or "Kaplan Meier survival curve" as used herein refers to a plot of probability of clinical study patients surviving in a given length of time while considering time in many small intervals. The Kaplan Meier plot assumes that: (i) at any time patients who are censored (i.e., lost) have the same survival prospects as patients who continue to be followed; (ii) the survival probabilities are the same for patients recruited early and late in the study; and (iii) the event (e.g., death) happens at the time specified. Probabilities of occurrence of event are computed at a certain point of time with successive probabilities multiplied by any earlier computed probabilities to get a final estimate. The survival probability at any particular time is calculated as the number of patients surviving divided by the number of patients at risk. Patients who have died, dropped out, or have been censored from the study are not counted as at risk.

The terms "label" or "labeled" as used herein refers to incorporation of a detectable marker or molecule.

The term "major histocompatibility complex (MHC)" as used herein refers to a cluster of genes that encodes a set of membrane glycoproteins (the MHC molecules). The major Mhc-Ii genes of humans are the HLA-DRA and HLA-DRB that encode the chains that form the HLA-DR molecule, a major antigen presentation element. The binding of peptides by an MHC-I or MHC-II molecule is the initial selective event that permits the cell expressing the MHC molecule (the APC, or when this cell is to be the recipient of a cytolytic signal, the target cell) to sample fragments derived either from its own proteins (for MHC-I-restricted antigen presentation) or from those proteins ingested from the immediate extracellular environment (in the case of MHC- II). The biochemical steps involved in the production of antigen fragments from large molecules are collectively known as "antigen processing"; those that concern the binding of antigen fragments by MHC molecules and their display at the cell surface are known as "antigen presentation".

The term "marker" as used herein refers to a receptor, or a combination of receptors, found on the surface of a cell. These markers allow a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body.

The term "matrix" as used herein refers to a three dimensional network of fibers that contains voids (or "pores") where the woven fibers intersect. The structural parameters of the pores, including the pore size, porosity, pore interconnectivity/tortuosity and surface area, affect how fluid, solutes and cells move in and out of the matrix.

The term "microfluidics" refers to a set of technologies that control the flow of minute amounts of liquids or dissolved gas molecules, typically measured in nano- and pico-liters in a miniaturized system. The microchips require only a small amount of sample and reagent for each process, and microscale reactions occur much faster because of the physics of small fluid volumes.

The term "(culture) medium flow rate" or "flow rate" as used herein refers to the volume of culture fluid which passes per unit time, for example, expressed in μL/min, and is represented herein by the symbol (Q).

The term "modulate" as used herein means to regulate, alter, adapt, or adjust to a certain measure or proportion.

The term "monoclonal" as used herein refers to resulting from the proliferation of a single clone.

The term "monoclonal Ig" as used herein refers to a homogeneous immunoglobulin resulting from the proliferation of a single clone of plasma cells and which, during electrophoresis of serum, appears as a narrow band or "spike". It is characterized by H chains of a single class and subclass, and light chains of a single type.

The term "monolayer" as used herein refers to a layer of cells one cell thick, grown in a culture.

As used herein, the terms "osteoprogenitor cells," "mesenchymal cells," "mesenchymal stem cells (MSC)," or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals. The collagen strands to form osteoids: spiral fibers of bone matrix. Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) Colony-forming unit-fibroblast (CFU-F); (ii) mesenchymal stem cell/marrow stromal cell (MSC); (3) osteoblast; (4) osteocyte.

The term "osteogenesis" refers to the formation of new bone from bone forming or osteocompetent cells.

The term "osteocalcin" as used herein refers to a protein constituent of bone; circulating levels are used as a marker of increased bone turnover.

The term "osteoclast" as used herein refers to the large multinucleate cells associated with areas of bone resorption bone resorption (breakdown).

The term "osteogenic factors" refers to the plethora of mediators associated with bone development and repair, including, but not limited to bone morphogenic proteins (BMPs), vascular endothelial growth factor (VEGF), basic fibroblast growth factor (bFGF), transforming growth factor beta (TGFβ), and platelet-derived growth factor (PDGF).

The term "overall survival" (OS) as used herein refers to the length of time from either the date of diagnosis or the start of treatment for a disease that subjects diagnosed with the disease are still alive.

The term "perfusion" as used herein refers to the process of nutritive delivery of arterial blood to a capillary bed in biological tissue. Perfusion ("F") can be calculated with the formula $F=((PA-Pv)/R)$ wherein PA is mean arterial pressure, Pv is mean venous pressure, and R is vascular resistance. Tissue perfusion can be measured in vivo, by, for example, but not limited to, magnetic resonance imaging (MRI) techniques. Such techniques include using an injected contrast agent and arterial spin labeling (ASL) (wherein arterial blood is magnetically tagged before it enters into the tissue of interest and the amount of labeling is measured and compared to a control recording). Tissue perfusion can be measured in vitro, by, for example, but not limited to, tissue oxygen saturation ($StO_2$) using techniques including, but not limited to, hyperspectral imaging (HSI).

The term "polymer" as used herein refers to a macromolecule formed by the chemical union of five or more identical combining units (monomers). Exemplary polymers by type include, without limitation, inorganic polymers (e.g., siloxane, sulfur chains, black phosphorus, boron-nitrogen, alumino silicate, boro silicate, or boro-alumino silicate, glass ceramics, ceramics, and semiconductor or crystalline materials (e.g. silicones); Organic polymers, including natural organic polymers e.g., polysaccharides, such as starch, cellulose, pectin, seaweed gums (agar, etc), vegetable gums (Arabic, etc.); polypeptides (e.g., albumin, globulin); and hydrocarbons, e.g., polyisoprene; synthetic polymers, including thermoplastic polymers, such as polyvinyl chloride, polyethylene (linear), polystyrene, polypropylene, fluorocarbon resins, polyurethane, and acrylate resins, and thermosetting synthetic polymers, such as elastomers, polyethylene (cross-linked), phenolics, and polyesters; and semi-synthetic organic polymers, such as cellulosics (e.g., methylcellulose, cellulose acetate) and modified starches. Further examples of polymers include, without limitation, hydrophilic polyethylene, polystyrenes, polypropylenes, acrylates, methacrylates, polycarbonates, polysulfones, polyesterketones, poly- or cyclic olefins, polychlorotrifluoroethylene, and polyethylene therephthalate.

The term "pore" as used herein refers to a void or minute opening. The term "pore size" as used herein refers to the diameter of the individual pores in a material, typically specified in micrometers (μm). Most membranes and filter media contain a distribution of pore sizes, meaning that pores larger and smaller may be present.

The term "porosity" as used herein refers to the percent of the total surface area or total volume of a material occupied by pores, and symbolized by ($\varepsilon$).

The term "pressure differential" as used herein refers to the difference in pressure between two points in a system.

The term "progression free survival" or "PFS" as used herein refers to length of time during and after the treatment of a disease, such as cancer, that a patient lives with the disease but it does not get worse. In a clinical trial, measuring the progression free survival is one way to determine how well a new treatment works.

The terms "proliferation" and "propagation" are used interchangeably herein to refer to expansion of a population of cells by the continuous division of single cells into identical daughter cells.

The term "reduce" or "reducing" as used herein refers to the limiting of an occurrence of a disease, disorder or condition in individuals at risk of developing the disorder.

The term "relapse" as used herein refers to the return of a disease or the signs and symptoms of a disease after a period of improvement.

The term "relapse-free survival (RFS)" as used herein refers to the length of time after primary treatment for a cancer during which the patient survives without any signs or symptoms of that cancer. Also called disease-free survival (DFS).

The term "shear stress" as used herein refers to the frictional force tending to cause deformation of a material by slippage along a plane or planes parallel to the imposed stress. Shear stress is measured in pascals (Pa) and is denoted by ($\tau$). The term "shear stress" in context of a fluid means a force per unit area, acting parallel to an infinitesimal surface element. Shear stress is primarily caused by friction between fluid particles, due to fluid viscosity.

The term "stimulate" in any of its grammatical forms as used herein refers to inducing activation or increasing activity.

As used herein, the terms "subject" or "individual" or "patient" are used interchangeably to refer to a member of an animal species of mammalian origin, including humans. The term "a subject in need thereof" is used to refer to a subject who presents with presents with diagnostic markers and symptoms associated with multiple myeloma and either (i) will be in need of treatment, (ii) is receiving treatment; or (iii) has received treatment, unless the context and usage of the phrase indicates otherwise.

The term "surface tension" as used herein refers to the property of the surface of a liquid that allows it to resist an external force, due to the cohesive nature of its molecules. For a molecule on the surface of the liquid, there will be a net inward force since there will be no attractive force acting from above. This inward net force causes the molecules on the surface to contract and to resist being stretched or broken. Due to the surface tension, small objects will "float" on the surface of a fluid, as long as the object cannot break through and separate the top layer of water molecules. When an object is on the surface of the fluid, the surface under tension will behave like an elastic membrane.

The term "suspension culture" as used herein refers to cells which do not require attachment to a substratum to grow, i.e. they are anchorage independent. Cell cultures derived from blood are typically grown in suspension, where the cells can grow as single cells or clumps. To subculture the cultures which grow as single cells they can be diluted. However, the cultures containing clumps need to have the clumps disassociated prior to subculturing of the culture.

The term "symptom" as used herein refers to a phenomenon that arises from and accompanies a particular disease or disorder and serves as an indication of it.

The term "syndrome" as used herein refers to a pattern of symptoms indicative of some disease or condition.

The term "target" as used herein refers to a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The terms "therapeutic amount", "therapeutically effective amount", an "amount effective", or "pharmaceutically effective amount" of an active agent is used interchangeably to refer to an amount that is sufficient to provide the intended benefit of treatment.

The term "therapeutic effect" as used herein refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

The term "two-dimensional tissue construct" as used herein refers to a collection of cells and the intercellular substances surrounding them in a geometric configuration having length and width.

The term "three-dimensional tissue construct" as used herein refers to a tissue like collection of cells and the intercellular substances surrounding them in a geometric configuration having length, width, and depth.

The term "transplantation" as used herein, refers to removal and transfer of cells, a tissue or an organ from one part or individual to another.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "tumor necrosis factor" (TNF) as used herein refers to a cytokine made by white blood cells in response to an antigen or infection, which induce necrosis (death) of tumor cells and possesses a wide range of pro-inflammatory actions. Tumor necrosis factor also is a multifunctional cytokine with effects on lipid metabolism, coagulation, insulin resistance, and the function of endothelial cells lining blood vessels.

The terms "VEGF-1" or "vascular endothelial growth factor-1" are used interchangeably herein to refer to a cytokine that mediates numerous functions of endothelial cells including proliferation, migration, invasion, survival, and permeability. VEGF is critical for angiogenesis.

I. An In Vitro Multiwell Plate-Based Pumpless Perfusion Culture Device

According to some embodiments, the described invention provides an in vitro multiwell plate-based pumpless perfusion culture device. According to some embodiments, the device comprises, from top to bottom:

(i) a bottomless multi-well plate comprising a plurality of bottomless wells, wherein four adjacent sequential wells comprise a culture chamber;

(ii) a first micropatterned pressure-sensitive adhesive (PSA) layer attached to a bottom surface of the culture chamber;

(iii) a polymer layer comprising four holes vertically aligned with the four adjacent sequential wells of the culture chamber, the polymer layer being attached to a bottom surface of the first micropatterned PSA layer;

(iv) a second micropatterned PSA layer attached to a bottom surface of the polymer layer;

(v) a third micropatterned PSA layer that connects the four adjacent sequential wells, wherein the third micropatterned PSA layer is attached to a bottom surface of the second micropatterned PSA layer;

(vi) a transparent, optical grade glass layer attached to the bottom surface of the third micropatterned PSA layer that forms a bottom surface for the plurality of wells and that seals the multi-well plate-based pumpless perfusion culture device; and (vii) a rocking platform for holding the multi-well plate, characterized by a rocking speed and an adjustable rocking/ tilt angle;

wherein the four adjacent sequential wells that comprise the culture chamber comprise an inlet well, a cell seeding port well, a cell chamber well, and an outlet well;

wherein the first micropatterned PSA layer is effective to maintain stable liquid droplets and to prevent medium evaporation by covering the inlet well, cell seeding port well, and outlet well of the first polymer layer;

wherein the inlet and outlet wells are configured as reservoirs for culture medium and to generate a hydrostatic pressure differential between the wells;

wherein the cell seeding port well is adapted to receive a biological sample of cells;

wherein a first polymer membrane between the second micropatterned PSA layer and third micropatterned PSA layer is effective to cover the inlet well and to control the flow rate of medium in the culture chamber;

wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber.

According to some embodiments, the device comprises a plurality of layers. The term "bottomless multi-well plate" as used herein refers to a multi-well plate without a bottom surface; and the term "bottomless wells" as used herein refers to wells of the multi-well plate without a bottom surface. According to some embodiments, the multi-well plate comprises at least 6, at least 12, at least 24, at least 48, at least 96, at least 384 or at least 1536 wells. According to some embodiments, the multi-well plate comprises 96 wells. According to some embodiments, the wells may have dimensions substantially same as the dimensions of the wells in plates currently commercially available for commercially available readers and dispensers. According to some embodiments, the multi-well plate has a substantially rectangular shape appropriate for commercially available readers and dispensers. According to some embodiments, the multi-well plate can have a shape different from rectangular.

According to some embodiments, the multi-well plate may be constructed of polymeric materials. Exemplary polymers include, without limitation, hydrophilic polyethylenes, polystyrenes, polypropylenes, acrylates, methacrylates, polycarbonates, polysulfones, polyesterketones, poly- or cyclic olefins, polychlorotrifluoroethylene, and polyethylene therephthalate. According to some embodiments, the multi-well plate may be constructed of polystyrene. According to some embodiments, the multi-well plate may be constructed of inorganic polymer materials.

According to some embodiments, four adjacent sequential wells of the multi-well plate comprise a culture chamber. According to some embodiments, the microfluidic device comprises 20 culture chambers with each culture chamber occupying four wells. According to some embodiments, a culture chamber comprises four adjacent sequential wells comprising, in sequential order, an inlet well, a cell seeding port well, a cell chamber well, and an outlet well. According to some embodiments, the inlet and outlet wells function as reservoirs for culture medium and to generate a hydrostatic pressure differential between the wells (ΔP). According to some embodiments, cells are plated through the cell seeding port well. According to some embodiments, the cell seeding port directs cell placement into the culture chamber.

According to some embodiments, the device comprises one or more layers of pressure-sensitive adhesive (PSA), including one layer, two layers, three layers, four layers, or more of PSA. According to some embodiments, the device comprises three layers of PSA. According to some embodiments, the PSA is an acrylic hybrid PSA. According to some embodiments, the PSA is a clear polyester double-sided adhesive tape. According to some embodiments, the PSA is a 1 mm thick clear polyester film coated on both sides with an MA-69 acrylic hybrid medical grade adhesive. According to some embodiments, the PSA is about 5.6 mm thick. According to some embodiments, the PSA is from about 1 to about 10 mm thick, for example, about 1 mm thick, about 1.5 mm thick, about 2 mm thick, about 2.5 mm thick, about 3 mm thick, about 3.5 mm thick, about 4 mm thick, about 4.5 mm thick, about 5 mm thick, about 5.5 mm thick, about 6 mm thick, about 6.5 mm thick, about 7 mm thick, about 7.5 mm thick, about 8 mm thick, about 8.5 mm thick, about 9 mm thick, about 9.5 mm thick, or about 10 mm thick. According to some embodiments, the PSA is ARcare® 90106 (Adhesives Research, Inc., Glen Rock, Pa.). According to some embodiments, the PSA is micropatterned with a plurality of holes therethrough. The term "micropatterning" refers to a method of modifying the properties of cell culture substrates at sub-cellular scales, which can be used to restrict the location and shape of the substrate regions in which cells can attach ("micropatterns"). Engineered micropatterns can provide a micrometer-scale, soft, 3-dimensional, complex and dynamic microenvironment for individual cells or for multi-cellular arrangements. See Thery, M, J. Cell Sci. (2010) 123 (24): 4201-13).

According to some embodiments, a first PSA layer is attached to the bottom surface of the multi-well plate. According to some embodiments, the first PSA layer is micropatterned to pattern the surface of the inlet and outlet wells and the cell seeding port well. According to some embodiments, the first PSA layer is patterned with a ring structure exhibited on each surface of the inlet, outlet, and cell seeding port wells. According to some embodiments, the first PSA layer maintains stable liquid droplets and prevents medium evaporation. According to some embodiments, the first PSA layer (1) holds the medium in the cell seeding port by surface tension during dynamic culture, and (2) prevents evaporation of liquid in the medium reservoir ports during device pre-treatment and static culture. According to some embodiments, the first PSA layer has a hole that is vertically aligned with the cell chamber well of the culture chamber.

According to some embodiments, a polymer layer is attached to the bottom surface of the first PSA layer. According to some embodiments, the polymer layer comprises a polymer, for example, polydimethylsiloxane (PDMS), polystyrene, or the like. According to some embodiments, the polymer layer comprises a plurality of holes that are vertically aligned with the four adjacent sequential wells of the culture chamber. According to some embodiments, the holes aligned with the inlet, outlet, and cell seeding port well are each about 6 mm diameter. According to some embodiments, the hole aligned with to the cell chamber well is about 1.5 mm diameter. According to some embodiments, the polymer layer is plasma treated before adhesion to the adjacent layers of the device.

According to some embodiments, a second PSA layer is attached to the bottom surface of the polymer layer. According to some embodiments, the second PSA layer comprises a plurality of holes that are vertically aligned with the four adjacent sequential wells of the culture chamber. According to some embodiments, the plurality of holes correspond in vertical placement and size with the holes in the polymer layer. According to some embodiments, the second PSA layer adheres and seals the polymer membranes below.

According to some embodiments, the device comprises one or more polymer membranes. According to some embodiments, the device comprises two polymer membranes. According to some embodiments, the polymer membranes are embedded between two layers of PSA. According to some embodiments, the polymer membranes are embedded between the second and third layers of PSA. According to some embodiments, the first polymer membrane is vertically aligned with the inlet well of the culture chamber (See membrane circled in blue, FIG. 2). According to some embodiments, the first polymer membrane comprises polycarbonate (PCTE). According to some embodiments, the first polymer membrane is a thin, translucent microporous hydrophilic PCTE film. According to some embodiments, the first polymer membrane is characterized by a pore size of about 0.4 µm, a porosity of about 10%, and a thickness of about 10 µm. According to some embodiments, the first polymer membrane is Sterlitech™ PCT0447100 (Sterlitech, Kent, Wash.). According to some embodiments, the first polymer membrane controls the medium flow rate (Q). According to some embodiments, the second polymer membrane is vertically aligned with the cell chamber well of the culture chamber (See membrane circled in red, FIG. 2). According to some embodiments, the second polymer membrane comprises polyester (PETE). According to some embodiments, the second polymer membrane is a solvent-resistant, hydrophilic, thin, translucent, microporous, PETE film. According to some embodiments, the second polymer membrane is characterized by a pore size of about 0.4 µm and a thickness of about 12 µm. According to some embodiments, the second polymer membrane is Sterlitech™ 1300017 (Sterlitech, Kent, Wash.). According to some embodiments, the second polymer membrane holds the medium within the cell chamber during cell seeding and culture.

According to some embodiments, a third PSA layer adheres to the bottom surface of the second PSA layer and the bottom surfaces of the polymer membranes. According to some embodiments, the third PSA layer adheres to the top surface of the glass plate. According to some embodiments, the third PSA layer contains a microchannel which connects the four adjacent sequential wells of the culture chamber. According to some embodiments, the third PSA layer comprises a hole vertically aligned with the cell chamber well that define the shape and dimensions of the bottom of the well. According to some embodiments, the hole in the third PSA layer is hexagonal in shape with a lateral surface area of 38.3 mm$^2$, which is comparable to that of a typical 96 well plate (38.5 mm$^2$). According to some embodiments, the thickness of the third PSA layer is 0.137 mm.

According to some embodiments, the cell chamber well is connected to the cell seeding port well by a microchannel. According to some embodiments, the dimensions of the microchannel are about 0.5 mm in width and about 0.137 mm in depth.

According to some embodiments, the glass plate provides optical access through the bottom of the culture chamber for cell characterization with plate readers. According to some embodiments, the glass plate is attached to a bottom of the third PSA layer to seal the multi-well plate culture device thereby forming a bottom surface thereof for the plurality of wells. According to some embodiments, the glass plate is about 1.2 mm-thick.

According to some embodiments, the rocking platform maintains a medium flow rate in the culture chamber of about 0.46 µL/min to about 0.5 µL/min. According to some embodiments, during culture, the tilt or angle of the rocking platform (meaning the amount that the rocker platform tilts back and forth) is used to control medium flow. According to some embodiments, during culture, the tilt or angle of the rocking platform is used to control medium flow within about 10% (±10%).

According to some embodiments, the device is configured to maintain a flow-induced shear stress of about 0.4 mPa. According to some embodiments, the device is configured to maintain a hydrostatic pressure differential between wells of about 67 Pa.

II. An Ex Vivo Multiple Myeloma (MM) Cancer Niche Contained in a Device

According to one aspect, the described invention provides an ex vivo multiple myeloma (MM) cancer niche contained in a device in which flow of minute amounts of liquids or dissolved gas molecules is controlled by microfluidics (a microfluidic device) comprising:

(a) an ex vivo bone marrow microenvironment perfused by nutrients and dissolved gas molecules (bone marrow niche) comprising viable osteoblasts seeded on a surface of the microfluidic device and cultured to form 3D nodular structures that comprise a 3D bone-like tissue, the 3D bone-like tissue being characterized by an extracellular matrix secreted by the viable osteoblasts; and (b) a multiple myeloma tumor biospecimen comprising viable human multiple myeloma cells; the microfluidic device comprising, from top to bottom:

(i) a bottomless multi-well plate comprising a plurality of bottomless wells, wherein four adjacent sequential wells comprise a culture chamber;

(ii) a first micropatterned pressure-sensitive adhesive (PSA) layer attached to a bottom surface of the culture chamber;

(iii) a polymer layer comprising four holes vertically aligned with the four adjacent sequential wells of the culture chamber, the polymer layer being attached to a bottom surface of the first micropatterned PSA layer;

(iv) a second micropatterned PSA layer attached to a bottom surface of the polymer layer;

(v) a third micropatterned PSA layer that connects the four adjacent sequential wells, wherein the third micropatterned PSA layer is attached to a bottom surface of the second micropatterned PSA layer;

(vi) a transparent, optical grade glass layer attached to the bottom surface of the third micropatterned PSA layer that forms a bottom surface for the plurality of wells and that seals the multi-well plate-based pumpless perfusion culture device;

(vii) a rocking platform for holding the multi-well plate, characterized by rocking speed and an adjustable rocking/tilt angle;

wherein the four adjacent sequential wells that comprise the culture chamber comprise an inlet well, a cell seeding port well, a cell chamber well, and an outlet well;

wherein the first micropatterned PSA layer is effective to maintain stable liquid droplets and to prevent medium evaporation by covering the inlet well, cell seeding port well, and outlet well of the first polymer layer;

wherein the inlet and outlet wells are configured as reservoirs for culture medium and to generate a hydrostatic pressure differential between the wells;

wherein the cell seeding port is adapted to receive a biological sample of cells;

wherein a first polymer membrane between the second micropatterned PSA layer and third micropatterned PSA layer is effective to cover the inlet well and to control the flow rate of medium in the culture chamber;

wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber;

wherein the microfluidic device is effective to control flow of minute amounts of the liquids, nutrients and dissolved gas molecules in the MM cancer niche;

wherein the ex vivo MM cancer niche is responsive to changing conditions of perfusion of the ex vivo MM cancer niche by the minute amounts of liquids, nutrients and dissolved gas molecules in the microfluidic device; and wherein formation of an ex vivo MM microenvironment in the microfluidic device is effective to recapitulate spatial and temporal characteristics of a multiple myeloma cancer niche in vivo and to maintain viability of the MM cells in the MM cancer niche in the microfluidic device ex vivo.

According to some embodiments, the multiwell plate-based microfluidic perfusion culture device is effective to model multi-cellular microenvironments. According to some embodiments, the multiwell plate-based microfluidic perfusion culture device is effective to model perfusion effects on cell interactions. According to some embodiments, the multiwell plate-based microfluidic perfusion culture device is effective to model perfusion-induced shear stress on cell responses.

According to some embodiments, the biospecimen comprising human myeloma cells further comprises human plasma autologous to the human myeloma cells. According to some embodiments, the microenvironment perfused by nutrients and dissolved gas molecules of the ex vivo bone marrow (BM) niche is effective for propagation of the human myeloma cells. According to some embodiments, the MM niche further comprises osteoblast-secreted and MM cell-secreted soluble cytokines and growth factors. According to some embodiments, the MM cells are adherent to osteoblasts of the BM niche. According to some embodiments, the MM cells adhere to the osteoblasts of the BM niche by cell-cell interaction. According to some embodiments, the human myeloma cells are cellular components of a bone marrow aspirate. According to some embodiments, the human myeloma cells are cellular components of peripheral blood. According to some embodiments, the human myeloma cells are cellular components of a core biopsy. According to some embodiments, the ex vivo multiple myeloma (MM) cancer niche is effective for propagation of the human myeloma cells for at least 4 days. According to some embodiments, the ex vivo multiple myeloma (MM) cancer niche is effective for propagation of the human myeloma cells for about 1 day to about 30 days, including, for example, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 25 days, or about 30 days. According to some embodiments, the ex vivo multiple myeloma (MM) cancer niche is effective for propagation of the human myeloma cells for at least about 4 days to at least about 3 weeks. According to some embodiments, the ex vivo multiple myeloma (MM) cancer niche is effective to maintain the viability and proliferative capacity of patient-derived MM cells for at least 3 weeks. According to some embodiments, the ex vivo multiple myeloma (MM) cancer niche is effective to maintain the viability and proliferative capacity of patient-derived MM cells for at least about 1 day to at least about 4 weeks, including, for example, at least about 1 day, about 2 days, about 3 days, about 4 days, about 5 days, about 6 days, at least about 1 week, at least about 2 weeks, at least about 3 weeks, or at least about 4 weeks. According to some embodiments, the sample of human myeloma cells added to the BM niche constitutes $1\times10^4$ to $1\times10^5$ mononuclear cells. According to some embodiments, the sample of human myeloma cells added to the BM niche constitutes about $1\times10^4$ mononuclear cells, about $2\times10^4$ mononuclear cells, about $3\times10^4$ mononuclear cells, about $4\times10^4$ mononuclear cells, about $5\times10^4$ mononuclear cells, about $6\times10^4$ mononuclear cells, about $7\times10^4$ mononuclear cells, about $8\times10^4$ mononuclear cells, about $9\times10^4$ mononuclear cells, about or about $1\times10^5$ mononuclear cells. According to some embodiments, propagation of the MM cells is capable of producing deterioration of the 3D ossified tissue of the BM niche.

According to another embodiment, the ex vivo multiple myeloma (MM) cancer niche is prepared by:

(a) constructing an ex vivo bone marrow microenvironment perfused by nutrients and dissolved gas molecules (bone marrow niche) in the microfluidic device by:

(i) seeding a surface of the microfluidic device with viable osteoblasts; and (ii) culturing the cells to form 3D nodular structures that comprise a 3D bone-like tissue:

the 3D bone-like tissue being characterized by an extracellular matrix secreted by the viable adherent osteoblasts;

(b) preparing a multiple myeloma tumor biospecimen composition comprising viable human multiple myeloma cells from a subject and plasma autologous to the subject; and (c) seeding the ex vivo bone marrow microenvironment perfused by nutrients and dissolved gas molecules with the MM tumor biospecimen, and forming an ex vivo microenvironment in the microfluidics device effective to recapitulate spatial and temporal characteristics of a multiple myeloma cancer niche in vivo and to maintain viability of the MM cells in the MM cancer niche in the microfluidics device ex vivo;

wherein the microfluidic device is effective to control flow of minute amounts of the liquids, nutrients and dissolved gas molecules in the MM cancer niche;

wherein the ex vivo MM cancer niche in the microfluidic device is responsive to changing conditions of perfusion of the ex vivo MM cancer niche by the minute amounts of liquids, nutrients and dissolved gas molecules in the microfluidics device.

According to some embodiments of the method, the MM niche further comprises osteoblast-secreted and MM cell-secreted soluble cytokines and growth factors. According to some embodiments, the MM cells are adherent to osteoblasts of the BM niche. According to some embodiments, the MM cells adhere to the osteoblasts of the BM niche by cell-cell interaction. According to some embodiments, the human myeloma cells are cellular components of a bone marrow aspirate. According to some embodiments, the human myeloma cells are cellular components of peripheral blood. According to some embodiments, the human myeloma cells are cellular components of a core biopsy. According to some embodiments, the ex vivo multiple myeloma (MM) cancer niche is effective for propagation of the human myeloma cells for at least 4 days. According to some embodiments, the ex vivo multiple myeloma (MM) cancer niche is effective to maintain the viability and proliferative capacity of patient-derived MM cells for at least 3 weeks. According to some embodiments, the sample of human myeloma cells added to the BM niche constitutes $1\times10^4$ to $1\times10^5$ mononuclear cells. According to some embodiments, the sample of human myeloma cells added to the BM niche constitutes about $1\times10^4$ mononuclear cells, about $2\times10^4$ mononuclear cells, about $3\times10^4$ mononuclear cells, about $4\times10^4$ mononuclear cells, about $5\times10^4$ mononuclear cells, about $6\times10^4$ mononuclear cells, about $7\times10^4$ mononuclear cells, about $8\times10^4$ mononuclear cells, about $9\times10^4$ mononuclear cells, about or about $1\times10^5$ mononuclear cells. According to some embodiments, propagation of the MM cells is effective to produce deterioration of the 3D ossified tissue of the BM niche.

III. A Method for Assessing Chemotherapeutic Efficacy of a Test Chemotherapeutic Agent on Viable Human Multiple Myeloma Cells According to another aspect, the described invention provides a method for assessing chemotherapeutic efficacy of a test chemotherapeutic agent on viable human multiple myeloma cells seeded in an ex vivo microenvironment effective to recapitulate spatial and temporal characteristics of a multiple myeloma cancer niche and to maintain viability of the myeloma cells (MM cancer niche) obtained from a subject comprising:

(a) preparing an in vitro microfluidic device comprising, from top to bottom:

(i) a bottomless multi-well plate comprising a plurality of bottomless wells, wherein four adjacent sequential wells comprise a culture chamber;

(ii) a first micropatterned pressure-sensitive adhesive (PSA) layer attached to a bottom surface of the culture chamber;

(iii) a polymer layer comprising four holes vertically aligned with the four adjacent sequential wells of the culture chamber, the polymer layer being attached to a bottom surface of the first micropatterned PSA layer;

(iv) a second micropatterned PSA layer attached to a bottom surface of the polymer layer;

(v) a third micropatterned PSA layer that connects the four adjacent sequential wells, wherein the third micropatterned PSA layer is attached to a bottom surface of the second micropatterned PSA layer;

(vi) a transparent, optical grade glass layer attached to the bottom surface of the third micropatterned PSA layer that forms a bottom surface for the plurality of wells and that seals the multi-well plate-based pumpless perfusion culture device;

(vii) a rocking platform for holding the multi-well plate, characterized by rocking speed and an adjustable rocking/tilt angle;

wherein the four adjacent sequential wells that comprise the culture chamber comprise an inlet well, a cell seeding port well, a cell chamber well, and an outlet well;

wherein the first micropatterned PSA layer is effective to maintain stable liquid droplets and to prevent medium evaporation by covering the inlet well, cell seeding port well, and outlet well of the first polymer layer;

wherein the inlet and outlet wells are configured as reservoirs for culture medium and to generate hydrostatic pressure differential between the wells;

wherein the cell seeding port is adapted to receive a biological sample of cells;

wherein a first polymer membrane between the second micropatterned PSA layer and third micropatterned PSA layer is effective to cover the inlet well and to control the flow rate of medium in the culture chamber;

wherein a second polymer membrane between the second micropatterned PSA layer and third micropatterned PSA layer is effective to cover the cell chamber well and to hold the medium within the culture chamber during cell seeding and culture; and wherein the second micropatterned PSA layer is effective to adhere and seal the first and second polymer membranes in the culture chamber;

(b) constructing an ex vivo bone marrow microenvironment perfused by nutrients and dissolved gas molecules (bone marrow niche) by (1) seeding a surface of the culture chamber of the in vitro microfluidic device of (a) with a population of cells comprising osteoblasts;

(2) culturing the cells with a culture medium through the channel region for a time effective for the cells to form a confluent layer on the bottom surface of the channel, to then form multiple cell layers and to then form 3D nodular structures that comprise a 3D bone-like tissue;

the 3D bone like tissue being characterized by a mineralized bone-like tissue comprising (a) viable osteoblasts self-organized into cohesive multiple cell layers and (b) an extracellular matrix secreted by the viable adherent osteoblasts;

(c) preparing a multiple myeloma tumor biospecimen composition by:

(1) acquiring a multiple myeloma tumor biospecimen from the subject, wherein the biospecimen comprises viable multiple myeloma cells; and (2) adding plasma autologous to the subject to the viable multiple myeloma cells;

(3) bringing the biospecimen composition of (c)(2) comprising viable MM cells in contact with the osteoblasts of the ex vivo bone marrow microenvironment perfused by nutrients and dissolved gas molecules to seed the ex vivo bone marrow microenvironment with the viable MM cells, the ex vivo bone marrow microenvironment perfused by nutrients and dissolved gas molecules and the seeded MM cells in contact with the osteoblasts of the ex vivo bone marrow microenvironment forming an ex vivo microenvironment effective to recapitulate spatial and temporal characteristics of a multiple myeloma cancer niche and to maintain viability of the human MM cells (MM cancer niche); and (d) testing chemotherapeutic efficacy of a chemotherapeutic agent on the viable human MM cells maintained in the ex vivo MM cancer niche of (c)(3) in the test chamber of (a) by (1) contacting the ex vivo MM cancer niche comprising viable human myeloma cells with a test chemotherapeutic agent; and (2) comparing at least one of viability and level of apoptosis of the MM cells in the MM cancer niche in the presence of the test chemotherapeutic agent to an untreated control; and (e) initiating therapy to treat the MM in the patient with the test chemotherapeutic agent if the test chemotherapeutic agent is effective to significantly ($P<0.05$) reduce viability of the MM cells or to increase apoptosis of the MM cells, compared to the untreated control.

The term "chemotherapy", in its most general sense, refers to the treatment of disease by means of chemical substances or drugs. In popular usage, it refers to antineoplastic drugs used alone or in combination as a cytotoxic standardized regimen to treat cancer. In its non-oncological use, "chemotherapy" may refer, for example, to antibiotics.

Chemotherapy is employed as part of a multimodality approach to the initial treatment of many tumors, including, but not limited to, MM, breast cancer, colon cancer and locally advanced stages of head and neck, lung, cervical, and esophageal cancer, soft tissue sarcomas, pediatric solid tumors and the like. The basic approaches to cancer treatment are constantly changing. Newer therapies have improved patient survival, and, in some cases, turned cancer into a chronic disease.

The majority of chemotherapeutic drugs can be divided into several categories including, but not limited to, (1) alkylating agents; (2) antimetabolites; (3) natural products; (4) hormones and related agents; (5) biologics; (6) miscellaneous agents; and (7) those effective in treating MM.

1. Alkylating Agents and Their Side-Effects

Alkylating agents used in chemotherapy encompass a diverse group of chemicals that have in common the capacity to contribute, under physiological conditions, alkyl groups to biologically vital macromolecules, such as DNA. For several of the most valuable agents, such as cyclophosphamides and nitrosoureas, the active alkylating moieties are generated in vivo after complex metabolic reactions.

As shown in Table 3, there are five major types of alkylating agents used in chemotherapy of neoplastic diseases: (1) nitrogen mustards; (2) ethylenimines; (3) alkyl sulfonates; (4) nitrosoureas; and (5) triazenes.

This results in the formation of covalent linkages by alkylation of various nucleophilic moieties, such as phosphate, amino, sulfhydryl, hydroxyl, carboxyl, and imidazole groups. The chemotherapeutic and cytotoxic effects of alkylating agents are related directly to alkylation of DNA, which has several sites that are susceptible to the formation of a covalent bond.

The most important pharmacological actions of alkylating agents are those that disturb DNA synthesis and cell division. The capacity of these drugs to interfere with DNA integrity and function in rapidly proliferating tissues provides the basis for their therapeutic applications and for many of their toxic properties. Whereas certain alkylating agents may have damaging effects on tissues with normally low mitotic indices, such as the liver, kidney, and mature lymphocytes, they are most cytotoxic to rapidly proliferating tissues in which a large proportion of the cells are in division. These alkylating compounds may readily alkylate nondividing cells, but their cytotoxicity is enhanced markedly if DNA is damaged in cells programmed to divide. In

TABLE 3

Examples of Alkylating Agents Useful for Treating Neoplastic Diseases

| Type of Agent | Example | Neoplasms/Disease | Proposed Mechanism of Action |
| --- | --- | --- | --- |
| Nitrogen Mustard | Cyclophosamide (Cytoxan ®) | Breast cancer; different types of leukemia including acute lymphoblastic leukemia ("ALL"), acute myeloid leukemia ("AML"), chronic lymphocytic leukemia ("CLL"), and chronic myelogenous leukemia ("CML"); Hodgkin lymphoma; multiple myeloma; mycosis fungoides; neuroblastoma; non-Hodgkin lymphoma; ovarian cancer; and retinoblastoma | In the liver, cyclophosphamide is converted to the active metabolites aldophosphamide and phosphoramide mustard, which bind to DNA, thereby inhibiting DNA replication and initiating cell death |
| Nitrogen Mustard | Ifosamide (Mitoxana ®, Ifex ®) | Acute and chronic lymphocytic leukemias; Hodgkin's disease; non-Hodgkin's lymphomas; multiple myeloma; neuroblastoma; breast, ovary, lung cancer; Wilm's tumor; cervix, testis cancer; soft-tissue sarcomas | Alkylates and forms DNA crosslinks, thereby preventing DNA strand separation and DNA replication |
| Nitrogen Mustard | Melphalan (L-sarcolysin; Alkeran ®) | Multiple myeloma; breast, ovarian cancer | Alkylates DNA at the N7 position of guanine and induces DNA interstrand cross-linkages, resulting in the inhibition of DNA and RNA synthesis and cytotoxicity against both dividing and non-dividing tumor cells |
| Alkyl Sulfonate | Busulfan (Myleran ®) | Chronic granulocytic leukemia | Appears to act through the alkylation of DNA |
| Nitrosourea | Carmustine (BiCNU ®; Gliadel Wafer ®) | Hodgkin's disease, non-Hodgkin's lymphomas, primary brain tumors, multiple myeloma, malignant myeloma | Alkylates and cross-links DNA during all phases of the cell cycle, resulting in disruption of DNA function, cell cycle arrest, and apoptosis. This agent also carbamoylates proteins, including DNA repair enzymes, resulting in an enhanced cytotoxic effect |
| Triazene | Temozolomide (Temodar ®) | Glioma; malignant melanoma | Temozolomide is converted at physiologic pH to the short-lived active compound, monomethyl triazeno imidazole carboxamide (MTIC). The cytotoxicity of MTIC is due primarily to methylation of DNA which results in inhibition of DNA replication |

Chemotherapeutic alkylating agents become strong electrophiles through the formation of carbonium ion intermediates or of transition complexes with the target molecules. contrast to many other antineoplastic agents, the effects of the alkylating drugs, although dependent on proliferation, are not cell-cycle-specific, and the drugs may act on cells at any stage of the cycle. However, the toxicity is usually expressed when the cell enters the S phase and the progression through the cycle is blocked. DNA alkylation itself may not be a lethal event if DNA repair enzymes can correct the lesions in DNA prior to the next cellular division.

Alkylating agents differ in their patterns of antitumor activity and in the sites and severity of their side effects. Most cause dose-limiting toxicity to bone marrow elements and to intestinal mucosa and alopecia. Most alkylating agents, including nitrogen mustard, melphalan, chloramucil, cyclophosphamide, and ifosfamide, produce an acute myelosuppression. Cyclophosphamide has lesser effects on peripheral blood platelet counts than do other alkylating agents. Busuflan suppresses all blood elements and may produce a prolonged and cumulative myelosuppression lasting months. BCNU and other chloroethylnitrosoureas cause delayed and prolonged suppression of both platelets and granulocytes.

Alkylating agents also suppress both cellular and humoral immunity, although immunosuppression is reversible at doses used in most anticancer protocols.

In addition to effects on the hematopoietic system, alkylating agents are highly toxic to dividing mucosal cells. The mucosal effects are particularly significant in high-dose chemotherapy protocols associated with bone marrow reconstitution; they may predispose a patient to bacterial sepsis arising from the gastrointestinal tract. Generally, mucosal and bone marrow toxicities occur predictably with conventional doses of these drugs; however other organ toxicities, although less common, can be irreversible and sometimes lethal. All alkylating agents have caused pulmonary fibrosis.

Heart failure that occurs after high-dose cyclophosphamide, ifosfamide, or mitomycin treatment is manifested by neurohumoral activation without concomitant cardiomyocyte necrosis. Mild functional mitral regurgitation also may develop in cyclophosphamide-treated patients (Zver, S. et al., Intl J. Hematol. 85(5): 408-14 (2007)).

In high-dose protocols, a number of toxicities not seen at conventional doses become dose-limiting. For example, endothelial damage that may precipitate venoocclusive disease of the liver; the nitrosoureas, after multiple cycles of therapy, may lead to renal failure; ifosamide frequently causes a central neurotoxicity (manifest in the form of nausea and vomiting), with seizures, coma and sometimes death. Cyclophosamide and ifosfamide release a nephrotoxic and urotoxic metabolite, acrolein, which causes severe hemorrhagic cystitis, an undesirable effect that in high-dose regimens can be prevented by coadministration of mesna (2-mercaptoethanesulfonate).

The more unstable alkylating agents (particularly nitrogen mustards and the nitrosoureas) have strong vesicant properties, damage veins with repeated use, and if extravasated, produce ulceration.

As a class of drugs, the alkylating agents are highly leukomogenic. Acute nonlymphocytic leukemia may affect up to 5% of patients treated on regimens containing alkylating drugs. Melphalan, the nitrosoureas, and procarbazine have the greatest propensity to cause leukemia. Additionally, all alkylating agents have toxic effects on the male and female reproductive systems.

Examples of alkylating agents include, but are not limited to, cyclophosamide (Cytotaxan®), a synthetic alkylating agent chemically related to the nitrogen mustards; temozolomide (Temodar®), a triazene analog of dacarbazine; busulfan (Myleran®), a synthetic derivative of dimethane sulfonate; ifosfamide (Ifex®), a synthetic analog of cyclophosphamide; mesna (Mesnex®), a sulfhydryl compound; melphalan hydrochloride (Alkeran®), an orally available phenylalanine derivative of nitrogen mustard; and the nitrosoureas carmustine (BiCNU®) and lomustine (CEENU®).

2. Antimetabolites

Antimetabolites are a class of drugs that interfere with DNA and RNA growth by preventing purines (azathioprine, mercaptopurine) or pyrimidine from becoming incorporated into DNA during the S phase of the cell cycle, thus stopping normal development and division. Antimetabolites commonly are used to treat leukemias, tumors of the breast, ovary and the intestinal tract, as well as other cancers.

Antimetabolites include folic acid analogs, such as methotrexate and aminopterin; pyrimidine analogs, such as fluorouracil and fluorodeoxyuridine; cytarabine (cytosine arabinoside); and purine analogs, such as mercaptopurine, thioguanine, fludarabine phosphate, pentostatin (2'-deoxycoformycin), and cladribine. Table 4 presents examples of some antimetabolites useful for treating neoplastic diseases.

TABLE 4

Examples of Antimetabolites Useful for Treating Neoplastic Diseases

| Type of Agent | Example | Neoplasms/Disease | Proposed Mechanism of Action |
| --- | --- | --- | --- |
| Pyrimidine Analog | 5-fluorouracil (fluorouracil; 5-FU) | Palliative treatment of colorectal cancer, breast cancer, stomach cancer, and pancreatic cancer. In combination with other drugs, it is used to treat locally advanced squamous cell carcinoma of the head and neck, gastric adenocarcinoma, and Stage III colorectal cancer | Fluorouracil and its metabolites possess a number of different mechanisms of action. In vivo, fluorouracil is converted to the active metabolite 5-fluoroxyuridine monophosphate (F-UMP); replacing uracil, F-UMP incorporates into RNA and inhibits RNA processing, thereby inhibiting cell growth. Another active metabolite, 5-5-fluoro-2'-deoxyuridine-5'-Omonophosphate (F-dUMP), inhibits thymidylate synthase, resulting in the depletion of thymidine triphosphate (TTP), one of the four nucleotide triphosphates used in the in vivo synthesis of DNA. Other fluorouracil metabolites incorporate into both RNA and DNA; incorporation into RNA results in major effects on both RNA processing and functions |

TABLE 4-continued

Examples of Antimetabolites Useful for Treating Neoplastic Diseases

| Type of Agent | Example | Neoplasms/Disease | Proposed Mechanism of Action |
|---|---|---|---|
| Pyrimidine Analog | Capecitabine (Xeloda ®) | Metastatic (Stage III) colorectal cancer and metastatic breast cancer | As a prodrug, capecitabine is selectively activated by tumor cells to its cytotoxic moiety, 5-fluorouracil (5-FU); subsequently, 5-FU is metabolized to two active metabolites, 5-fluoro-2-deoxyuridine monophosphate (F-dUMP) and 5-fluorouridine triphosphate (FUTP) by both tumor cells and normal cells. F-dUMP inhibits DNA synthesis and cell division by reducing normal thymidine production, while FUTP inhibits RNA and protein synthesis by competing with uridine triphosphate for incorporation into the RNA strand |
| Pyrimidine Analog | Gemcitabine (gemcitabine hydrochloride, Gemzar ®) | Pancreatic cancer, ovarian cancer, breast cancer, and non-small cell lung cancer | Gemcitabine is converted intracellularly to the active metabolites difluorodeoxycytidine di- and triphosphate (dFdCDP, dFdCTP). dFdCDP inhibits ribonucleotide reductase, thereby decreasing the deoxynucleotide pool available for DNA synthesis; dFdCTP is incorporated into DNA, resulting in DNA strand termination and apoptosis |
| Pyrimidine Analog | Floxuridine (FUDR) | Palliative treatment of gastrointestinal adenocarcinoma metastatic to the liver | Inhibits thymidylate synthetase, resulting in disruption of DNA synthesis and cytotoxicity. This agent is also metabolized to fluorouracil and other metabolites that can be incorporated into RNA and inhibit the utilization of preformed uracil in RNA synthesis |
| Purine Analog | 2-chlorodeoxy-adenosine (cladribine, Leustatin ®) | Myelodysplastic syndromes including refractory anemia and chronic myelomonocytic leukemia | Incorporates into DNA and inhibits DNA methyltransferase, resulting in hypomethylation of DNA and intra-S-phase arrest of DNA replication |
| Pyrimidine Analog | Decitabine (Dacogen ®) | Glioma; malignant melanoma | Temozolomide is converted at physiologic pH to the short-lived active compound, monomethyl triazeno imidazole carboxamide (MTIC). The cytotoxicity of MTIC is due primarily to methylation of DNA which results in inhibition of DNA replication |
| Purine Analog | Fludarabine phosphate (Fludara ®) | Refractory B-cell chronic lymphocytic leukemia | Blocks cells from making DNA; purine antagonist and a type of ribonucleotide reductase inhibitor |
| Purine Analog | Mercaptopurine (6-mercaptopurine; 6-MP; Purinethol ®) | Acute lymphocytic, acute granulocytic, and chronic granulocytic leukemias | A thiopurine-derivative antimetabolite with antineoplastic and immunosuppressive activities |
| Purine Analog | 2'-deoxycoformycin (Nipent ®, pentostatin) | Hairy cell laukemia | Binds to and inhibits adenine deaminase (ADA), an enzyme essential to purine metabolism |
| Purine Analog | Dacarbazine (DTIC-Dome ®) | Metastatic melanoma, Hodgkin's lymphoma | Alkylates and cross-links DNA during all phases of the cell cycle, resulting in disruption of DNA function, cell cycle arrest, and apoptosis |
| Folic Acid Analog | Pemetrexed disodium (Alimta ®) | Mesothelioma, non-small cell lung cancer | Binds to and inhibits the enzyme thymidylate synthase (TS) which catalyses the methylation of 2'-deoxyuridine-5'-monophosphate (dUMP) to 2'-deoxythymidine-5'-monophosphate (dTMP), an essential precursor in DNA synthesis |
| Folic Acid Analog | Methotrexate (methotrexate sodium, amethopterin, | Chorioadenoma destruens, choriocarcinoma, acute lymphoblastic leukemia, breast cancer, lung cancer, certain | Binds to and inhibits the DHFR, resulting in inhibition of purine nucleotide and thymidylate synthesis and, subsequently, |

TABLE 4-continued

Examples of Antimetabolites Useful for Treating Neoplastic Diseases

| Type of Agent | Example | Neoplasms/Disease | Proposed Mechanism of Action |
| --- | --- | --- | --- |
| | Folex ®, Mexate ®, Rheumatrex ®) | types of head and neck cancer, advanced non-Hodgkin lymphoma, and osteosarcoma; rheumatoid arthritis and psoriasis | inhibition of DNA and RNA syntheses |
| Cytidine analog | Cytarabine (cytosine arabinoside) | Acute non-lymphatic leukemia, acute lymphocytic leukemia, blast phase chronic myelocytic leukemia | Antimetabolite analog of cytidine with a modified sugar moiety (arabinose instead of ribose). Cytarabine is converted to the triphosphate form within the cell and then competes with cytidine for incorporation into DNA. Because the arabinose sugar sterically hinders the rotation of the molecule within DNA, DNA replication ceases, specifically during the S phase of the cell cycle. This agent also inhibits DNA polymerase, resulting in a decrease in DNA replication and repair |

2.1. Anti-Folates and Their Side-Effects

Folic acid is an essential dietary factor from which is derived a series of tetrahydrofolate cofactors that provide single carbon groups for the synthesis of precursors of DNA (thymidylate and purines) and RNA (purines). The enzyme dihydrofolate reductase ("DHFR") is the primary site of action of most anti-folates. Inhibition of DHFR leads to toxic effects through partial depletion of tetrahydrofolate cofactors that are required for the synthesis of purines and thymidylate.

Examples of anti-folates include, but are not limited to, methotrexate and Pemetrexed disodium. The most commonly used anti-folate is methotrexate (methotrexate sodium, amethopterin, Folex®, Mexate®, Rheumatrex®), which is an antimetabolite and antifolate agent with antineoplastic and immunosuppressant activities. Pemetrexed disodium (Alimta®) is the disodium salt of a synthetic pyrimidine-based antifolate.

2.2. Pyrmidine Analogs and Their Side-Effects

Pyrmidine analogs are a diverse group of drugs with the capacity to inhibit biosynthesis of pyrimidine nucleotides or to mimic these natural metabolites to such an extent that the analogs interfere with the synthesis or function of nucleic acids. Drugs in this group have been employed in the treatment of diverse afflictions, including neoplastic diseases, psoriasis and infections caused by fungi and DNA-containing viruses.

Examples of pyrimidine analogs include, but are not limited to, 5-Fluorouracil (fluorouracil, 5-FU, Adrucil®, Efudex®, Fluorplex®), an antimetabolite fluoropyrimidine analog of the nucleoside pyrimidine with antineoplastic activity; floxuridine, a fluorinated pyrimidine monophosphate analogue of 5-fluoro-2'-deoxyuridine-5'-phosphate (FUDR-MP) with antineoplastic activity; capecitabine (Xeloda®), an antineoplastic fluoropyrimidine carbamate; and gemcitabine hydrochloride (Gemzar®), the salt of an analog of the antimetabolite nucleoside deoxycytidine with antineoplastic activity.

2.3. Purine Analogs and Their Side-Effects

Several analogs of natural purine bases, nucleosides and nucleotides useful in the treatment of malignant diseases (mercaptopurine, thioguanine) and for immunosuppressive (azatioprine) and antiviral (acyclovir, ganciclovir, vidarabine, zidovudine) therapies have been identified.

The purine analogs mercaptopurine and its derivative azatioprine are among the most clinically useful drugs of the antimetabolite class. Examples of purine analogs include, but are not limited to, mercaptopurine (Purinethol®), a thiopurine-derivative antimetabolite with antineoplastic and immunosuppressive activities; decitabine (Dacogen®), a cytidine antimetabolite analogue with potential antineoplastic activity; and dacarbazine (DTIC-DOME®), a triazene derivative with antineoplastic activity.

3. Natural Products and Their Side-Effects

Many chemotherapeutic agents are found or derived from natural resources. Table 5 shows examples of chemotherapeutic drugs classified as natural products.

TABLE 5

Examples of Natural Products Useful for Treating Neoplastic Diseases

| Type of Agent | Example | Neoplasms/Disease | Proposed Mechanism of Action |
| --- | --- | --- | --- |
| *Vinca* Alkaloid | Vincristine (vincristine sulfate) | Acute lymphocytic leukemia, neuroblastoma, Wilm's tumor, rhabdomyosarcoma, Hodgkin's disease, non-Hodgkin's lymphomas, small-cell lung cancer | Binds irreversibly to microtubules and spindle proteins in S phase of the cell cycle and interferes with the formation of the mitotic spindle, thereby arresting tumor cells in metaphase |

TABLE 5-continued

Examples of Natural Products Useful for Treating Neoplastic Diseases

| Type of Agent | Example | Neoplasms/Disease | Proposed Mechanism of Action |
|---|---|---|---|
| *Vinca* Alkaloid | Vinblastine (vinblastine sulfate, VLB) | Hodgkin's disease, non-Hodgkin's lymphomas, breast and testis cancer | Binds to tubulin and inhibits microtubule formation, resulting in disruption of mitotic spindle assembly and arrest of tumor cells in the M phase of the cell cycle |
| *Vinca* Alkaloid | Vinorelbine tartrate (Navelbine ®) | Advanced non-small cell lung cancer | Binds to tubulin, thereby inhibiting tubulin polymerization into microtubules and spindle formation and resulting in apoptosis of susceptible cancer cells |
| Taxane | Paclitaxel (Taxol ®) | Ovarian, breast, lung, head and neck cancer; used in combination therapy of cisplatin-refractory ovarian, breast, (non-small cell) lung, esophagus, bladder, and head and neck cancers | Inhibitor of mitosis, differing from the *vinca* alkaloids and colchicine derivatives in that it promotes rather than inhibits microtubule formation |
| Epothilone | Ixabepilone (Ixempra ®, INN, azaepothilone B) | Non-Hodgkin's lymphoma; breast cancer | Binds to tubulin and promotes tubulin polymerization and microtubule stabilization, thereby arresting cells in the G2-M phase of the cell cycle and inducing tumor cell apoptosis |
| Anthracycline | Daunorubicin (Cerubidine ®, daunomycin, rubidomycin) | Acute granulocytic and acute lymphocytic leukemias | Daunombicin exhibits cytotoxic activity through topoisomerase-mediated interaction with DNA, thereby inhibiting DNA replication and repair and RNA and protein synthesis |
| Anthracycline | Epirubicin (Ellence ®) | Breast cancer | Intercalates into DNA and interacts with topoisomerase II, thereby inhibiting DNA replication and repair and RNA and protein synthesis |
| Anthracycline | Doxorubicin (Doxil ®, doxorubicin hydrochloride, Adriamycin ®, Rubex ®) | Soft-tissue, osteogenic, and other sarcomas; Hodgkin's disease, non-Hodgkin's lymphomas; acute leukemias; breast, genitourinary, thyroid, lung, stomach cancer; neuroblastoma | Intercalates between base pairs in the DNA helix, thereby preventing DNA replication and ultimately inhibiting protein synthesis; inhibits topoisomerase II which results in an increased and stabilized cleavable enzyme-DNA linked complex during DNA replication and subsequently prevents the ligation of the nucleotide strand after double-strand breakage |
| Anthracycline | Idarubicin (idarubicin hydrochloride, Idamycin PFS ®) | Acute myeloid leukemia | Intercalates into DNA and interferes with the activity of topoisomerase II, thereby inhibiting DNA replication, RNA transcription and protein synthesis |
| Anthracenedione | Mitoxantrone (Novantrone ®) | Acute granulocytic leukemia, breast and prostate cancer | Stimulates the formation of stand breaks in DNA (mediated by topoisomerase II) and also intercalating with DNA |
| Antibiotic | Mitomycin (mitocyin C; Mutamycin ®) | Stomach, cervix, colon, breast, pancreas, bladder, head and neck cancers | Bioreduced mitomycin C generates oxygen radicals, alkylates DNA, and produces interstrand DNA cross-links, thereby inhibiting DNA synthesis. Preferentially toxic to hypoxic cells, mitomycin C also inhibits RNA and protein synthesis at high concentrations |
| Camptothecin | Irinotecan (Camptosar ®, irinotecan hydrochloride | Ovarian cancer, small cell lung cancer, colon cancer | Prodrug is converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death |

TABLE 5-continued

Examples of Natural Products Useful for Treating Neoplastic Diseases

| Type of Agent | Example | Neoplasms/Disease | Proposed Mechanism of Action |
| --- | --- | --- | --- |
| Epipodophyllotoxin | Etoposide (VePesid ®) | Testis, small cell lung and other lung, breast cancer, Hodgkin's disease, non-Hodgkin's lymphomas, acute granulocytic leukemia, Kaposi's sarcoma | Binds to and inhibits topoisomerase II and its function in ligating cleaved DNA molecules, resulting in the accumulation of single- or double-stranded DNA breaks, the inhibition of DNA replication and transcription, and apoptotic cell death |
| Epipodophyllotoxin | Teniposide (Vumon CO) | Testis, small-cell lung and other lung, breast cancer; Hodgkin's disease, non-Hodgkin's lymphomas, acute granulocytic leukemia, Kaposi's sarcoma | Forms a ternary complex with the enzyme topoisomerase II and DNA, resulting in dose-dependent single- and double-stranded breaks in DNA, DNA: protein cross-links, inhibition of DNA strand religation, and cytotoxicity |
| Epipodophyllotoxin | Etoposide phosphate (Etopophos ®) | Testicular tumors, small cell lung cancer | Binds to the enzyme topoisomerase II, inducing double-strand DNA breaks, inhibiting DNA repair, and resulting in decreased DNA synthesis and tumor cell proliferation. Cells in the S and G2 phases of the cell cycle are most sensitive to this agent. |
| Antibiotic | Amphotericin B | Induction chemotherapy for childhood acute leukemia | Binds to ergosterol, an essential component of the fungal cell membrane, resulting in depolarization of the membrane; alterations in cell membrane permeability and leakage of important intracellular components; and cell rupture. This agent may also induce oxidative damage in fungal cells and has been reported to stimulate host immune cells |

3.1. Antimitotic Drugs 3.1.1. Vinca Alkaloids and Their Side-Effects

The vinca alkaloids, cell-cycle-specific agents that, in common with other drugs, such as colchicine, podophyllotoxin, and taxanes, block cells in mitosis, exerts their biological activities by specifically binding to tubulin, thereby blocking the ability of protein to polymerize into microtubules, and arresting cell division in metaphase through disruption of the microtubules of the mitotic apparatus. In the absence of an intact mitotic spindle, the chromosomes may disperse throughout the cytoplasm or may clump in unusual groupings. Both normal and malignant cells exposed to vinca alkaloids undergo changes characteristic of apoptosis.

Examples of vinca alkaloids include, but are not limited to, vincristine sulfate, a salt of a natural alkaloid isolated from the plant Vinca rosea Linn; vinblastine, a natural alkaloid isolated from the plant Vinca rosea Linn; and vinorelbine. Both vincristine and vinblastine, as well as the analog vinorelbine, have potent and selective antitumor effects, although their actions on normal tissue differ significantly.

3.1.2. Taxanes

The taxanes include, for example, but not limited to, paclitaxel, extracted from the Pacific yew tree *Taxus brevifolia*, and docetaxel (Taxotere®), a semi-synthetic, second-generation taxane derived from a compound found in the European yew tree *Taxus baccata*.

3.2. Epipodophyllotoxins and Their Side-Effects

Podophyllotoxin is the active principle extracted from the mandrake plant *Podophyllum peltatum* from which two semisynthetic glycosides, etoposide and teniposide, have been developed.

3.3. Camptothecin Analogs and Their Side-Effects

Camptothecins target the enzyme topoisomerase I. The parent compound, camptothecin, was first isolated from the Chinese tree *Camptotheca acuminata*. Although the parent camptothecin compound demonstrated antitumor activity, its severe and unpredictable toxicity, principally myelosuppression and hemorrhagic cystitis limited its use. The most widely used camptothecin analogs are irinotecan and toptecan, which are less toxic and more soluble.

3.4. Anti-Tumor Antibiotics

Antitumor antibiotics are compounds that have cytotoxic as well as antimicrobial properties. Most commonly used in neoplastic disease treatment are the actinomycins and anthracyclines.

3.4.1. Actinomycin

An exemplary actinomycin includes Dactinomycin (Actinomycin D), produced by *Streptomyces parvullus*. This highly toxic agent inhibits rapidly proliferating cells of normal and neoplastic origin.

3.4.2. Anthracyclines

The anthracycline antibiotics and their derivatives are produced by the fungus *Streptomyces peucetius* var. *caesius*. Anthracyclines and anthracenediones can intercalate with DNA. Accordingly, many functions of DNA are affected, including DNA and RNA synthesis. Single-strand and double-strand breaks occur, as does sister chromatid exchange; thus these compounds are both mutagenic and carcinogenic. Scission of DNA is believed to be mediated by drug binding to DNA and topoisomerase II that prevents the resealing of DNA breaks created by the enzyme.

Examples of anthracyclines include, but are not limited to, idarubicin hydrochloride, a semisynthetic 4-demethoxy analog of daunorubicin (daunorubicin hydrochloride, daunomycin, rubidomycin; Cerubidine®); doxorubicin (doxorubicin hydrochloride, Adriamycin®, Rubex®); as well as several analogs of doxorubicin including valrubicin (Valstar®) (for intravescial therapy of BCG-refractory urinary bladder carcinoma) and epirubicin (4'-epidxorubicin, Ellence®) (as a component of adjuvant therapy following resection of early lymph-node-positive breast cancer).

Additional antibiotic antineoplastics include, but are not limited to, mitoxantrone (Novotrone®), an anthracenedione; and bleomycin antibiotics, fermentation products of *Streptomyces verticillus* that cleave DNA, and includes bleomycin sulfate (Blenoxane®); and mitomycin (mitomycin-C, Mutamycin®), an antibiotic isolated from *Streptomyces caespitosus*.

4. Biologics

Generally, the term "biologics" as used herein refers to compounds that are produced by biological processes, including those utilizing recombinant DNA technology. Biologic compounds include agents or approaches that beneficially affect a patient's biological response to a neoplasm. Included are agents that act indirectly to mediate their anti-tumor effects (e.g., by enhancing the immunological response to neoplastic cells) or directly on the tumor cells (e.g., differentiating agents). Table 6 shows examples of chemotherapeutic agents that are classified as biologics.

TABLE 6

Examples of Biologics Useful for Treating Neoplastic Diseases

| Type of Agent | Example | Neoplasms/Disease | Proposed Mechanism of Action |
|---|---|---|---|
| Granulocyte-Colony Stimulating Factor | Filgrastim (Neupogen ®) | Neutropenia | In vitro, G-CSF expands the population of neutrophil granulocyte precursors, augments granulocyte function by enhancing chemotaxis and antibody-dependent cellular cytotoxicity, and enhances the mobilization of stem cells in the peripheral blood following cytotoxic chemotherapy |
| Monoclonal Antibody | Bevacizumab (Avastin ®) | Colorectal cancer, non-small cell lung cancer, breast cancer | Binds to and inhibits the biologic activity of human vascular endothelial growth factor ("VEGF") |
| Granulocyte-Macrophage Colony Stimulating Factor | Sargramostim (Leukine ®) | Acute myelogenous leukemia, mobilization and engraftment of peripheral blood progenitor cells | Used following induction chemotherapy in patients with acute myelogenous leukemia (AML) to shorten the time to neutrophil recovery and to reduce the incidence of severe and life-threatening infections; rescue bone marrow graft failure or speed graft recovery in patients undergoing autologous bone marrow transplantation |
| HER2/neu receptor antagonist | Trastuzumab (Herceptin ®) | Adenocarcinomas, breast cancer | Recombinant humanized monoclonal antibody directed against the human epidermal growth factor receptor 2 (HER2). After binding to HER2 on the tumor cell surface, trastuzumab induces an antibody-dependent cell-mediated cytotoxicity against tumor cells that overexpress HER2. HER2 is overexpressed by many adenocarcinomas, particularly breast adenocarcinomas |
| Therapeutic peptide | Interferon α-2b (Intron ® A) | Hairy cell leukemia, malignant melanoma, follicular lymphoma, condylomata acuminata, chronic hepatitis C and B | Cytokines produced by nucleated cells (predominantly natural killer (NK) leukocytes) upon exposure to live or inactivated virus, double-stranded RNA or bacterial products. These agents bind to specific cell-surface receptors, resulting in the transcription and translation of genes containing an interferon-specific response element. The proteins so produced mediate many complex effects, including antiviral effects (viral protein synthesis); antiproliferative effects (cellular growth inhibition and alteration of cellular differentiation); anticancer effects (interference with oncogene expression); and immune-modulating effects (NK cell activation, alteration of cell surface antigen expression, and augmentation of lymphocyte and macrophage cytotoxicity |
| Therapeutic peptide | Interferon β-1b (Betaseron ®, Rebif ®) | Relapsing multiple sclerosis | Chemically identical to or similar to endogenous interferon beta with antiviral and anti-tumor activities. Endogenous interferons beta are cytokines produced by nucleated cells (predominantly natural killer cells) upon exposure to live or inactivated virus, double-stranded RNA or bacterial products. These agents bind to specific cell-surface receptors, resulting in the transcription and translation of genes with an interferon-specific response element. The proteins so produced mediate many complex effects, including antiviral (the most important being inhibition of viral protein synthesis), antiproliferative and immune modulating effects |

TABLE 6-continued

Examples of Biologics Useful for Treating Neoplastic Diseases

| Type of Agent | Example | Neoplasms/Disease | Proposed Mechanism of Action |
| --- | --- | --- | --- |
| IL-2 product | Aldesleukin (Proleukin ®) | Metastatic renal cell carcinoma, metastatic melanoma | Possesses the biological activities of human native IL-2 |
| Monoclonal antibody | Alemtuzumab (Campath ®) | B-cell chronic lymphocytic leukemia | CD52-directed cytolytic antibody |

Examples of antineoplastic biologics include, but are not limited to, Filgrastim (Neupogen®), a recombinant granulocyte colony-stimulating factor (G-CSF); and Sargramostim (Leukine®), a recombinant granulocyte/macrophage colony-stimulating factor (GM-CSF).

The term "monoclonal antibodies" ("mAb") generally refers to identical monospecific immunoglobulin molecules derived from a laboratory procedure from a single cell clone that are capable of binding to an agonist. Fully human monoclonal antibodies have the amino acid sequence of an immunoglobulin of the human species. "Humanized" monoclonal antibodies are constructed from mouse monoclonal antibodies having the desired specificity, and often have complementarity determining regions of a mouse immunoglobulin while maintaining the framework and constant regions of a human antibody to prevent a human-antimouse neutralizing response.

Examples of antineoplastic monoclonal antibodies include, but are not limited to, Bevacizumab (Avastin®), a recombinant humanized monoclonal IgG1 antibody that binds to and inhibits the biologic activity of human vascular endothelial growth factor ("VEGF") in in vitro and in vivo assay systems, and Panitumumab (Vectibix®), a human monoclonal antibody produced in transgenic mice that attaches to the transmembrane epidermal growth factor (EGF) receptor.

5. Hormones and Related Agents

Several chemotherapeutic agents exert their therapeutic effect through interactions with hormones and related agents. Table 7 shows examples of several chemotherapeutic agents classified as hormone and related agents.

TABLE 7

Examples of Hormones and Antagonists Useful for Treating Neoplastic Diseases

| Type of Agent | Example | Neoplasms/Disease | Proposed Mechanism of Action |
| --- | --- | --- | --- |
| Progestin | Megestrol Acetate (Megace ES ®) | Endometrium, breast cancer; anorexia, cachexia (wasting), or other unexplained weight loss | Mimicking the action of progesterone, megestrol binds to and activates nuclear progesterone receptors (PRs) in the reproductive system and pituitary; ligand-receptor complexes are translocated to the nucleus where they bind to progesterone response elements (PREs) located on target genes. Megestrol's antineoplastic activity against estrogen-responsive tumors may be due, in part, to the suppression of pituitary gonadotropin production and the resultant decrease in ovarian estrogen secretion; interference with the estrogen receptor complex in its interaction with genes and; as part of the progesterone receptor complex, direct interaction with the genome and downregulation of specific estrogen-responsive genes. This agent may also directly kill tumor cells |
| Antiestrogen | Tamoxifen Citrate (Nolvadex ®) | Breast cancer, especially postmenopausal women with estrogen-receptor positive (ER+) metastatic breast cancer or following primary tumor therapy in an adjuvant setting; premenopausal women with ER+ tumors | When bound to the ER, tamoxifen induces a change in the three-dimensional shape of the receptor, inhibiting its binding to the estrogen-responsive element ("ERE") on DNA. Under normal physiological conditions, estrogen stimulation increases tumor cell production of transforming growth factor β("TGF-β"), an autocrine inhibitor of tumor cell growth. "Autocrine signaling" refers to a form of signaling in which a cell secretes a hormone or chemical messenger (autocrine agent) that binds to autocrine receptors on the same cell type, leading to changes in the cells. By blocking these pathways, the net effect of tamoxifen treatment is to decrease the autocrine stimulation of breast cancer growth |

TABLE 7-continued

Examples of Hormones and Antagonists Useful for Treating Neoplastic Diseases

| Type of Agent | Example | Neoplasms/Disease | Proposed Mechanism of Action |
| --- | --- | --- | --- |
| Androgen | Fluoxymesterone (Halotestin ®) | Breast cancer; testosterone replacement therapy in males with primary hypogonadism or hypogonadotrophic hypogonadism, as well as palliation of androgen-responsive recurrent mammary cancer in females | Binds to and activates specific nuclear receptors, resulting in an increase in protein anabolism, a decrease in amino acid catabolism, and retention of nitrogen, potassium, and phosphorous. This agent also may competitively inhibit prolactin receptors and estrogen receptors, thereby inhibiting the growth of hormone-dependent tumor lines |
| Gonadotropin-releasing Hormone Analog | Leuprolide (leuprolide acetate, Eligard ®) | Prostate cancer; endometriosis; anemia secondary to uterine leiomyomas and central precocious puberty | Binds to and activates gonadotropin-releasing hormone (GnRH) receptors. Continuous, prolonged administration of leuprolide in males results in pituitary GnRH receptor desensitization and inhibition of pituitary secretion of follicle stimulating hormone (FSH) and luteinizing hormone (LH), leading to a significant decline in testosterone production; in females, prolonged administration results in a decrease in estradiol production. This agent reduces testosterone production to castration levels and may inhibit androgen receptor-positive tumor progression |
| Somatostatin Analog | Octreotide acetate (Sandostatine LAR Depot ®) | Acromegaly, severe diarrhea/flushing episodes associated with metastatic carcinoid tumors, diarrhea associated with VIP-secreting tumors | Suppresses the luteinizing hormone response to gon adotropin-releasing hormone, decreases splanchnic blood flow, and inhibits the release of serotonin, gastrin, vasoactive intestinal peptide (VIP), secretin, motilin, pancreatic polypeptide, and thyroid stimulating hormone |

5.1. Antiestrogens

Antiestrogens are modulators of the estrogen receptor. Estrogens are the family of hormones that promote the development and maintenance of female sex characteristics. Examples of antiestrogens include, but are not limited to, tamoxifen citrate (Nolvadex®), a competitive inhibitor of estradiol binding to the estrogen receptor ("ER").

5.2. Gonadotropin-Releasing Hormone Analogs

Gonadotropin-releasing hormone ("GnRH") analogs are synthetic peptide drugs modeled after human GnRH. They are designed to interact with GnRH receptor. The analogs of GnRH peptide include leuprolide (Lupron®, Eligard®), go serelin (Zoladex®), triptorelin (Trelstar Depot®) and buserelin (Suprefact®). These compounds have biphasic effects on the pituitary. Initially, they stimulate the secretion of both follicle-stimulating hormone ("FSH") and luteinizing hormone ("LH"). However, with longer-term administration, cells become desensitized to the action of GnRH analogs. As a result, there is inhibition of the secretion of LH and FSH and the concentration of testosterone falls to castration levels in men and estrogen levels fall to postmenopausal values in women.

GnRH analogs have been used to treat prostatic carcinomas. They present several side-effects, including a transient "flare" of disease. Notwithstanding, leuprolide and goserelin have been used for the treatment of metastatic breast cancer. GnRH analogs also have been used in the treatment of endometriosis, anemia secondary to uterine leiomyomas and central precocious puberty. Examples of gonadotropin-releasing hormone analogs include Leuprolide acetate, the salt of a synthetic nonapeptide analog of gonadotropin-releasing hormone.

5.3. Androgens and Antiandrogens

The term "androgen" as used herein refers to any natural or synthetic compound that promotes male characteristics. Examples of antineoplastic androgens include, but are not limited to, fluoxymesterone (Halotestin®), a halogenated derivative of 17-alpha-methyltestosterone.

Antiandrogens are competitive inhibitors that prevent the natural ligands of the androgen receptor from binding to the receptor. These compounds have activity of their own against prostate cancer. They also are effective in preventing the flare reaction induced by the testosterone surge that can occur with GnRH chemotherapy. The antiandrogens may be divided structurally and mechanistically into (1) steroidal and (2) nonsteroidal antiandrogens ("NSAAs"). The steroidal agents have some partial agonist activity at the androgen receptor. These include such compounds as cyproterone acetate (Androcur®) and megestrol acetate ("Megace®). Side-effects include loss of libido, decreased sexual potency, and low testosterone levels. The NSAAs inhibit the translocation of the androgen receptor to the nucleus from the cytoplasm of target cells, thus providing an antiproliferative effect. NSAAs include flutamide (Eulexin®), nilutamide (Nilandron®), and bicalutamide (Casodex®).

Additional antiandrogen agents, include, but are not limited to, megestrol acetate, the salt of megestrol, a synthetic derivative of the naturally occurring female sex hormone progesterone, with progestogenic, antiestrogenic, and antineoplastic activities.

5.4. Somatostatin Analog

Examples of somatostatin analogs include, but are not limited to, octreolide acetate (Sandostatin LAR® Depot), the salt of a synthetic long-acting cyclic octapeptide with pharmacologic properties mimicking those of the natural hormone somatostatin.

6. Miscellaneous Agents

Imatinib mesylate (Gleevec®) inhibits the function of bcr-abl, a constituitively active tyrosine kinase. See, e.g., Kerkeld, R., et al., Nat. Med. 12: 908-16 (2006). Table 8 shows examples of other miscellaneous chemotherapeutic agents for treating neoplastic disease.

TABLE 8

Examples of Miscellaneous Agents Useful for Treating Neoplastic Diseases

| Type of Agent | Example | Neoplasms/Disease | Proposed Mechanism of Action |
|---|---|---|---|
| Kinase inhibitor | Sorafenib (Nexavar ®) | Hepatocellular carcinoma, advanced renal cell carcinoma | Blocks the enzyme RAF kinase, a critical component of the RAF/MEK/ERK-β signaling cascade, thereby blocking tumor angiogenesis |
| Kinase inhibitor | Imatinib mesylate (Gleevec ®) | Myeloid leukemia, lymphoblastic leukemia, myelodysplastic - myeloproliferative diseases | Binds to an intracellular pocket located within tyrosine kinases (TK), thereby inhibiting ATP binding and preventing phosphorylation and the subsequent activation of growth receptors and their downstream signal transduction pathways. This agent inhibits TK encoded by the bcr-abl oncogene as well as receptor TKs encoded by the c-kit and platelet-derived growth factor receptor (PDGFR) oncogenes |
| Kinase inhibitor | Sunitinib malate (Sutent ®) | Gastrointestinal stromal tumor, advanced renal cell carcinoma | |
| HER1/EGFR tyrosine kinase inhibitor | Erlotinib (Tarceva ®) | Non-small cell lung cancer, pancreatic cancer | Competes with ATP to reversibly bind to the intracellular catalytic domain of epidermal growth factor receptor (EGFR) tyrosine kinase, thereby reversibly inhibiting EGFR phosphorylation and blocking the signal transduction events and tumorigenic effects with EGFR activation |
| Platinum Coordination Complex | Cisplatin | Ovarian cancer, non-small cell lung cancer, and small cell lung cancer; cancer of bladder, head and neck, and endometrium | Forms highly reactive, charged platinum complexes which bind to nucleophilic groups such as GC-rich sites in DNA, inducing intrastrand and interstrand DNA crosslinks, as well as DNA-protein cross-links. These cross-links result in apoptosis and cell growth inhibition |
| Platinum Coordination Complex | Carboplatin | Ovarian cancer, non-small cell lung cancer, and small cell lung cancer | When activated, intracellularly forms reactive platinum complexes that bind to nucleophilic groups such as GC-rich sites in DNA, thereby inducing intrastrand and interstrand DNA crosslinks, as well as DNA-protein cross-links. These carboplatin-induced DNA and protein effects result in apoptosis and cell growth inhibition |
| Platinum Coordination Complex | Oxaliplatin (Eloxatin ®) | Advanced metastatic carcinoma of colon or rectum; colon cancer | Alkylates macromolecules, forming both inter- and intra-strand platinum-DNA crosslinks, which result in inhibition of DNA replication and transcription and cell-cycle nonspecific cytotoxicity |
| Synthetic polypeptides | Glatiramer acetate (Copaxone ®) | Multiple sclerosis | Unknown |
| Platelet-reducing Agent | Anagrelide (Agrylin ®, anagrelide hydrochloride) | Thrombocythemia, polycythemia, chronic myelogenous leukemia, other myeloproliferative disorders including myeloid metaplasia with myelofibrosis | Putatively provides dose-related reduction in platelet production resulting from a decrease in megakaryocyte hypermaturation |
| Retinoids | Isotretinoin (Accutane ®) | Severe recalcitrant nodular acne | Binds to and activates nuclear retinoic acid receptors (RARs); activated RARs serve as transcription factors that promote cell differentiation and apoptosis |
| Retinoids | Tretinoin (Vesanoid ®) | Acute promyelocytic leukemia | Induces maturation of acute promyelocytic leukemia |
| Retinoids | Bexarotene (Targretin ®) | Cutaneous manifestations of T-cell lymphoma | Selectively binds to and activates retinoid X receptors (RXRs), thereby inducing changes in gene expression that lead to cell differentiation, decreased cell proliferation, apoptosis of some cancer cell types, and tumor regression |
| Sympathoimetic amine | Methylphenidate (Daytrana ®; Ritalin ®, Methylin ®, Metadate CD ®, Concerta ®) | Attention deficit hyperactivity disorder; narcolepsy | Activates the brain stem arousal system and cortex to produce its stimulant effect and, in some clinical settings, may improve cognitive function. |
| Sympathoimetic amine | Dexmethylphenidate HCl (Focalin ®) | Attention deficit hyperactivity disorder | Activates the brain stem arousal system and cortex to produce its stimulant effect and, in some clinical settings, may improve cognitive function. |
| Sympathoimetic amine | Dextroamphetamine sulfate (Dexedrine ®) | Attention deficit hyperactivity disorder; narcolepsy | Elevates blood pressure and causes bronchodilation |

TABLE 8-continued

Examples of Miscellaneous Agents Useful for Treating Neoplastic Diseases

| Type of Agent | Example | Neoplasms/Disease | Proposed Mechanism of Action |
|---|---|---|---|
| Synthetic analog | Paricalcitol (Zemplar®) | Secondary hyperparathyroidism associated with chronic kidney disease | Synthetic noncalcemic, nonphosphatemic vitamin D analogue that binds to the vitamin D receptor and has been shown to reduce parathyroid hormone (PTH) levels |
| Class I antiarrhythmic | Disopyramide phosphate (Norpace®) | Life-threatening ventricular arrhythmias | Decreases rate of diastolic depolarization in cells with augmented automaticity, decreases upstroke velocity, and increases action of potential duration of normal cardiac cells |
| ACE inhibitor/calcium channel blocker (nondihydropyridine) | Trandolapril-verapamil HCl (Tarka®) | Hypertension | ACE inhibitor, calcium channel blocker |
| Opioid analgesic | Methadone HCl (Dolophine®) | Opioid analgesic; μ-agonist; also acts as an antagonist at the N-methyl-D-aspartate (NMDA) receptor | Detoxifiction and temporary maintenance treatment of narcotic addiction; relief of severe pain |
| 5-hydroxy-trypt amine, receptor agonist | Sumatriptan Succinate (Imitrex®) | Migraine, cluster headache | Selective agonist for a vascular 5-hydroxytryptamine$_1$ receptor subtype |
| Immune response modifying agent | Imiquimod (Aldara®) | Actinic keratosis, superficial basal cell carcinoma, external genital warts | Stimulates cytokine production, especially interferon production, and exhibits antitumor activity, particularly against cutaneous cancers |
| Serotonin reuptake inhibitor | Fluvoxamine maleate (Luvox®) | Obsessive compulsive disorder, social anxiety disorder | Serotonin reuptake inhibition |
| Norepinephrine (noradrenaline) reuptake inhibitor | Atomoxetine HCl (Strattera®) | Attention deficit hyperactivity disorder | Unknown |

6.1. Kinase Inhibitors

Antineoplastic kinase inhibitors include, but are not limited to, Sorafenib tosylate (Nexavar®), a synthetic compound that targets growth signaling and angiogenesis, and Erlotinib hydrochloride (Tarceva®), the salt of a quinazoline derivative with antineoplastic properties.

6.2. Platinum Coordination Complexes

Examples of antineoplastic agents that form platinum coordination complexes include, but are not limited to, Cisplatin (cis-diamminedichloroplatinum (II), Platinol-AQ®), a divalent inorganic water-soluble, platinum containing complex that appears to enter cells by diffusion and reacts with nucleic acids and proteins, is a component of several combination chemotherapy regimens. For example, it is used with bleomycin, etoposide and vinblastine for treating patients with advanced testicular cancer, and with paclitaxel, cyclophosphamide or doxorubicin for treating ovarian cancer.

Another antineoplastic agent that forms a platinum coordination complex is Carboplatin (CBDCA, JM-8), which has a mechanism and spectrum of clinical activity similar to cisplatin, but generally is less reactive than cisplatin.

An additional antineoplastic agent is Oxaliplatin (trans-1-diaminocyclohexane oxalatoplatinum), which, like cisplatin, has a wide range of antitumor activity and is active in ovarian cancer, germ-cell cancer and cervical cancer. Unlike cisplatin, oxaliplatin in combination with 5-fluorouracil is active in colorectal cancer.

6.3. EDTA Derivatives

Other antineoplastic agents include EDTA-derivatives. Such compounds include, but are not limited to, Dexrazoxane hydrochloride (Zincard®), the salt of a bisdioxopiperazine with iron-chelating, chemoprotective, cardioprotective, and antineoplastic activities.

6.4. Platelet-Reducing Agent

Anagrelide hydrochloride (Agrlyin®) is a platelet-reducing agent used to treat thrombocythemia, secondary to myeloproliferative disorders, to reduce the elevated platelet count and the risk of thrombosis and to ameliorate associated symptoms including thrombo-hemorrhagic events.

6.5. Retinoids

Retinoids are a group of substances related to vitamin A and function like vitamin A in the body. Retinoids include, but are not limited to, bexarotene (Targretin®), a synthetic retinoic acid agent with potential antineoplastic, chemopreventive, teratogenic and embryotoxic properties; and isotretinoin (Accutane®), a naturally-occurring retinoic acid with potential antineoplastic activity.

6.6. Histone Deacetylase Inhibitors

The histone deacetylase inhibitor vorinostat (Zolinza®) is a synthetic hydroxamic acid derivative with antineoplastic activity, and a second generation polar-planar compound that binds to the catalytic domain of the histone deacetylases (HDACs). This allows the hydroxamic moiety to chelate zinc ion located in the catalytic pockets of the HDAC, thereby inhibiting deacetylation and leading to an accumulation of both hyperacetylated histones and transcription factors. Hyperacetylation of histone proteins results in the upregulation of the cyclin-dependant kinase p21, followed by $G_1$ arrest. Hyperacetylation of non-histone proteins such as tumor suppressor p53, alpha tubulin, and heat-shock protein 90 produces additional anti-proliferative effects. Vorinostat also induces apoptosis and sensitizes tumor cells to cell death processes.

7. Chemotherapeutic Drugs Useful for Treating Multiple Myeloma (MM)

7.1 Immunomodulatory Drugs

Immunomodulatory drugs effective in treating MM include, but are not limited to, Thalidomide, and its synthesized analogs Lenalidomide and Pomalidomide. Thalidomide and Lenalidomide are oral agents shown to be effective across the spectrum of myeloma disease (Rajkumar S V, Mayo Clin Proc. 2004; 79: 899-903; Kyle R A et al., Blood. 2008; 111: 2962-2972). The mechanism of action of both Thalidomide and Lenalidomide in MM is not fully understood. Proposed mechanism(s) include the inhibition of tumor necrosis factor-alpha (TNF alpha), prevention of free-radical-mediated DNA damage, suppression of angiogenesis, increase in cell-mediated cytotoxic effects, and alteration of the expression of cellular adhesion molecules, inhibition of the activity of nuclear factor kappa B (NF-kappa B) and the enzymes cyclooxygenase-1 and cyclooxygenase-2, and promotion of the cytotoxic activity of natural killer and T cells by stimulating their proliferation and secretion of interleukin 2 and interferon gamma. Evaluation of immune function in MM patients treated with Pomalidomide demonstrated a poly-functional T-cell activation and a reduction of transcription factors on and enhanced function of innate lymphoid cells (Sehgal K, et al. Blood (2015) 125:4042-51; Kini Bailur J, et al. Blood Adv. 2017 Nov. 28; 1(25):2343-2347).

7.2 Proteasome Inhibitors

Proteasome inhibitors effective in treating MM include, but are not limited to, Bortezomib. Bortezomib, a first-in-class proteasome inhibitor, targets the 26S proteasome, a multicatalytic proteinase complex involved in intracellular protein degradation. Bortezomib inhibits transcription factor NF-kappaB activation by protecting its inhibitor I kappa B (IkappaB) from degradation by the 26S proteasome. Degradation of I kappa B by proteasome activates NF-kappaB, which up-regulates transcription of proteins that promote cell survival and growth, decreases apoptosis susceptibility, influences the expression of adhesion molecules, and induces drug resistance in myeloma cells (Merchionne F et al., Clin Exp Med. 2007; 7: 83-97). Bortezomib not only targets the myeloma cell, but also acts in the bone marrow microenvironment by inhibiting the binding of myeloma cells to bone marrow stromal cells and bone marrow-triggered angiogenesis.

7.3 Bisphosphonates

Bisphosphonates effective in treating MM include, but are not limited to, Pamidronate and zoledronic acid. Bisphosphonates inhibit the dissolution of the hydroxyapatite crystals and down-regulate osteoclast function (Schwartz R N et al., JMCP, September 2008, Vol. 14, No. 7, pp. S12-S18). Certain bisphosphonates (the more potent nitrogen-containing compounds) also appear to have antitumor activity and have been shown to reduce production of the growth factor interleukin 6 (IL-6), which plays a role in the growth and survival of myeloma cells (Schwartz R N et al., JMCP, September 2008, Vol. 14, No. 7, pp. S12-S18). Pamidronate also stimulates an immune response against MM that is mediated by T cells (Schwartz R N et al., JMCP, September 2008, Vol. 14, No. 7, pp. S12-S18). Pamidronate and zoledronic acid have been shown to induce apoptosis (programmed cell death) in the laboratory (Multiple Myeloma Research Foundation. Bisphosphonate overview, www.multiplemyeloma.org/treatment/3.06.php).

7.4 Immunomodulators/Checkpoint Inhibitors

Checkpoint inhibitors target molecules on immune cells to create new or enhanced immune responses against cancer. Cytokines regulate immune cell maturation, growth, and responsiveness. Adjuvants can stimulate pathways to provide longer protection or produce more antibodies. Immunomodulator targets under evaluation in multiple myeloma clinical trials include:

- CTLA-4: blocking this pathway can help promote expansion and diversification of cancer-fighting T cells;
- IL-2/IL-2R: activating this cytokine pathway can help promote the growth and expansion of cancer-fighting T cells;
- PD-1/PD-L1: blocking this pathway can help prevent cancer-fighting T cells from becoming "exhausted," and can restore the activity of already-exhausted T cells;
- Toll-like receptors (TLRs): activation of these innate immune receptors can help stimulate vaccine-like responses against tumors.

(https://www.cancerresearch.org/immunotherapy/cancer-types/multiple-myeloma)

7.5 Cancer Vaccines

Cancer vaccines are designed to elicit an immune response against tumor-specific or tumor-associated antigens, encouraging the immune system to attack cancer cells bearing these antigens. Cancer vaccines can be made from a variety of components, including cells, proteins, DNA, viruses, bacteria, and small molecules. Cancer vaccine targets under evaluation in multiple myeloma clinical trials include:

- Melanoma-associated antigen (MAGE): the genes that produce these proteins are normally turned off in adult cells, but can become reactivated in cancer cells, flagging them as abnormal to the immune system;
- Survivin: a protein that can prevent cellular death and is overexpressed by a number of cancer cell types;
- Telomerase: an enzyme that helps maintain the health of cellular DNA; exploited by cancer cells to achieve immortality;
- Tumor-associated antigens (TAAs): proteins often expressed at abnormally high levels on tumor cells that can be used to target them; also found on normal cells at lower levels;
- WT1: a protein that is often mutated and abnormally expressed in patients with cancer, especially Wilms' tumor (WT).

(Id.).

7.6 Adoptive Cell Therapy

Adoptive cell therapy takes a patient's own immune cells, expands or otherwise modifies them, and then reintroduces them to the patient, where they can seek out and eliminate cancer cells. In CAR T cell therapy, T cells are modified and equipped with chimeric antigen receptors (CARs) that enable superior anti-cancer activity. Natural killer cells (NKs) and tumor infiltrating lymphocytes (TILs) can also be enhanced and reinfused in patients. Cell-based immunotherapy targets under evaluation in multiple myeloma clinical trials include:

- BCMA: an important signaling receptor found mainly on mature B cells; often expressed by lymphoma and myeloma cells;
- CD19: a receptor found on the surface of almost all B cells that influences their growth, development, and activity; often expressed by leukemia, lymphoma, and myeloma cells;
- CD20: a receptor found on the surface of B cells during their development; often expressed by leukemia, lymphoma, and myeloma cells;

NY-ESO-1: a protein that is normally produced only before birth, but is often abnormally expressed in cancer;

WT1: a protein that is often mutated and abnormally expressed in patients with cancer, especially Wilms' tumor (WT).

(Id.).

7.7 Oncolytic Virus Therapy

Oncolytic virus therapy uses modified viruses that can infect tumor cells and cause them to self-destruct. This can attract the attention of immune cells to eliminate the main tumor and potentially other tumors throughout the body. Viral platforms under evaluation in multiple myeloma clinical trials include:

Measles virus: a highly contagious virus that infects the respiratory tract and can cause measles;

Reovirus: a family of viruses that can affect the gastrointestinal and respiratory tracts in a range of animal species;

Vesicular stomatitis virus: a virus that belongs to the same family as the rabies virus; can cause flu-like symptoms in humans.

(Id.).

7.8 Targeted Antibodies

Targeted antibodies are proteins produced by the immune system that can be customized to target specific markers on cancer cells in order to disrupt cancerous activity, especially unrestrained growth. Antibody-drug conjugates (ADCs) are equipped with anti-cancer drugs that they can deliver to tumors. Bi-specific T cell-engaging antibodies (BiTEs) bind both cancer cells and T cells in order to help the immune system respond more quickly and effectively. There are currently two FDA-approved targeted antibody immunotherapy options for multiple myeloma:

Daratumumab (Darzalex®): a monoclonal antibody that targets the CD38 pathway; approved for subsets of patients with advanced multiple myeloma;

Elotuzumab (Empliciti®): a monoclonal antibody that targets the SLAMF7 pathway; approved for subsets of patients with advanced multiple myeloma.

(Id.).

Antibody targets under evaluation in multiple myeloma clinical trials include:

BCMA: an important signaling receptor found mainly on mature B cells; often expressed by lymphoma and myeloma cells;

CD19: a receptor found on the surface of almost all B immune cells that influences their growth, development, and activity; often expressed by leukemia, lymphoma, and myeloma cells;

CD20: a receptor found on the surface of B immune cells during their development; often expressed by leukemia, lymphoma, and myeloma cells;

CD38: an immune cell surface protein that plays roles in cell adhesion and signaling; often expressed by leukemia and myeloma cells;

CD52: a protein found on the surface of mature immune cells as well as other cell types;

EGFR: a pathway that controls cell growth and is often mutated in cancer;

HER2: a pathway that controls cell growth and is commonly overexpressed in cancer and associated with metastasis;

SLAMF7: a surface protein found on plasma B cells; often expressed by lymphoma and myeloma cells.

(Id.).

According to some embodiments, the chemotherapeutic agent is selected from the group consisting of an alkylating agent, an antimetabolite, a natural product, a hormone, a biologic, a kinase inhibitor, a platinum coordination complex, an EDTA derivative, a platelet-reducing agent, a retinoid and a histone deacetylase inhibitor. According to some embodiments, the chemotherapeutic agent is selected from the group consisting of an immunomodulatory drug, a proteasome inhibitor, a bisphosphonate, an immunomodulator or checkpoint inhibitor, a cancer vaccine, an adoptive cell therapy, an oncolytic virus therapy, or a targeted antibody. According to some embodiments, the immunomodulatory drug is Thalidomide, Lenalidomide, or Pomalidomide. According to some embodiments, the proteasome inhibitor is Bortezomib. According to some embodiments, the bisphosphonate is Pamidronate or zoledronic acid. According to some embodiments, the immunomodulator or checkpoint inhibitor is a CTLA-4 inhibitor, a IL-2/IL-2R activator, a PD-1/PD-L1 inhibitor, or a TLR activator. According to some embodiments, the cancer vaccine is effective to elicit an immune response to a target selected from a melanoma-associated antigen (MAGE), survivin, telomerase, a tumor-associated antigen (TAA), and WT1. According to some embodiments, the adoptive cell therapy is a CAR T cell therapy, a natural killer cell (NK) therapy, or a tumor infiltrating lymphocytes (TIL) therapy. According to some embodiments, the adoptive cell therapy is effective to target BCMA, CD19, CD20, NY-ESO-1, or WT1. According to some embodiments, the oncolytic virus therapy uses a measles virus, a reovirus, or a vesicular stomatitis virus. According to some embodiments, the targeted antibody is daratumumab or elotuzumab. According to some embodiments, the targeted antibody is an antibody to BCMA, CD19, CD20, CD38, CD52, EGFR, HER2, or SLAMF7.

According to some embodiments, the MM niche further comprises osteoblast-secreted and MM cell-secreted soluble cytokines and growth factors. According to some embodiments, the MM cells are adherent to osteoblasts of the BM niche. According to some embodiments, the MM cells adhere to the osteoblasts of the BM niche by cell-cell interactions. According to some embodiments, the human myeloma cells are cellular components of a bone marrow aspirate. According to some embodiments, the human myeloma cells are cellular components of peripheral blood. According to some embodiments, the human myeloma cells are cellular components of a core biopsy.

According to some embodiments, the period of time for dynamic propagation of the human myeloma cells in the ex vivo dynamic MM cancer niche is at least 4 days. According to some embodiments, the sample of human myeloma cells added to the BM niche constitutes $1 \times 10^4$ to $1 \times 10^5$ mononuclear cells. According to some embodiments, the sample of human myeloma cells added to the BM niche constitutes about $1 \times 10^4$ mononuclear cells, about $2 \times 10^4$ mononuclear cells, about $3 \times 10^4$ mononuclear cells, about $4 \times 10^4$ mononuclear cells, about $5 \times 10^4$ mononuclear cells, about $6 \times 10^4$ mononuclear cells, about $7 \times 10^4$ mononuclear cells, about $8 \times 10^4$ mononuclear cells, about $9 \times 10^4$ mononuclear cells, about or about $1 \times 10^5$ mononuclear cells. According to some embodiments, propagation of the MM cells in the ex vivo MM cancer niche under conditions that mimic interstitial flow; shear stresses exerted by the interstitial flow on the cells; increased blood flow associated with tumor cell expansion, or a combination thereof is effective to produce deterioration of the 3D ossified tissue of the BM niche. According to some embodiments, the method further comprises cultivating the human myeloma cells in the MM cancer niche to propagate the MM cells for a period of time. According to some embodiments, the MM cancer niche is effective to maintain viability and proliferative capacity of the MM cells for at least 3 weeks. According to some embodiments, the method further comprises testing chemotherapeutic efficacy of a chemotherapeutic agent on the viable human MM cells maintained in the ex vivo MM cancer niche of (c)(3) in the test chamber of (a) by contacting the ex vivo MM cancer niche comprising viable human myeloma cells with a test chemotherapeutic agent under conditions that mimic interstitial flow; shear stresses exerted by the interstitial flow on the cells; increased blood flow associated with tumor cell expansion, or a combination thereof.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Device Design and Features

A 96-well plate-based perfusion device was developed that can be used to maintain the viability and proliferative capacity of PMMC over 3 weeks.[15] We found that: (1) the adhesion of PMMC to osteoblasts (OSB) and the long-term viability of OSB are critical factors for the ex vivo survival of PMMC and (2) perfusion flow rate can be optimized to increase the long-term viability of PMMC.[15-17] While these findings support the culture platform's capability to recapitulate critical environmental factors associated with the survival of patient tumor cells, the high-throughput operation of this dynamic culture platform has been limited since the use of external pumps and tubing connections is labor-intensive and error-prone to cause bubble formation and fluid leakage.[18-20]

We completely redesigned our culture platform to facilitate its high-throughput use by implementing a gravity-driven, pumpless flow control strategy (FIG. 1). Pumpless microfluidic culture has been increasingly pursued to reduce the complexity and difficulty of fluidic management. Hydrostatic pressure,[21,22] capillary force,[23] and surface tension[24] are commonly utilized as passive driving forces to generate fluid flow. We selected to use gravity-based medium feeding because: (1) it can be implemented in a high-throughput manner in synchronization with the automated operation of a commercial plate dispenser and (2) it has been previously demonstrated by Yuen et al.[18] in a 96-well plate format for dynamic cell culture through the use of a flow rate-controlling membrane between wells.

Figure 1C:
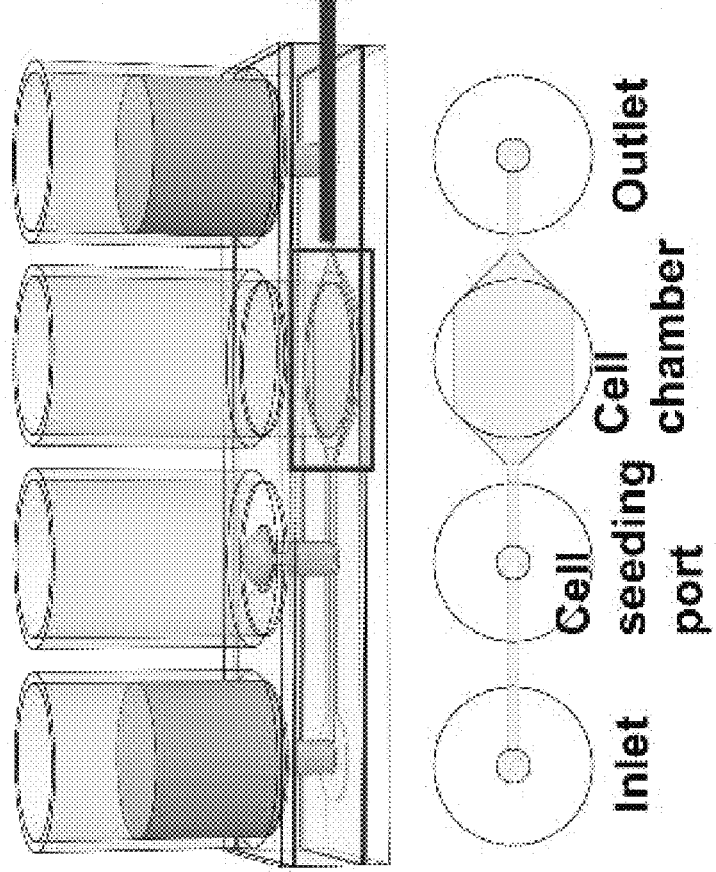
Figure 1D:
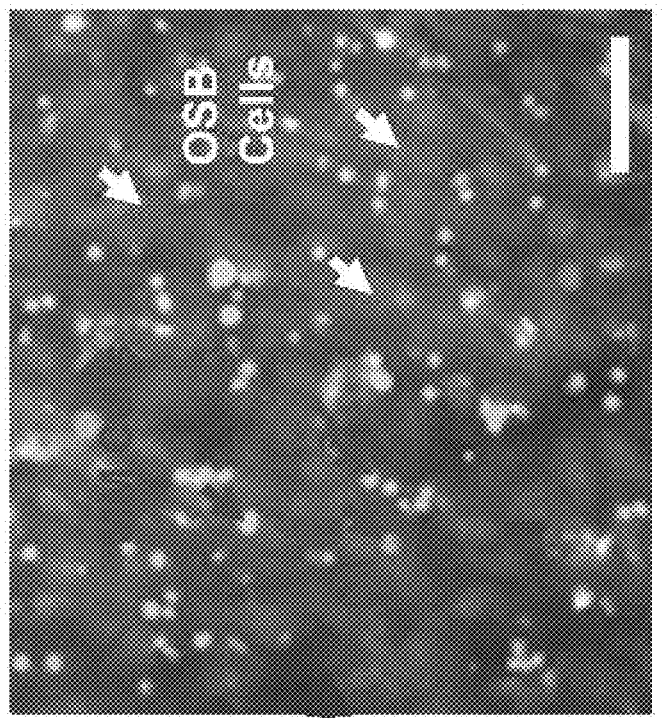

As shown in FIGS. 1a and 1b, the pumpless platform consists of a 96-well plate based microfluidic device and a programmable rocking device, which are housed in an incubator. The microfluidic device contains 20 culture chambers with each chamber occupying 4 wells (FIG. 1c). The inlet and outlet wells function as the reservoirs for culture medium and to generate a hydrostatic pressure differential between the wells (ΔP). Cells are plated through the cell seeding port. The device is designed to enable imaging of cell cultures via high content screening (HCS) or conventional microscopy. FIG. 1d, obtained with HCS, shows osteoblasts (OSB) and MM cells co-cultured in the culture chamber and stained in situ with viability stains prior to imaging. HCS compatibility is an important feature of the culture platform, as it has become a core technique in the early stage of drug discovery.[25] It enables rapid collection and analysis of images and extraction of useful information at a rate that far outpaces conventional microscopy and flow cytometry.

Figure 2:
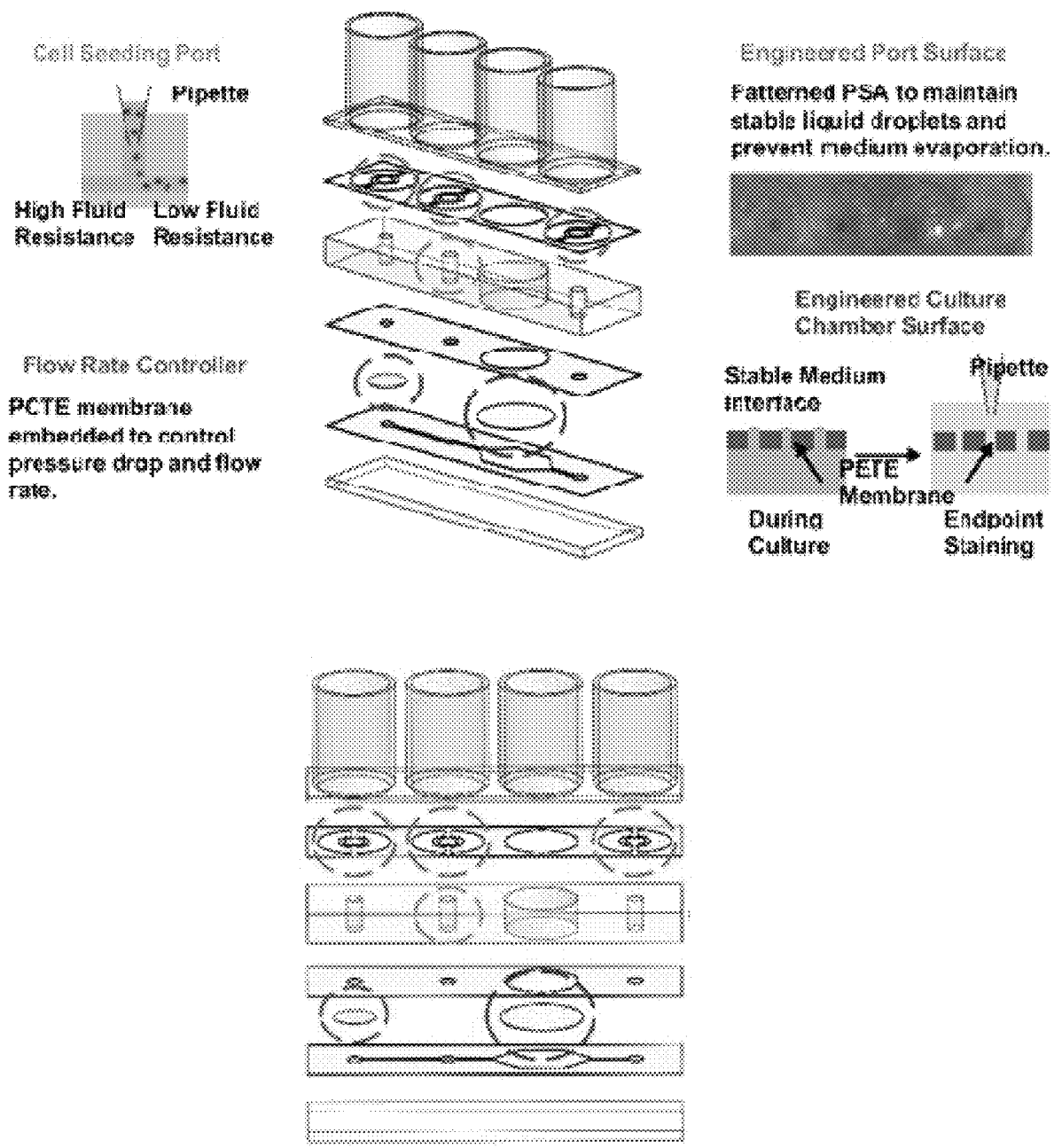
FIG. 2 shows the major design features of the pumpless culture platform. The center pictures (top and bottom) show different views of the fabricated assembly of microfluidic device components. The location circled in gold shows the cell seeding port to direct cell placement into the culture chamber. The blue circle shows the membrane to control medium flow rate. Areas circled in green show the port surface patterned to mitigate medium evaporation during long-term culture. The red circle shows the culture chamber surface, engineered to retain cells during in situ cell washing and staining.

FIG. 2 shows the components of the microfluidic device with detailed illustrations of its design features. As illustrated in FIG. 2 (outlined in gold), the seeding port was designed to allow the insertion of a 200 μL pipette tip into the port and therefore directly pipette cells to the culture chamber. Prior to seeding, the chamber is conditioned with culture medium. Cells are directed to the culture chamber due to the high fluid resistance present in the left channel. The culture chamber is connected to the cell seeding port by a microchannel of dimensions 0.5 mm width and 0.137 mm depth. The culture chamber is hexagonal in shape with a lateral surface area of 38.3 $mm^2$, which is comparable to that of a typical 96 well plate (38.5 $mm^2$). The thickness of the culture chamber is 0.137 mm.

In order to control the medium flow rate (Q) through the culture chamber,[26] a 0.4 μm pore size polycarbonate (PCTE) membrane is imbedded, as a flow rate controller, in the inlet well (outlined in blue). Since the flow is laminar (meaning a steady, continuous stream of fluid, in which the fluid travels smoothly or in regular paths), the Hagen-Poiseuille equation can be used to calculate Q that is generated by ΔP:

$$\frac{\Delta P}{Q} = \frac{32\mu L_m}{\varepsilon A_m d_m^2} \quad (1)$$

where ΔP is the pressure drop between the medium reservoirs, μ is the dynamic viscosity of the medium (0.7 mPa·s under the incubator condition), ε is the porosity of the membrane (10% for the 0.4 μm PCTE membrane), $A_m$ is the surface area of the membrane (1.77 mm²), $L_m$ is the thickness of the membrane (10 μm), and $d_m$ is the average pore diameter (meaning the pore width or distance between two walls of a pore) of the membrane (0.4 μm). For example, Q of 0.5 μL/min can be generated in the culture chamber if ΔP is 67 Pa. The corresponding wall shear stress (c) at the bottom surface of the culture chamber is calculated to be 0.4 mPa using:

$$\tau = \frac{6\mu Q}{h_c^2 w_c} \quad (2)$$

where $h_c$ is the height of the culture chamber (0.137 mm) and $w_c$ is the chamber width (5.35 mm).

Figure 3A:
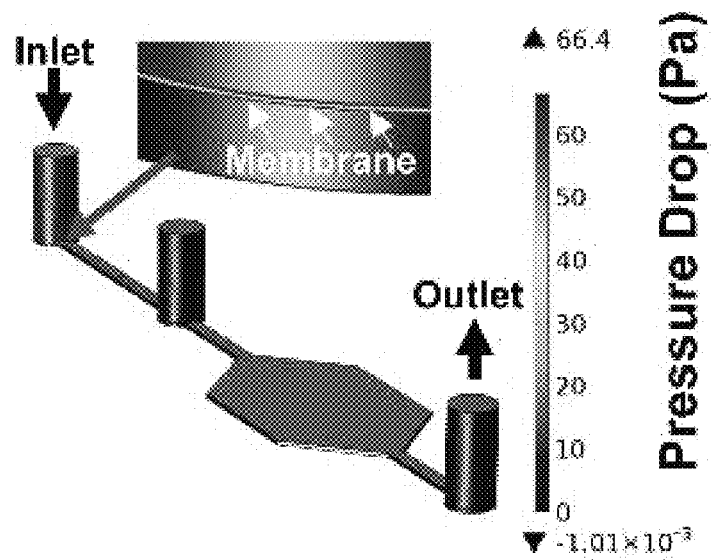
FIG. 3A shows a computational simulation of pressure drop contours through fluidic passages.
Figure 3B:
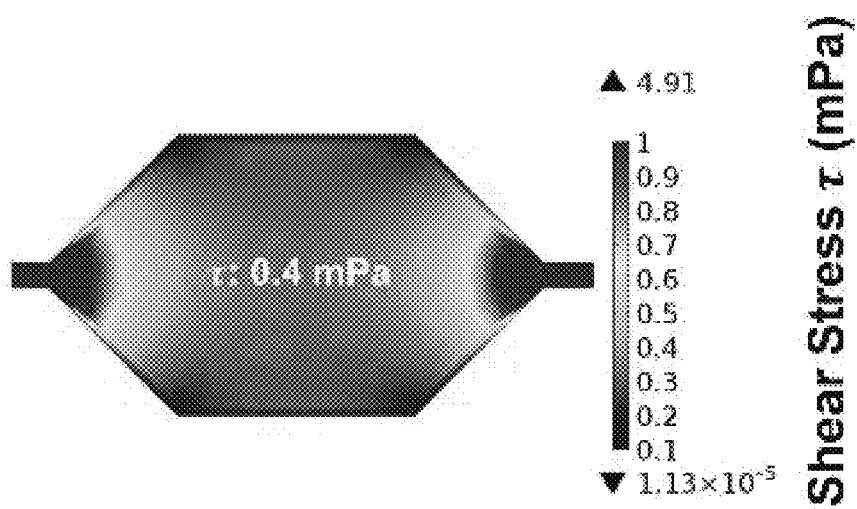
FIG. 3B shows a computational simulation of wall shear stress contours in the cell chamber.

Computational simulation results, summarized in FIG. 3, support the analytical solutions, i.e., a pressure drop of 67 Pa can be used to generate a flow rate of ~0.5 μl/min and τ of ~0.4 mPa in the culture chamber. The simulation results were obtained using the computational fluidic dynamic module of Comsol 5.0. As can be seen from the pressure drop contours in FIG. 3a, the major pressure drop occurs when the medium goes through the PCTE membrane in the inlet well. FIG. 3b shows that shear stress distribution was relatively uniform with the shear stress of 0.4 mPa on most part of the culture chamber.

FIG. 4 illustrates how the degree of tilting of the rocking device can be controlled with time to control Q to be within 10% during culture. Since the medium level difference decreases continuously with time (t) under this gravity-based approach, time-dependence on the medium level difference (Δh) and the medium flow rate (Q) in the culture chamber can be accounted for using:

$$\Delta h = \Delta h_0 e^{-2Q_0 t/\Delta h_0 A} \quad (3)$$

$$Q = Q_0 e^{-2Q_0 t/\Delta h_0 A} \quad (4)$$

where $\Delta h_0$ is the initial medium level difference, A is the cross-sectional area of a 96-well, $Q_0$ is the initial flow rate (0.5 μL/min). Note that the residence time of the medium in the culture chamber, based on $Q_0$, is ~17 min.

Figure 4A:
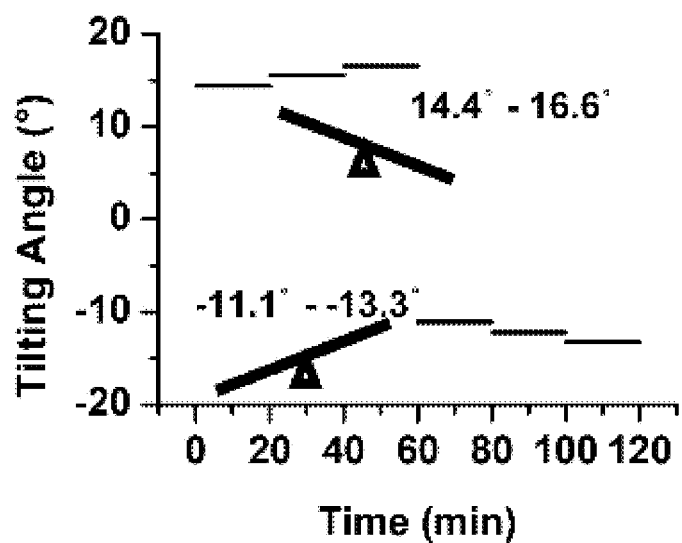
FIG. 4A-FIG. 4B show graphs of how the medium flow rate is controlled by the tilting angle of the rocking device with respect to time.
Figure 4B:
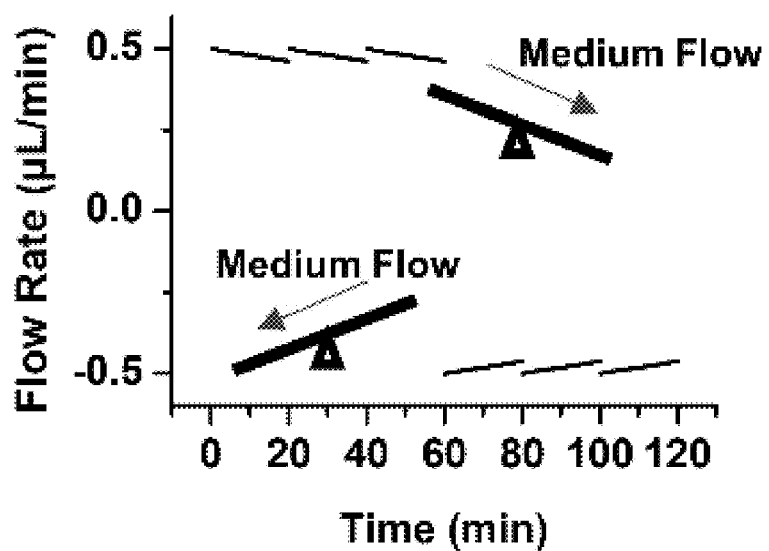
Figure 6A:
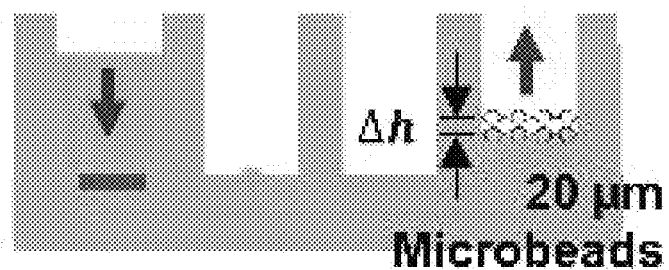
FIG. 6A-FIG. 6D show flow visualization using the fabricated device.
Figure 6B:
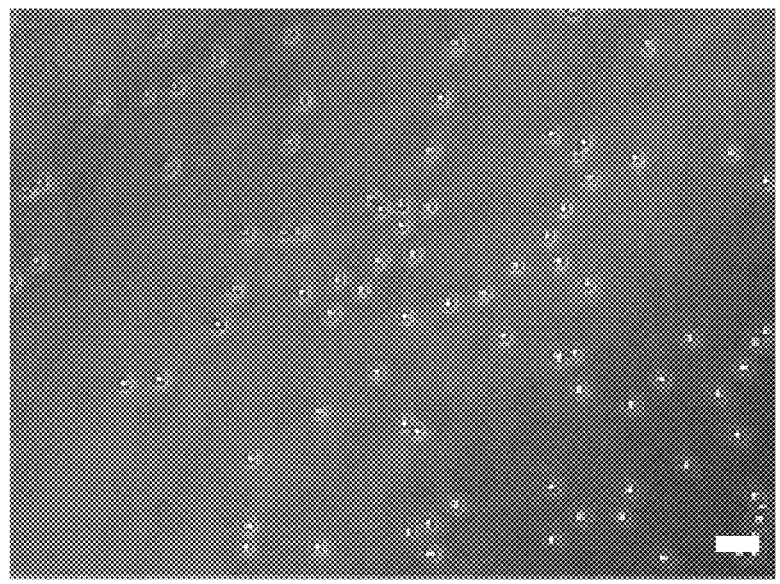
Figure 6C:
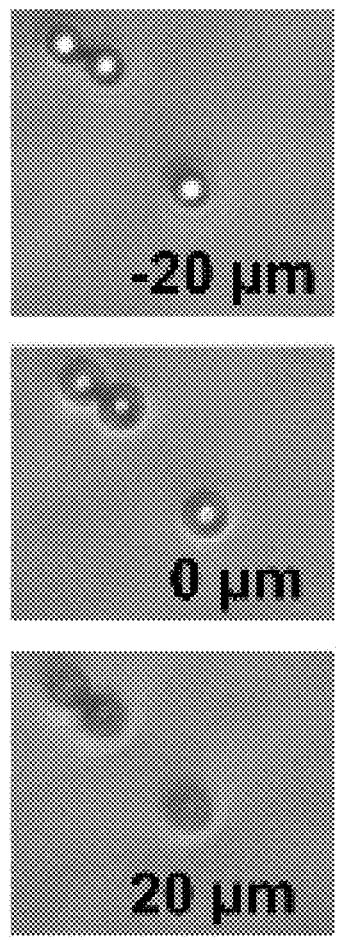
Figure 6D:
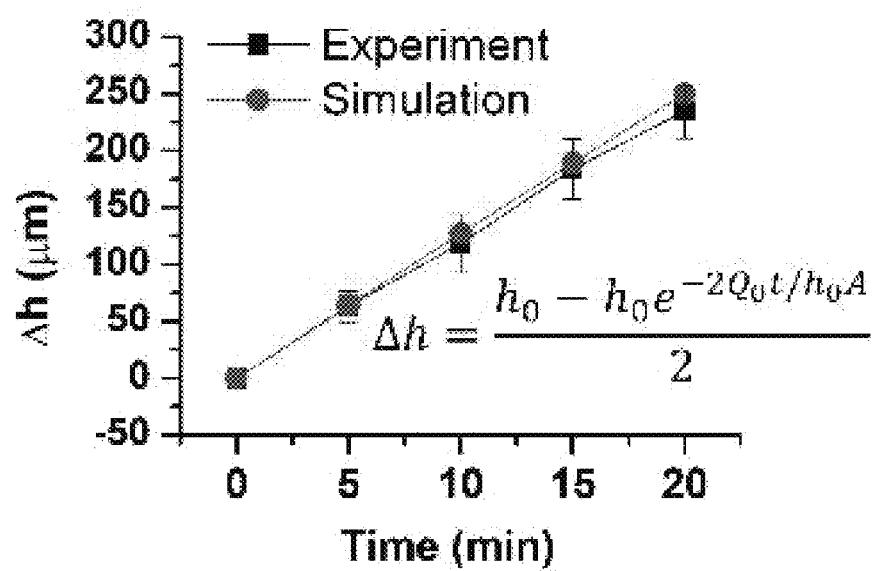

In order to maintain Q within 10%, the tilting angle of the rocking device is increased from 14.4 to 15.5 degree after 20 minutes into culture (FIG. 4a). This 1.1 degree increase is repeated for two more 20-minute intervals. Then, the tilting position is reversed to −11.1 degree to re-establish $\Delta h_0$ and the incremental tilting angle changes are repeated. FIG. 4b shows that this tilting control strategy results in bi-directional fluid flow with Q in the range of 0.46 to 5 μL/min. The overall time spent for one tilting cycle is 120 min. During this time, ~60 μL of the medium passes through the chamber.

FIG. 2 illustrates the surface pattern (outlined in green) used: (1) to hold the medium in the cell seeding port by surface tension during dynamic culture and (2) to prevent evaporation of liquid in the medium reservoir ports during device pre-treatment and static culture. After seeding cells, several hours are needed for the cells to settle and adhere without fluid flow. During this time, the medium is only present in the culture chamber and the microfluidic passages, but not in the reservoirs. When the medium dries in these small passages and the medium is subsequently added to the reservoirs, bubbles are generated in the microfluidic passages preventing medium flow. In order to mitigate this problem, the surface of the seeding and reservoir ports is patterned. Basically, a digital-cut pressure sensitive adhesive (PSA) tape (Arcare 90106®, Adhesive Research) is adhered with a ring structure exhibited on each port surface. With the patterned PSA layer, a stable medium droplet is created and maintained on the port surface for several hours (FIG. 2, outlined in green). The stable droplet also keeps the medium from evaporating. Furthermore, during culture, the patterned surface of the cell seeding port ensures that the medium does not exit through the seeding port.

FIG. 2 (outlined in red) shows that the top of the culture chamber is covered with a transparent polyester (PETE) membrane with a thickness of 12 μm and a pore size of 0.4 μm. This membrane is used to hold the medium within the chamber during cell seeding and culture. At the end of culture, cell washing and staining are carried on in situ by directly pipetting and aspirating solutions through the membrane. Liquids above and below the membrane are then mixed and equilibrated by diffusion.

Example 2. Device Fabrication

As shown in FIG. 5, the microfluidic device was assembled with a commercial polystyrene bottomless 96 well plate (PS plate, Greiner Bio-One™), a polydimethylsiloxane (PDMS) layer, three PSA layers, and a glass plate (FIG. 5a). The PSA layers were digital-cut into different patterns using digital craft cutter (Silhouettet™ CAMEO). As previously demonstrated,[27] the use of the digital cutter enabled the overall fabrication of the experimental devices to take less than 2 hours including PDMS preparation (degassing and curing) and patterning of the PSA layers.

As shown in FIG. 5a, the first PSA layer, directly adhered to the glass plate, was used to connect the wells and define the lateral shape and dimensions of the culture chamber. The second PSA layer is used to adhere and seal: (1) the PCTE membrane (Sterlitech™ PCT0447100) that controls the flow rate of medium in the culture chamber; and (2) the PETE (Sterlitech™ 1300017) membrane on the culture chamber which is used to hold the medium within the culture chamber during cell seeding and culture. The PCTE membrane was also cut using the digital cutter. The membrane was placed between two thin plastic layers. The sandwiched membrane and layers were taped to the cutting matt and cut. This procedure was useful to protect the membrane from adhesive present on the cutting matt and enable the fabrication of round membrane pieces without any tear or rupture (FIG. 5b). The same procedure was used to prepare the PETE membrane. The third PSA layer was used to pattern the surface of the medium reservoirs and the cell seeding port.

Because of the large and rigid glass plate used for the device bottom, we found it difficult to seal the well plate only with the PSA layers. Introducing the PDMS layer (FIG.

5a) ensured to seal the microfluidic passages to be leak-free. Also, the holes in the PDMS layer were used to guide liquid injections using 200 μL pipette tips during various stages of cell culture, washing, and staining. The holes in the PDMS layer were made using biopsy punchers (Miltex™) of 1.5 mm and 6 mm diameter. The PDMS layer was plasma treated before adhesion to the adjacent PSA layers.

Example 3. Flow Visualization

As shown in FIG. 6, 20 μm polystyrene microbeads (Polybead® Polystyrene Microspheres) were used to visualize flow through the fabricated device. In brief, we filled the culture chamber with phosphate-buffered saline (PBS), pipetted 50 μL of PBS into both medium reservoirs, and then added 10 μl of the microbeads into one of the wells. The surface tension and buoyancy force kept the microbeads floating on the medium surface. The device was left in the incubator for 30 minutes for the liquid to equilibrate and reach 37° C. and then placed under a microscope (Nikon Ti). The bright-field images of the floating microbeads were captured as shown in FIG. 6b. The flow was generated by adding 260 μl of pre-warmed PBS into the inlet well (FIG. 6a). The vertical position of the microbeads, i.e., the height of the liquid, was measured as a function of time using the microscope (FIG. 6b). FIG. 6c shows that the position of the microbeads could be resolved within 20 μm by adjusting focus. The experimentally measured Δh values matched well to those calculated using the design equations (FIG. 6d). In 20 minutes, Δh increased 250 μm in the outlet and flow rate decreased from 0.5 μl/min to 0.46 μl/min. As described in the device design section, a rocking platform was used here to reset the liquid height difference between inlet and outlet, to maintain the flow rate within 10%.

Example 4. Cell Culture

MM.1S (MM cell line, ATCC®CRL-2974) and hFOB 1.19 (human OSB cell line, ATCC® CRL-11372) were purchased from ATCC. MM.1S cells were cultured in high glucose RPMI-1640 medium supplemented with 15% fetal bovine serum (FBS), 2.5 mM of L-glutamine and 1% penicillin/streptomycin. hFOB 1.19 cell medium consisted of a 1:1 mixture of Ham's F12 Medium Dulbecco's Modified Eagle's Medium, with 2.5 mM L-glutamine, 10% FBS and 0.3 mg/ml G418 (Sigma-Aldrich). hFOB 1.19 and MM.1S cells were maintained and propagated in a 5% $CO_2$ incubator at 34° C. and 37° C. respectively. Co-culture experiments were conducted at 37° C. a 1:1 mixture of MM.1S and hFOB 1.19 growth media was used for co-culture. All cell lines were periodically checked for *Mycoplasma* using MycoAlert™ *Mycoplasma* Detection Kit (Lonza). Authentication of cell lines was performed by STR DNA profiling analysis conducted by the Molecular Resources Facility at Rutgers University. Cell populations were frozen after 3 passages from the time of initial receipt and growth and were discarded after 20 passages.
Dynamic Culture of OSB Cells We used the human OSB cell line hFOB 1.19 to validate that the pumpless culture device: (1) supports long-term OSB culture; and (2) can generate flow-induced shear stress that promotes osteoblastic development. Studies[28] have shown that flow-induced shear stress could stimulate OSB proliferation and activity. We have also established the importance of perfusion in maintaining the long term viability of OSB and PMMC.[16]

Before introducing OSB cells, the culture chamber was sterilized with 70% isopropyl alcohol for 30 minutes, and functionalized with fibronectin (Corning™ Fibronectin, Human). Briefly, 20 μL fibronectin solution (150 μg/ml, which equals to 2 μg/cm) was pipetted into the chamber from cell seeding port to fill up the chamber. Then 5 μL solution was also added onto each port to prevent evaporation during coating. The device was left at 37° C. for 1 h, then washed with PBS and OSB growth medium. 10 μL OSB suspension with a cell density of 2 million/mL was introduced through the cell seeding port ($1\times10^4$ cells/chamber), static culture for 4 h to let the OSBs adhere. We observed that there were just a few cells occasionally settled in and attached to the channel between the seeding port and culture chamber. We attributed this behavior to the higher shear stress in the channel than in the culture chamber (4 mPa vs. 0.4 mPa). Then, 100 μL medium was added to both reservoirs, and the device was placed on a rocking platform in a 34° C. incubator to start the dynamic culture. Medium was changed every two days.

The rocking platform was assembled using a commercial rotator (R4040, Benchmark Scientific) and by connecting its stepper motor to a microcontroller (Arduino Uno) and a driver (A4988) on a computer numerical control (CNC) shield. The tilting angle was set to 14.4 degrees initially to generate a 6.7 mm medium level difference between the inlet and outlet wells. According to the tilting control strategy in FIG. 4, a bi-directional medium flow was generated during culture with the flow rate maintained within 10%. Another pumpless device was used as static control. After introducing the cells, 200 μL of medium was pipetted carefully onto the PETE membrane present on top of the culture chamber. The PETE membrane allowed the medium to diffuse into the chamber, and no flow was generated because the medium was held in the ports from entering into the well.

Figure 7A:
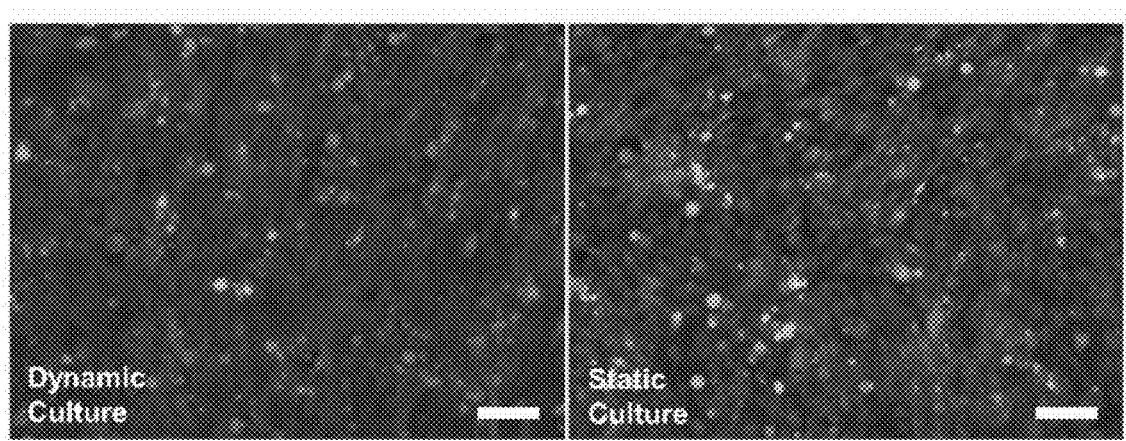
FIG. 7A-FIG. 7C show a comparison of dynamic and static culture of OSB (hFOB 1.19 cells) in the pumpless culture platform.

Cell viability and alkaline phosphatase (ALP, a measurement of osteoblastic activity) were determined after 4-day dynamic culture of OSB. Fluorescent images are shown in FIG. 7a, calcein AM (green) labels live hFOB and displays cell morphology. Most hFOB cells were oriented along with the flow direction under dynamic culture, whereas under static culture, cells show random orientation.

Cell nuclei were stained with 5 μg/ml Hoechst (Hoechst 33324). LIVE/DEAD Viability/Cytotoxicity Kit (0.1 μM calcein AM & 0.1 μM EthD-1; Thermo Fisher Scientific) was used to visualize live and dead cells. Fluorescence images were captured using an inverted microscope (Nikon Ti-E) and analyzed using ImageJ 1.49v. OSB were significantly more viable after 4 days of dynamic culture (93.29%±0.68%) than under static culture conditions (86.76%±2.93%) [*P<0.05, FIG. 7a].

Figure 7B:
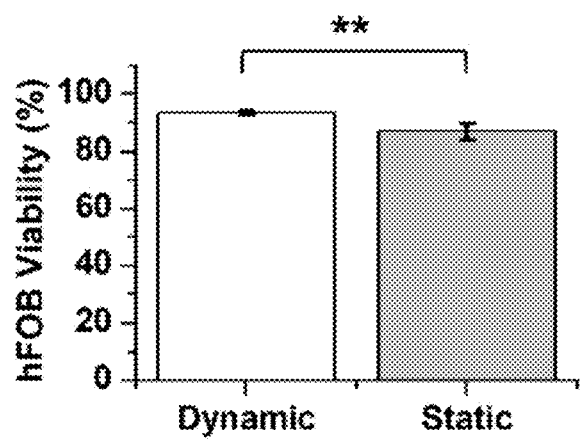
Figure 7C:
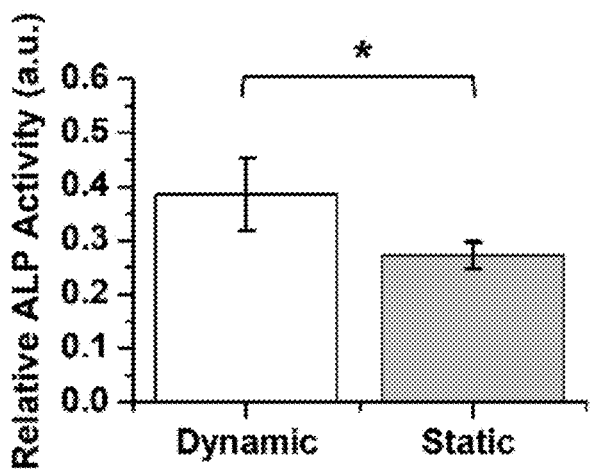

For ALP activity, we used TRACP&ALP assay kit (TaKaRa #MK301). It detects ALP through the use of pNPP (p-nitro-phenyl phosphatase) and it is quantified by measuring the absorbance of the reactant at 405 nm. FIG. 7c shows that the ALP activity was significantly higher under dynamic culture (0.39±0.07) than under static culture (0.27±0.02) [*P<0.05, FIG. 7b]. These results are similar to those established using our previously designed pump-fed culture platform.[17] Therefore, the results validate that the pumpless device can be used to maintain viable OSB, generate flow-induced shear stress, and promote the osteoblastic differentiation of these cells.

Example 5. Chemosensitivity Evaluation of MM Cells Through In Situ Staining and HCS The high-throughput capability of the pumpless culture platform was evaluated by studying the response of MM.1S cells to bortezomib at four different concentrations (0 nM, 5 nM, 10 nM, 20 nM). Bortezomib is a proteasome inhibitor that induces MM cell apoptosis.[29] Before introducing MM.1S cells, OSB were dynamically cultured for 4 days (in a $CO_2$ incubator at 34° C.). MM.1S cells were pre-labeled with 5 µM cell trace violet (Thermo Fisher Scientific), 10 µL MM.1S with a cell density of 4 million/ml were seeded into culture chambers ($2\times10^4$ cells/chamber). The device was then placed inside a $CO_2$ incubator at 37° C. for 4 h to let MM.1S settle prior to starting the flow. Cells were co-cultured for another 24 h, and then treated with bortezomib for 4 h. After drug treatment, the medium was changed and cultures were allowed to recover for a 24 h period before analyses were conducted. MM.1S alone, cultured in the device but under static conditions were used as control.

Cell viability after treatment and recovery was determine as described above, using LIVE/DEAD Viability/Cytotoxicity Kit (0.1 µM calcein AM & 0.1 µM EthD-1). Culture chambers were scanned using HCS (CellInsight™ CX5, Thermo Fisher Scientific). Cell trace violet$^+$ calcein AM$^+$ cells were identified as live MM.1S and cell trace violet$^+$ EthD-1$^+$ cells were identified as dead cells, using pre-design CX5 software algorithms (HCS Studio 2.0 Cell Analysis Software) for cell quantification and rapid analysis.

Figure 8A:
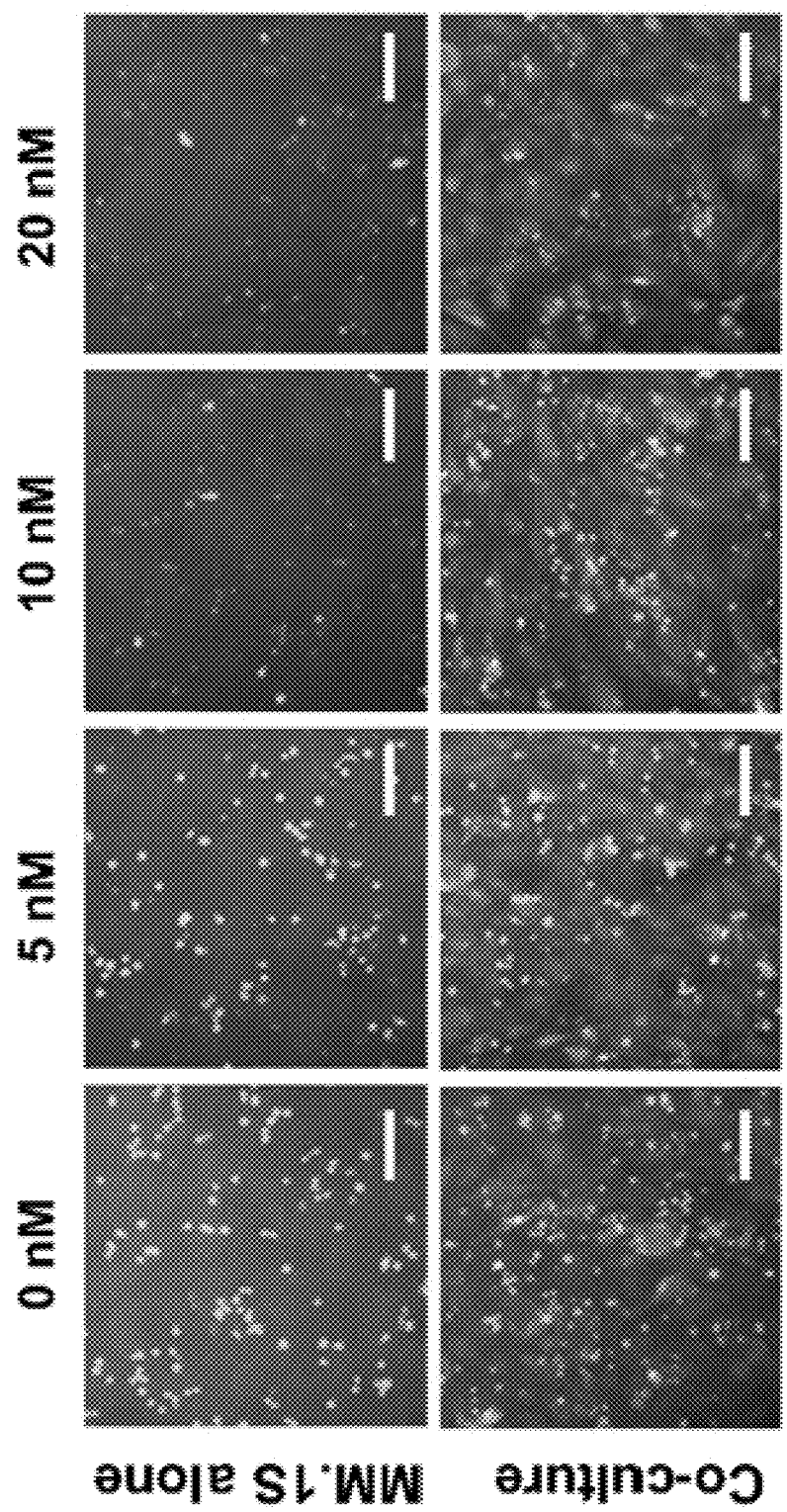
FIG. 8A-FIG. 8C show the effects of bortezomib concentration on cell cultures.

Fluorescent images captured by HCS are shown in FIG. 8a. Due to the lower shear stress and auto-fluorescence on the edge of the culture chambers, we scanned and analyzed the 9 fields in the middle of each chamber. The clearness of the images indicates that the polyester membrane allows efficient exchange of liquid and enables proper staining and identification of cells despite it being auto-fluorescent in the green (excitation/emission (nm): 485/521) and red channel (excitation/emission (nm): 560/607). This artefact was eliminated during image process and analysis to ensure proper counting of live/dead cells. Importantly, the membrane prevented floating or loosely adhered cells from being remove during the staining procedure—a design advantage that is critical to retain and count both suspension and dead cells.

Furthermore, images of MM cells alone show an even distribution of cells throughout the well, indicating that nearly no flow disturbance was generated during cell washing and staining. Of note, bubbles in the culture chamber could be removed automatically through the membrane within a minute. Bubbles in the channels could be also easily pipetted into the culture chamber or directly pipette out with a hard force.

Figure 8B:
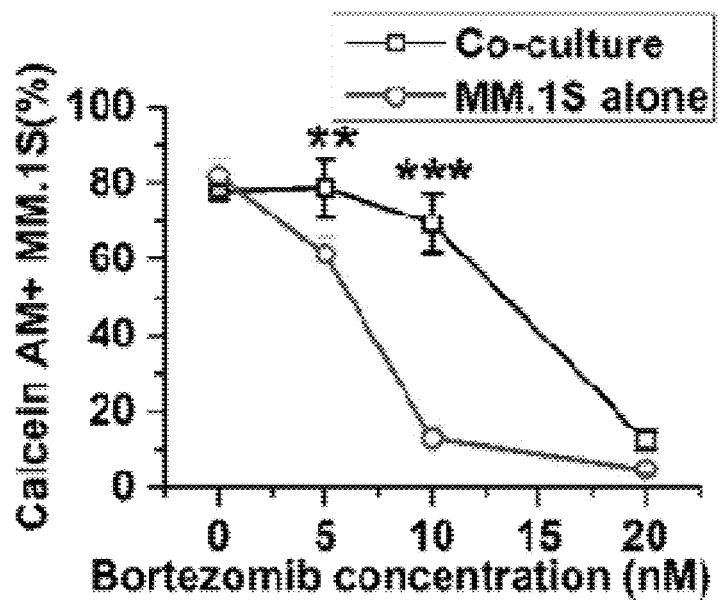
Figure 8C:
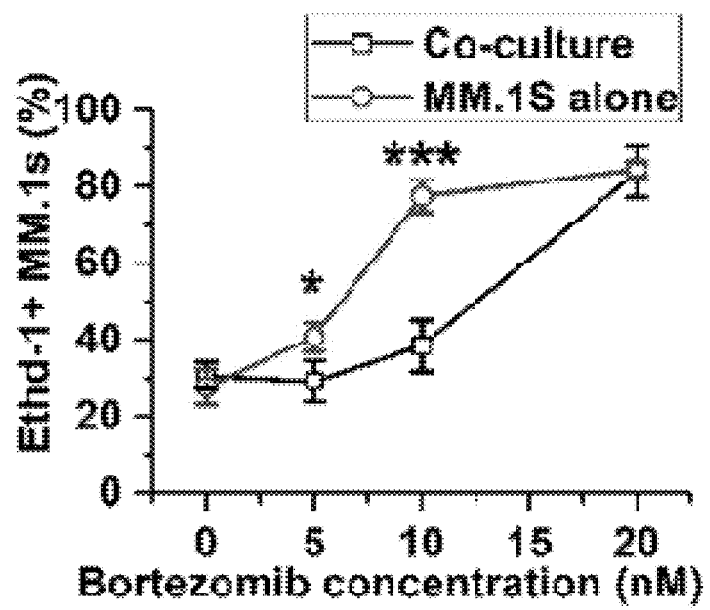

Data quantification was performed automatically using the HCS Studio Software. The percentage of live (cell trace violet$^+$ calcein AM$^+$ cells/cell trace violet$^+$ cells) and dead (cell trace violet$^+$EthD-1$^+$/cell trace violet$^+$ cells) MM.1S cells were plotted against bortezomib concentration. MM.1S in co-culture (FIGS. 8b and 8c) remained significantly more viable (~70%, P<0.05) between the treatment range of 0 nM to 10 nM compared to cells cultured alone (viability ~60% at 5 nM and ~15% at 10 nM), suggesting that MM.1S cells can develop drug resistance when co-cultured with OSB.

Statistics

Statistical analyses were conducted using GraphPad Prism V.7.0. Differences between two groups were calculated using Student's t-test. One way ANOVA followed by Tukey's multiple comparison analysis was conducted to compare multiple groups. A P<0.05 was considered significant.

Discussion

The gravity-driven flow strategy has been previously used to develop pumpless microfluidic culture devices. In comparison to other such systems,[19,30-32] our design enables: (1) the control and maintenance of medium flow within 10% of the set rate (FIGS. 4 and 6) whereas 50% was typically achieved by the others;[30] (2) the placement of the flow rate-controlling membrane in the inlet port (FIG. 2), instead of embedding it in microchannels which can invite difficulties in device fabrication; and (3) the simple use of a programmable rocking platform (FIG. 1a) in comparison to other gravity-generation methods such as horizontal reservoirs[33] and droplet dispenser.[34]

Also, we used a transparent porous membrane at the top of the cell culture chamber to facilitate high-throughput in situ cell staining and imaging (FIG. 2). Conventional cell staining procedures in other microfluidic devices involve pipetting the staining solutions into the cell chamber through channels, which generate a large shear flow. As a result, cell morphology can change and non-adherent as well as less viable cells could be detached and flushed out. Furthermore, staining solutions are passively introduced into the culture chambers, drastically decreasing the staining efficiency.[35] In our design, the membrane use enabled the retention of loosely-adherent cells in the chamber while avoiding bubble formation.

The high-throughput capacity of the pumpless culture platform was demonstrated in this study through the evaluation of MM.1S cells' drug response using HCS in three different aspects: (1) 20 culture chambers in a single well plate, (2) dynamic culture without the setting up difficulties and time required to use tubing and pumps, and (3) in situ staining and HCS. In regard to the use of in situ staining and HSC, entire end-point viability characterization procedures on 20 chambers took less than 1 h. In comparison, conventional characterization based on flow cytometry typically consume over several hours to harvest, stain, and analyze cells.

Our culture platform has also been optimized for: (1) device fabrication based on rapid prototyping using digital cutter, the whole fabrication process takes only 2 hours and (2) device sealing by incorporating a PDMS layer. We developed a method to firmly adhere the PDMS to PSA double-sided tape, which also provides a convenient method to indirectly adhere PDMS to polystyrene surface. We observed that the PSA layers did not cause leaking and bubble problems and adversely affect cell viability during culture. These observations are consistent with results from other microfluidic devices fabricated using PSA.[26,36] In the current device design, PDMS is used to fabricate the microfluidic device and is in direct contact with cell culture medium. It has been reported that PDMS could leach hydrophobic components from cell culture media and store them within the bulk structure of PDMS.[37] To eliminate PDMS, we will need to find a better material to replace the rigid glass bottom, e.g., tissue culture-treated polystyrene plate, in order to seal the culture chamber. Inlet, outlet and cell seeding ports could also be drilled from a polystyrene plate. Furthermore, for high-throughput commercial manufacturing, injection molding could be applied to fabricate device parts, thermal bonding, solvent bonding or adhesive bonding could then be used for assembly.

The pumpless culture platform stimulated osteoblastic differentiation and enabled the formation of a distinct cellular morphology due to the dynamic culture. This flow-induced shear stress is essential for the long term maintenance of OSB and PMMC[16] and is lacking in other comparable in vitro models of MM.[5-7,9,10,14] Importantly, we demonstrated the compatibility of the system with high-throughput staining and HCS screening for drug evaluation purposes of a complex multicellular environment containing OSB and MM cells. In future studies, we will use the device to prospectively correlate the ex vivo response of PMMC to drugs and short-term clinical outcomes.

REFERENCES

1. J. Epstein and S. Yaccoby, in Multiple Myeloma: Methods and Protocols, eds. R. D. Brown and P. J. Ho, Humana Press, Totowa, N.J., 2005, pp. 183-190.
2. K. Yata and S. Yaccoby, Leuk. Off. J. Leuk. Soc. Am. Leuk. Res. Fund, U.K, 2004, 18, 1891-1897.
3. R. A. Fryer, T. J. Graham, E. M. Smith, S. Walker-Samuel, G. J. Morgan, S. P. Robinson and F. E. Davies, PLoS One, 2013, 8, 1-9.
4. M. Zlei, S. Egert, D. Wider, G. Ihorst, R. Wasch and M. Engelhardt, Exp. Hematol., 2007, 35, 1550-1561.
5. J. Jakubikova, D. Cholujova, T. Hideshima, P. Gronesova, A. Soltysova, T. Harada, J. Joo, S.-Y. Kong, R. E. Szalat, P. G. Richardson, N. C. Munshi, D. M. Dorfman and K. C. Anderson, Oncotarget, 2016, 7, 77326-77341.
6. M. V. J. Braham, T. Ahlfeld, A. R. Akkineni, M. C. Minnema, W. J. A. Dhert, F. C. Oner, C. Robin, A. Lode, M. Gelinsky and J. Alblas, Tissue Eng. Part C Methods, 2018, 24, 300-312.
7. J. Kirshner, K. J. Thulien, L. D. Martin, C. Debes Marun, T. Reiman, A. R. Belch and L. M. Pilarski, Blood, 2008, 112, 2935-2945.
8. A. Silva, M. C. Silva, P. Sudalagunta, A. Dlstler, T. Jacobson, A. Collins, T. Nguyen, J. Song, D. T. Chen, L. Chen, C. Cubitt, R. Baz, L. Perez, D. Rebatchouk, W. Dalton, J. Greene, R. Gatenby, R. Gillies, E. Sontag, M. B. Meads and K. H. Shain, Cancer Res., 2017, 77, 3336-3351.
9. M. R. Reagan, Y. Mishima, S. V. Glavey, Y. Zhang, S. Manier, Z. N. Lu, M. Memarzadeh, Y. Zhang, A. Sacco, Y. Aljawai, J. Shi, Y. T. Tai, J. E. Ready, D. L. Kaplan, A. M. Roccaro and I. M. Ghobrial, Blood, 2014, 124, 3250-3259.
10. P. De La Puente, B. Muz, R. C. Gilson, F. Azab, M. Luderer, J. King, S. Achilefu, R. Vij and A. K. Azab, Biomaterials, 2015, 73, 70-84.
11. T. E. de Groot, K. S. Veserat, E. Berthier, D. J. Beebe and A. B. Theberge, Lab Chip, 2016, 16, 334-44.
12. C. Pak, N. S. Callander, E. W. K. Young, B. Titz, K. Kim, S. Saha, K. Chng, F. Asimakopoulos, D. J. Beebe and S. Miyamoto, Integr. Biol., 2015, 7, 643-654.
13. Z. P. Khin, M. L. C. Ribeiro, T. Jacobson, L. Hazlehurst, L. Perez, R. Baz, K. Shain and A. S. Silva, Cancer Res., 2014, 74, 56-67.
14. J. Waldschmidt, D. Wider, A. Thomsen, C. Aldrian, A. Simon, K. Kortiim, J. Schiller, M. Follo, J. Duyster, R. Wasch and M. Engelhardt, Clin. Lymphoma, Myeloma Leuk., 2015, 15, e224-e225.
15. W. Zhang, Y. Gu, Y. Hao, Q. Sun, K. Konior, H. Wang, J. Zilberberg and W. Y. Lee, Lab Chip, 2015, 15, 2854-63.
16. W. Zhang, Y. Gu, Q. Sun, D. S. Siegel, P. Tolias, Z. Yang, W. Y. Lee and J. Zilberberg, PLoS One, 2015, 10, 1-19.
17. W. Zhang, W. Y. Lee, D. S. Siegel, P. Tolias and J. Zilberberg, Tissue Eng. Part C Methods, 2014, 20, 663-670.
18. V. N. Goral, C. Zhou, F. Lai and P. Ki Yuen, Lab Chip, 2013, 13, 1039.
19. J. H. Sung, C. Kam and M. L. Shuler, Lab Chip, 2010, 10, 446-455.
20. Y. Temiz, R. D. Lovchik, G. V. Kaigala and E. Delamarche, Microelectron. Eng., 2015, 132, 156-175.
21. Y. I. Wang, H. E. Abaci and M. L. Shuler, Biotechnol. Bioeng., 2017, 114, 184-194.
22. V. N. Goral, E. Tran and P. K. Yuena, Biomicrofluidics, 2015, 9, 561-563.
23. S. Chakraborty, Lab Chip, 2005, 5, 421.
24. Y. Xing, M. Nourmohammadzadeh, J. E. M. Elias, M. Chan, Z. Chen, J. J. McGarrigle, J. Oberholzer and Y. Wang, Biomed. Microdevices, 2016, 18, 80.
25. N. Ye, J. Qin, W. Shi, X. Liu and B. Lin, Lab Chip, 2007, 7, 1696-1704.
26. V. N. Goral, E. Tran and P. K. Yuen, Biomicrofluidics, 2015, 9, 054103.
27. P. K. Yuen and V. N. Goral, Lab Chip, 2010, 10, 384-387.
28. S. Kapur, D. J. Baylink and K. H. W. Lau, Bone, 2003, 32, 241-251.
29. S. K. Kumar, S. V. Rajkumar, A. Dispenzieri, M. Q. Lacy, S. R. Hayman, F. K. Buadi, S. R. Zeldenrust, D. Dingli, S. J. Russell, J. A. Lust, P. R. Greipp, R. A. Kyle and M. A. Gertz, Blood, 2008, 111, 2516-2520.
30. S. Y. C. Chen, P. J. Hung and P. J. Lee, Biomed. Microdevices, 2011, 13, 753-758.
31. H. Yamada, Y. Yoshida, N. Terada, S. Hagihara, T. Komatsu and A. Terasawa, Rev. Sci. Instrum., 2008, 79, 124301.
32. I. K. Dimov, G. Kijanka, Y. Park, J. Ducree, T. Kang and L. P. Lee, Lab Chip, 2011, 11, 2701.
33. X. Zhu, L. Yi Chu, B. Chueh, M. Shen, B. Hazarika, N. Phadke and S. Takayama, Analyst, 2004, 129, 1026-1031.
34. T. Kim and Y.-H. Cho, Lab Chip, 2011, 11, 1825.
35. S. Sugiura, J. I. Edahiro, K. Kikuchi, K. Sumaru and T. Kanamori, Biotechnol. Bioeng., 2008, 100, 1156-1165.
36. T. Harkness, J. D. McNulty, R. Prestil, S. K. Seymour, T. Klann, M. Murrell, R. S. Ashton and K. Saha, Biotechnol. J., 2015, 10, 1555-1567.
37. E. W. K. Young, E. Berthier, D. J. Guckenberger, E. Sackmann, C. Lamers, I. Meyvantsson, A. Huttenlocher and D. J. Beebe, Anal. Chem., 2011, 83, 1408-1417.

The invention claimed is:
1. An in vitro multiwell plate-based pumpless perfusion culture device comprising, from top to bottom:
   (i) a bottomless multi-well plate comprising a plurality of bottomless wells, wherein four adjacent sequential wells comprise a culture chamber;
   (ii) a first micropatterned pressure-sensitive adhesive (PSA) layer attached to a bottom surface of the culture chamber;
   (iii) a polymer layer comprising four holes vertically aligned with the four adjacent sequential wells of the culture chamber, the polymer layer being attached to a bottom surface of the first micropatterned PSA layer;
   (iv) a second micropatterned PSA layer attached to a bottom surface of the polymer layer;
   (v) a third micropatterned PSA layer that connects the four adjacent sequential wells, wherein the third micropatterned PSA layer is attached to a bottom surface of the second micropatterned PSA layer;
   (vi) a transparent, optical grade glass layer attached to the bottom surface of the third micropatterned PSA layer that forms a bottom surface for the plurality of wells and that seals the multi-well plate-based pumpless perfusion culture device;
   (vii) a rocking platform for holding the multi-well plate, characterized by rocking speed and an adjustable rocking/tilt angle;

wherein the four adjacent sequential wells that comprise the culture chamber comprise an inlet well, a cell seeding port well, a cell chamber well, and an outlet well;

wherein the first micropatterned PSA layer is effective to maintain stable liquid droplets and to prevent medium evaporation by covering the inlet well, cell seeding port well, and outlet well of the first polymer layer;

wherein the inlet and outlet wells are configured as reservoirs for culture medium and to generate hydrostatic pressure differential between the wells;

wherein the cell seeding port well is adapted to receive a biological sample of cells;

wherein an intermediate layer is disposed between the second micropatterned PSA layer and the third micropatterned PSA layer, the intermediate layer including a first polymer membrane effective to cover the inlet well and to control the flow rate of medium in the culture chamber, and a second polymer membrane different from the first polymer membrane, disposed adjacent to the first polymer membrane and effective to cover the cell chamber well and to hold the medium within the culture chamber during cell seeding and culture; and wherein the second micropatterned PSA layer is effective to adhere and seal the first and second polymer membranes in the culture chamber.

2. The culture device according to claim 1, wherein the polymer layer comprises polydimethylsiloxane (PDMS).

3. The culture device according to claim 1, wherein the first polymer membrane comprises polycarbonate (PCTE).

4. The culture device according to claim 3, wherein the first polymer membrane is characterized by a diameter of about 0.4 µm, a porosity of about 10%, and a thickness of about 10 µm.

5. The culture device according to claim 1, wherein the second polymer membrane comprises polyester.

6. The culture device according to claim 5, wherein the second polymer membrane is characterized by a diameter of about 0.4 µm and a thickness of about 12 µm.

7. The culture device according to claim 1, wherein the cell chamber well is connected to the cell seeding port well by a microchannel.

8. The culture device according to claim 1, wherein the rocking platform is configured to maintain a medium flow rate of about 0.46 to about 5 µL/min.

9. The culture device according to claim 1, wherein the device is configured to maintain a flow-induced shear stress of about 0.4 mPa.

10. An ex vivo multiple myeloma cancer niche contained in a device, in which flow of minute amounts of liquids or dissolved gas molecules, is controlled by microfluidics (a microfluidic device) comprising:

(a) an ex vivo bone marrow microenvironment perfused by nutrients and dissolved gas molecules (a bone marrow niche) comprising viable osteoblasts seeded on a surface of the microfluidic device and cultured to form 3D nodular structures that comprise a 3D bone-like tissue, the 3D bone-like tissue being characterized by an extracellular matrix secreted by the viable osteoblasts; and (b) a multiple myeloma tumor biospecimen comprising viable human multiple myeloma cells;

the microfluidic device comprising, from top to bottom:

(i) a bottomless multi-well plate comprising a plurality of bottomless wells, wherein four adjacent sequential wells comprise a culture chamber;

(ii) a first micropatterned pressure-sensitive adhesive (PSA) layer attached to a bottom surface of the culture chamber;

(iii) a polymer layer comprising four holes vertically aligned with the four adjacent sequential wells of the culture chamber, the polymer layer being attached to a bottom surface of the first micropatterned PSA layer;

(iv) a second micropatterned PSA layer attached to a bottom surface of the polymer layer;

(v) a third micropatterned PSA layer that connects the four adjacent sequential wells, wherein the third micropatterned PSA layer is attached to a bottom surface of the second micropatterned PSA layer;

(vi) a transparent, optical grade glass layer attached to the bottom surface of the third micropatterned PSA layer that forms a bottom surface for the plurality of wells and that seals the multi-well plate-based pumpless perfusion culture device;

(vii) a rocking platform for holding the multi-well plate, characterized by rocking speed and an adjustable rocking/tilt angle;

wherein the four adjacent sequential wells that comprise the culture chamber comprise an inlet well, a cell seeding port well, a cell chamber well, and an outlet well;

wherein the first micropatterned PSA layer is effective to maintain stable liquid droplets and to prevent medium evaporation by covering the inlet well, cell seeding port well, and outlet well of the first polymer layer;

wherein the inlet and outlet wells are configured as reservoirs for culture medium and to generate hydrostatic pressure differential between the wells;

wherein the cell seeding port well is adapted to receive a biological sample of cells;

wherein an intermediate layer is disposed between the second micropatterned PSA layer and the third micropatterned PSA layer, the intermediate layer including a first polymer membrane effective to cover the inlet well and to control the flow rate of medium in the culture chamber, and a second polymer membrane different from the first polymer membrane, disposed adjacent to the first polymer membrane and effective to cover the cell chamber well and to hold the medium within the culture chamber during cell seeding and culture; and wherein the second micropatterned PSA layer is effective to adhere and seal the first and second polymer membranes in the culture chamber;

wherein the microfluidic device is effective to control flow of minute amounts of the liquids, nutrients and dissolved gas molecules in the multiple myeloma cancer niche;

wherein the ex vivo multiple myeloma cancer niche is responsive to changing conditions of perfusion of the ex vivo multiple myeloma cancer niche by the minute amounts of liquids, nutrients and dissolved gas molecules in the microfluidic device; and wherein formation of an ex vivo multiple myeloma microenvironment in the microfluidic device is effective to recapitulate spatial and temporal characteristics of a multiple myeloma cancer niche in vivo and to maintain viability of the multiple myeloma cells in the multiple myeloma cancer niche in the microfluidic device ex vivo.

11. The ex vivo multiple myeloma cancer niche contained in the microfluidic device according to claim 10, wherein the biospecimen comprising human multiple myeloma cells further comprises human plasma autologous to the human multiple myeloma cells.

12. The ex vivo multiple myeloma cancer niche contained in a microfluidic device according to claim 10, wherein the microenvironment perfused by nutrients and dissolved gas molecules of the ex vivo bone marrow niche is effective for propagation of the human myeloma cells.

13. The ex vivo multiple myeloma cancer niche contained in a microfluidic device according to claim 10, wherein the multiple myeloma cancer niche further comprises osteoblast-secreted and multiple myeloma cell-secreted soluble cytokines and growth factors.

14. The ex vivo multiple myeloma cancer niche according to claim 10, wherein,
   (a) the multiple myeloma cells are adherent to osteoblasts of the bone marrow niche; or
   (b) the multiple myeloma cells are adherent to osteoblasts of the bone marrow niche via cell-cell interaction.

15. The ex vivo multiple myeloma cancer niche according to claim 10, wherein
   a. the human multiple myeloma cells are cellular components of a bone marrow aspirate, of peripheral blood, or of a core biopsy; or
   b. the ex vivo multiple myeloma cancer niche is effective for propagation of the human multiple myeloma cells for at least 4 days, or
   c. the ex vivo multiple myeloma cancer niche is effective to maintain the viability and proliferative capacity of patient-derived multiple myeloma cells for at least 3 weeks, or the sample of human multiple myeloma cells added to the bone marrow niche constitutes $1 \times 10^4$ to $1 \times 10^5$ mononuclear cells; or
   d. propagation of the multiple myeloma cells is effective to produce deterioration of the 3D ossified tissue of the bone marrow niche.

16. A method for preparing an ex vivo multiple myeloma cancer niche contained in a device in which flow of minute amounts of liquids or dissolved gas molecules is controlled by microfluidics (a microfluidic device), the microfluidic device comprising, from top to bottom:
   (i) a bottomless multi-well plate comprising a plurality of bottomless wells, wherein four adjacent sequential wells comprise a culture chamber;
   (ii) a first micropatterned pressure-sensitive adhesive (PSA) layer attached to a bottom surface of the culture chamber;
   (iii) a polymer layer comprising four holes vertically aligned with the four adjacent sequential wells of the culture chamber, the polymer layer being attached to a bottom surface of the first micropatterned PSA layer;
   (iv) a second micropatterned PSA layer attached to a bottom surface of the polymer layer;
   (v) a third micropatterned PSA layer that connects the four adjacent sequential wells, wherein the third micropatterned PSA layer is attached to a bottom surface of the second micropatterned PSA layer;
   (vi) a transparent, optical grade glass layer attached to the bottom surface of the third micropatterned PSA layer that forms a bottom surface for the plurality of wells and that seals the multi-well plate-based pumpless perfusion culture device;
   (vii) a rocking platform for holding the multi-well plate, characterized by rocking speed and an adjustable rocking/tilt angle;
   wherein the four adjacent sequential wells that comprise the culture chamber comprise an inlet well, a cell seeding port well, a cell chamber well, and an outlet well;
   wherein the first micropatterned PSA layer is effective to maintain stable liquid droplets and to prevent medium evaporation by covering the inlet well, cell seeding port well, and outlet well of the first polymer layer;
   wherein the inlet and outlet wells are configured as reservoirs for culture medium and to generate hydrostatic pressure differential between the wells;
   wherein the cell seeding port well is adapted to receive a biological sample of cells;
   wherein an intermediate layer is disposed between the second micropatterned PSA layer and the third micropatterned PSA layer, the intermediate layer including a first polymer membrane effective to cover the inlet well and to control the flow rate of medium in the culture chamber, and a second polymer membrane different from the first polymer membrane, disposed adjacent to the first polymer membrane and effective to cover the cell chamber well and to hold the medium within the culture chamber during cell seeding and culture; and
   wherein the second micropatterned PSA layer is effective to adhere and seal the first and second polymer membranes in the culture chamber;
   the method comprising:
   (a) constructing an ex vivo bone marrow microenvironment perfused by nutrients and dissolved gas molecules (a bone marrow niche) in the microfluidic device by:
       (i) seeding a surface of the microfluidic device with viable osteoblasts; and
       (ii) culturing the cells to form 3D nodular structures that comprise a 3D bone-like tissue;
   the 3D bone-like tissue being characterized by an extracellular matrix secreted by the viable adherent osteoblasts;
   (b) preparing a multiple myeloma tumor biospecimen composition comprising viable human multiple myeloma cells from a subject and plasma autologous to the subject; and
   (c) seeding the ex vivo bone marrow microenvironment perfused by nutrients and dissolved gas molecules with the multiple myeloma tumor biospecimen, and forming an ex vivo microenvironment in the microfluidics device effective to recapitulate spatial and temporal characteristics of a multiple myeloma cancer niche in vivo and to maintain viability of the multiple myeloma cells in the multiple myeloma cancer niche in the microfluidics device ex vivo;
   wherein the microfluidic device is effective to control flow of minute amounts of the liquids, nutrients and dissolved gas molecules in the multiple myeloma cancer niche;
   wherein the ex vivo multiple myeloma cancer niche in the microfluidic device is responsive to changing conditions of perfusion of the ex vivo multiple myeloma cancer niche by the minute amounts of liquids, nutrients and dissolved gas molecules in the microfluidics device.

17. The method for preparing an ex vivo multiple myeloma cancer niche according to claim 16, wherein
   a. the multiple myeloma cancer niche further comprises osteoblast-secreted and multiple myeloma cell-secreted soluble cytokines and growth factors; or b. the multiple myeloma cells are adherent to osteoblasts of the bone marrow niche; or
c. the multiple myeloma cells are adherent to osteoblasts of the bone marrow niche via cell-cell interaction; or
d. the human multiple myeloma cells are cellular components of a bone marrow aspirate, of peripheral blood, or of a core biopsy; or
e. the ex vivo multiple myeloma cancer niche is suitable for propagation of the human multiple myeloma cells for at least 4 days; or
f. the ex vivo multiple myeloma cancer niche is effective to maintain the viability and proliferative capacity of patient-derived MM cells for at least 3 weeks; or
g. the sample of human multiple myeloma cells added to the bone marrow niche constitutes $1 \times 10^4$ to $1 \times 10^5$ mononuclear cells; or
h. propagation of the multiple myeloma cells is effective to produce deterioration of the 3D ossified tissue of the bone marrow niche.

18. A method for assessing chemotherapeutic efficacy of a test chemotherapeutic agent on viable human multiple myeloma cells seeded in an ex vivo microenvironment effective to recapitulate spatial and temporal characteristics of a multiple myeloma cancer niche and to maintain viability of the myeloma cells (a multiple myeloma cancer niche) obtained from a subject comprising:
   (a) preparing an in vitro microfluidic device comprising, from top to bottom:
      (i) a bottomless multi-well plate comprising a plurality of bottomless wells, wherein four adjacent sequential wells comprise a culture chamber;
      (ii) a first micropatterned pressure-sensitive adhesive (PSA) layer attached to a bottom surface of the culture chamber;
      (iii) a polymer layer comprising four holes vertically aligned with the four adjacent sequential wells of the culture chamber, the polymer layer being attached to a bottom surface of the first micropatterned PSA layer;
      (iv) a second micropatterned PSA layer attached to a bottom surface of the polymer layer;
      (v) a third micropatterned PSA layer that connects the four adjacent sequential wells, wherein the third micropatterned PSA layer is attached to a bottom surface of the second micropatterned PSA layer;
      (vi) a transparent, optical grade glass layer attached to the bottom surface of the third micropatterned PSA layer that forms a bottom surface for the plurality of wells and that seals the multi-well plate-based pumpless perfusion culture device;
      (vii) a rocking platform for holding the multi-well plate, characterized by a rocking speed and an adjustable rocking/tilt angle;
      wherein the four adjacent sequential wells that comprise the culture chamber comprise an inlet well, a cell seeding port well, a cell chamber well, and an outlet well;
      wherein the first micropatterned PSA layer is effective to maintain stable liquid droplets and to prevent medium evaporation by covering the inlet well, cell seeding port well, and outlet well of the first polymer layer;
      wherein the inlet and outlet wells are configured as reservoirs for culture medium and to generate hydrostatic pressure differential between the wells;
      wherein the cell seeding port well is adapted to receive a biological sample of cells;
      wherein an intermediate layer is disposed between the second micropatterned PSA layer and the third micropatterned PSA layer, the intermediate layer including a first polymer membrane effective to cover the inlet well and to control the flow rate of medium in the culture chamber, and a second polymer membrane different from the first polymer membrane, disposed adjacent to the first polymer membrane and effective to cover the cell chamber well and to hold the medium within the culture chamber during cell seeding and culture; and
      wherein the second micropatterned PSA layer is effective to adhere and seal the first and second polymer membranes in the culture chamber;
   (b) constructing an ex vivo bone marrow microenvironment perfused by nutrients and dissolved gas molecules (a bone marrow niche) by
      (1) seeding a surface of the culture chamber of the in vitro microfluidic device of (a) with a population of cells comprising osteoblasts;
      (2) culturing the cells with a culture medium through the channel region for a time effective for the cells to form a confluent layer on the bottom surface of the channel, to then form multiple cell layers and to then form 3D nodular structures that comprise a 3D bone-like tissue;
      the 3D bone like tissue being characterized by a mineralized bone-like tissue comprising (a) viable osteoblasts self-organized into cohesive multiple cell layers and (b) an extracellular matrix secreted by the viable adherent osteoblasts;
   (c) preparing a multiple myeloma tumor biospecimen composition by:
      (1) acquiring a multiple myeloma tumor biospecimen from the subject, wherein the biospecimen comprises viable multiple myeloma cells; and
      (2) adding plasma autologous to the subject to the viable multiple myeloma cells;
      (3) bringing the biospecimen composition of (c)(2) comprising viable multiple myeloma cells in contact with the osteoblasts of the ex vivo bone marrow microenvironment perfused by nutrients and dissolved gas molecules to seed the ex vivo bone marrow microenvironment with the viable multiple myeloma cells, the ex vivo bone marrow microenvironment perfused by nutrients and dissolved gas molecules and the seeded multiple myeloma cells in contact with the osteoblasts of the ex vivo bone marrow microenvironment forming an ex vivo microenvironment effective to recapitulate spatial and temporal characteristics of a multiple myeloma cancer niche and to maintain viability of the human multiple myeloma cells (a multiple myeloma cancer niche); and
   (d) testing chemotherapeutic efficacy of a chemotherapeutic agent on the viable human multiple myeloma cells maintained in the ex vivo multiple myeloma cancer niche of (c)(3) in the test chamber of (a) by
      (1) contacting the ex vivo multiple myeloma cancer niche comprising viable human myeloma cells with a test chemotherapeutic agent; and
      (2) comparing at least one of viability and level of apoptosis of the multiple myeloma cells in the multiple myeloma cancer niche in the presence of the test chemotherapeutic agent to an untreated control; and (e) initiating therapy to treat the multiple myeloma in the patient with the test chemotherapeutic agent if the test chemotherapeutic agent is effective to significantly (P<0.05) reduce viability of the multiple myeloma cells or to increase apoptosis of the multiple myeloma cells, compared to the untreated control.

19. The method according to claim 18 wherein the chemotherapeutic agent is selected from the group consisting of an alkylating agent, an antimetabolite, a natural product, a hormone, a biologic, a kinase inhibitor, a platinum coordination complex, an EDTA derivative, a platelet-reducing agent, a retinoid and a histone deacetylase inhibitor.

20. The method according to claim 18, wherein the chemotherapeutic agent is selected from the group consisting of an immunomodulatory drug, a proteasome inhibitor, a bisphosphonate, an immunomodulator or checkpoint inhibitor, a cancer vaccine, an adoptive cell therapy, an oncolytic virus therapy, and a targeted antibody.

21. The method according to claim 20, wherein
   the immunomodulatory drug is Thalidomide, Lenalidomide, or Pomalidomide; or
   the proteasome inhibitor is Bortezomib; or
   the bisphosphonate is Pamidronate or zoledronic acid; or
   the immunomodulator or checkpoint inhibitor is a CTLA-4 inhibitor, an IL-2/IL-2R activator, a PD-1/PD-L1 inhibitor, or a TLR activator; or
   the cancer vaccine is effective to elicit an immune response to a target selected from a melanoma-associated antigen (MAGE), survivin, telomerase, a tumor-associated antigen (TAA), and WT1; or
   the adoptive cell therapy is a CAR T cell therapy, a natural killer cell (NK) therapy, or a tumor infiltrating lymphocytes (TIL) therapy, or,
   the adoptive cell therapy is effective to target BCMA, CD19, CD20, NY-ESO-1, or WT1;
   the oncolytic virus therapy uses a measles virus, a reovirus, or a vesicular stomatitis virus; or
   the targeted antibody is daratumumab or elotuzumab, or the targeted antibody is an antibody to BCMA, CD19, CD20, CD38, CD52, EGFR, HER2, or SLAMF7.

22. The method according to claim 18, wherein
   a. the multiple myeloma niche further comprises osteoblast-secreted and multiple myeloma cell-secreted soluble cytokines and growth factors; or
   b. the multiple myeloma cells are adherent to osteoblasts of the bone marrow niche; or
   c. the multiple myeloma cells are adherent to osteoblasts of the bone marrow niche via cell-cell interactions; or
   d. the human multiple myeloma cells are cellular components of a bone marrow aspirate, of peripheral blood, or of a core biopsy; or
   e. the period of time for dynamic propagation of the human myeloma cells in the ex vivo dynamic multiple myeloma cancer niche is at least 4 days; or
   f. the sample of human multiple myeloma cells added to the bone marrow niche constitutes $1 \times 10^4$ to $1 \times 10^5$ mononuclear cells.

23. The method according to claim 18, wherein propagation of the multiple myeloma cells in the ex vivo multiple myeloma cancer niche under conditions that mimic interstitial flow; shear stresses exerted by the interstitial flow on the cells; increased blood flow associated with tumor cell expansion, or a combination thereof is effective to produce deterioration of the 3D ossified tissue of the bone marrow niche.

24. The method according to claim 18, further comprising
   (a) cultivating the human myeloma cells in the multiple myeloma cancer niche to propagate the multiple myeloma cells for a period of time; or
   (b) testing chemotherapeutic efficacy of a chemotherapeutic agent on the viable human multiple myeloma cells maintained in the ex vivo multiple myeloma cancer niche of (c)(3) in the test chamber of (a) by contacting the ex vivo multiple myeloma cancer niche comprising viable human myeloma cells with a test chemotherapeutic agent under conditions that mimic interstitial flow; shear stresses exerted by the interstitial flow on the cells; increased blood flow associated with tumor cell expansion; or a combination thereof.

25. The method according to claim 24, wherein the multiple myeloma cancer niche is effective to maintain viability and proliferative capacity of the multiple myeloma cells for at least 3 weeks.

* * * * *